US007045527B2

(12) United States Patent
Chen et al.

(10) Patent No.: US 7,045,527 B2
(45) Date of Patent: May 16, 2006

(54) PIPERIDINE DERIVATIVES

(75) Inventors: Xiaoqi Chen, San Mateo, CA (US); Kang Dai, Albany, CA (US); Pingchen Fan, Fremont, CA (US); Ying Fu, Menlo Park, CA (US); Leping Li, Burlingame, CA (US); Jeffrey T. Mihalic, San Francisco, CA (US)

(73) Assignee: Amgen Inc., South San Francisco, CA (US)

( * ) Notice: Subject to any disclaimer, the term of this patent is extended or adjusted under 35 U.S.C. 154(b) by 0 days.

(21) Appl. No.: 10/669,606

(22) Filed: Sep. 23, 2003

(65) Prior Publication Data

US 2004/0142956 A1 Jul. 22, 2004

Related U.S. Application Data

(60) Provisional application No. 60/413,335, filed on Sep. 24, 2002.

(51) Int. Cl.
*A61K 31/438* (2006.01)
*C07D 401/06* (2006.01)
*C07D 401/14* (2006.01)

(52) U.S. Cl. ........................................ 514/278; 546/18
(58) Field of Classification Search .................. 546/18; 514/278
See application file for complete search history.

(56) References Cited

U.S. PATENT DOCUMENTS

| 5,219,860 | A | 6/1993 | Chambers et al. |
| 5,324,733 | A | 6/1994 | Billington et al. |
| 5,457,207 | A | 10/1995 | Efange et al. |
| 5,554,752 | A | 9/1996 | Efange et al. |
| 5,780,437 | A | 7/1998 | Goulet et al. |
| 6,200,957 | B1 | 3/2001 | Goulet et al. |
| 6,262,066 | B1 | 7/2001 | Tulshian et al. |

FOREIGN PATENT DOCUMENTS

| EP | 414289 | 2/1994 |
| WO | WO9614318 | 5/1996 |
| WO | WO9721704 | 6/1997 |
| WO | WO9846569 | 10/1998 |
| WO | WO9964002 | 12/1999 |
| WO | WO0006545 | 2/2000 |
| WO | WO0054772 | 9/2000 |
| WO | WO0107606 | 2/2001 |
| WO | WO0206245 | 1/2002 |

OTHER PUBLICATIONS

An, et al., "Identification and Characterization of a melanin-concentrating hormone receptor" *Proc. Natl. Acad. Sci.* (2001) 98:7576-7581.

Bachner, et al., "Identification of melanin concentrating hormone (MCH) as the natural ligand for the orphan somatostatin-like receptor 1 (SLC-1)" *FEBS Lett.*(1999) 457(3):522-524.

Barnes, et al. "Pharmacological Comparison of the Sigma Recognition Site Labeled by $^3$Hhaloperidol in Human and Rat Cerebellum", Naunyn-Schmiedeberg's Arch Pharmacol (1992), 345:197-202.

Bednarek, et al, "Short Segment of Human Melanin-Concentrating Hormone That is Sufficient for Full Activation of Human Melanin-Concentrating Hormone Receptors 1 and 2", Biochemistry (2001) 40:9379-9386.

Bergeron, et al., "Biphasic Effects of Sigma Ligands on the Neuronal Response to N-Methyl-D-Aspartate", Naunyn-Schmiedeberg's Arch Pharmacol (1995), 351:252-260.

Bergeron, et al., Effects of Low and High Doses of Selective Sigma Ligands: Further Evidence Suggesting Existence of Different Subtypes of Sigma Receptors$^3$, Psychopharmacology (1997), 129:215-224.

Boutin, et al, "Melanin-Concentrating Hormone and its Receptors: State of the Art", Can J. Physiol Pharmacol. (2002) 80:388-395.

Chambers, et al. "Melanin-concentrating hormone is the cognate ligand for the orphan G-protein-coupled receptor SLC-1", Nature (1999) 400: 261-265.

Chambers, et al. "Spiropiperidines as High Affinity, Selective σ Ligands",J. Med. Chem (1992) 35: 2033-2039.

Church, et al. "Blockade by Sigma Site Ligands of High-Voltage-Activated $CA^{2+}$ Channels in Rat and Mouse Cultured Hippocampal Pyramidal Neurones", Britsih J. of Pharmacology (1995) 116: 2801-2810.

Couture, et al. "Some of the Effects of the Selective Sigma Ligand (+) Pentazocine Are Mediated Via a Naloxone-Sensitive Receptor" Synapse (2001) 39:323-331.

(Continued)

*Primary Examiner*—Rita Desai
(74) *Attorney, Agent, or Firm*—Jones Day

(57) ABSTRACT

Compounds, compositions and methods are provided that are useful in the treatment or prevention of conditions or disorders associated with a neuropeptide receptor. The subject methods are particularly useful in the treatment and/or prevention of endocrine, metabolic, cardiovascular, neurologic, psychiatric, gastrointestinal, genitourinary and other disorders.

25 Claims, 4 Drawing Sheets

OTHER PUBLICATIONS

Figure 1:
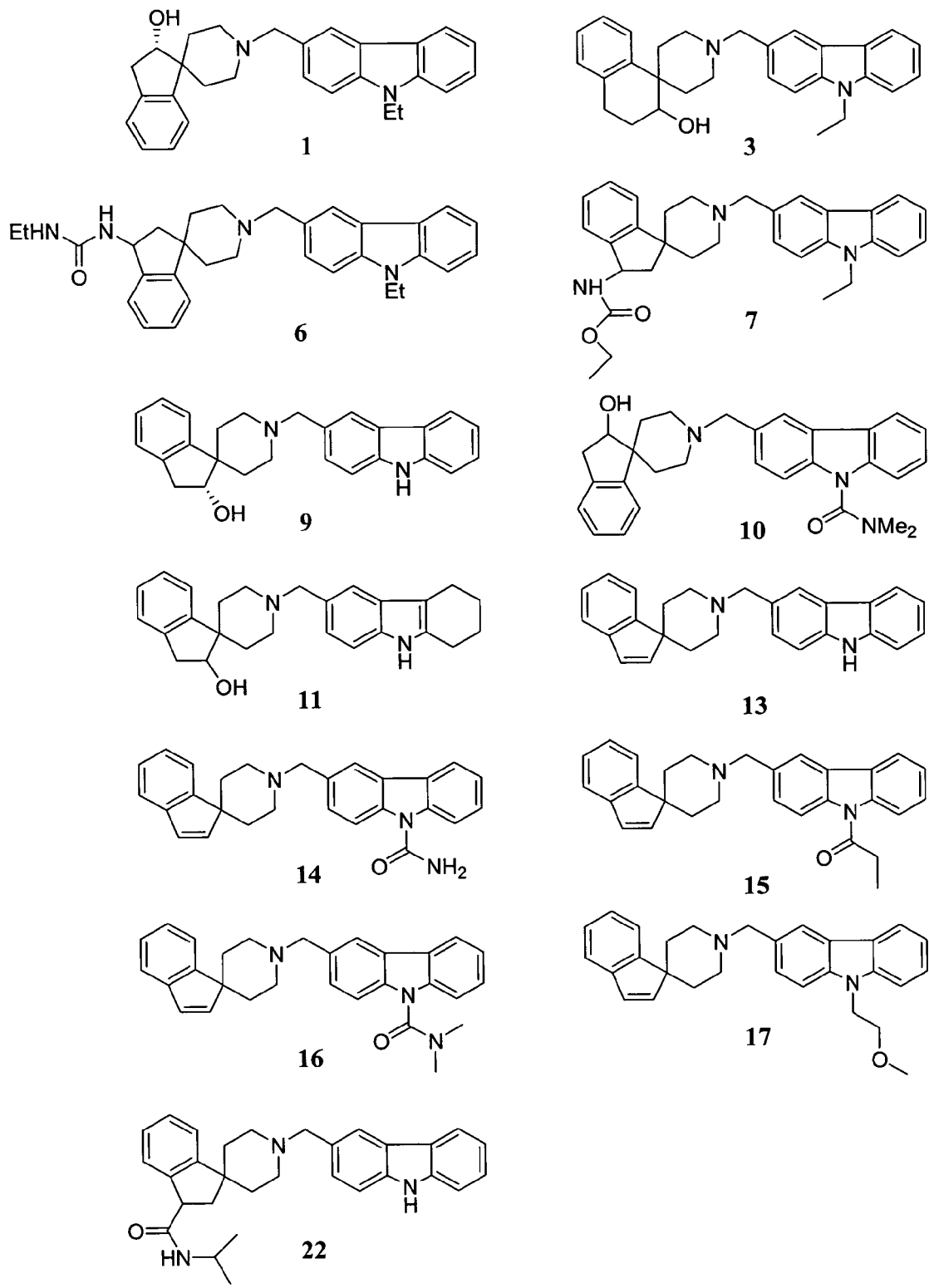

Efange, et al. "Spirovesamicols: Conformationally Restricted Analogs of 2-(4-Phenylpiperidine) Cyclohexanol (Vesamicol, AH5183) as Potential Modulators of Presynaptic Cholinergic Function" J. Med. Chem. (1994) 37: 2574-2582.

Efange, et al. "N-Hydroxyalkyl Derivatives of 3β-Phenyltropane and 1-Methylspirol {1H-Indoline 3,4'-Piperidine}: Vesamicol Analogues With Affinity for Monoamine Transporters", J. Med. Chem. (1997) 40: 3905-3914.

Gonzalez, et al., "alpha-Melanocyte-stimulating hormone (alpha-MSH) and melanin-concentrating hormone (MCH) modify monoaminergic levels in the preoptic area of the rat" *Peptides* (1997) 18:387-392.

Hashigaki, et al. "Synthesis and Structure-Activity Relationship of Spiro [Isochroman-Piperidine] Analogs for Inhibition of Histamine Release. IV", Chem Pharm. Bull. (1984) 32(9): 3561-3568.

Hawes, et al., "The melanin-concentrating hormone receptor couples to multiple G proteins to activate diverse intracellular signaling pathways" *Endocrinology*.(2000) 141: 4524-4532.

Hervieu, et al. "Similarities in cellular expression and functions of melanin-concentrating hormone and atrial natriuretic factor in the rat digestive tract", *Endocrinology* (1996) 137: 561-571.

Hill, et al., "Molecular cloning and functional characterization of MCH2, a novel human MCH receptor" *J. Biol Chem* (2001) 276(23)20125-20129.

Jezova, et al., "Rat melanin-concentrating hormone stimulates adrenocorticotropin secretion: evidence for a site of action in brain regions protected by the blood-brain barrier" *Endocrinology*.(1992) 130:1024-1029.

Mclamon, et al. "The Actions of L-687,384, a σ Receptor Ligand, on NMDA-Induced Currents in Cultured Rat Hippocampal Pyramidal Neurons" Neurosci Letter. (1994), 174(2): 181-184.

Miller, et al. "Alpha-MSH and MCH Are Functional Antagonists in a CNS Auditory Gating Paradigm", *Peptides* (1993) 14: 431-440.

Mori, et al., "Cloning of a novel G protein-coupled receptor, SLT, a subtype of the melanin-concentrating hormone receptor" *Biochem. Biophys. Res. Commun.* (2001) 283:1013-1018.

Parkes, et al., "Contrasting actions of melanin-concentrating hormone and neuropeptide-E-I on posterior pituitary function" *Ann N Y Acad Sci.* (1993) 680:588-90.

Qu, et al., "A role for melanin-concentrating hormone in the central regulation of feeding behaviour" *Naturet*.(1996) 380:243-247.

Rodriguez, et al. "Cloning and molecular characterization of the novel human melanin-concentrating hormone receptor MCH2", *Mol. Pharmacol.* (2001) 60(4): 632-639.

Rossi, et al., "Melanin-concentrating hormone acutely stimulates feeding, but chronic administration has no effect on body weight" *Endocrinology* (1997) 138:351-355.

Sailer, et al., "Identification and characterization of a second melanin-concentrating hormone receptor, MCH-2R." *Proc. Natl. Acad. Sci.* .(2001)98: 7564-7569.

Saito, et al. "Molecular characterization of the melanin-concentrating-hormone receptor", *Nature*(1999) 400: 265-269.

Saito, et al., "Melanin-concentrating hormone receptor: an orphan receptor fits the key" *Trends Endocrinol. Metab.* (2000) 11(8): 299-303.

Shimada, et al., "Mice Lacking melanin-concentrating hormone are Hypophagic and Lean", *Nature* (1998) 396: 670-674.

Wang, et al. "Identification and pharmacological characterization of a novel human melanin-concentrating hormone receptor, mch-r2", *J. Biol Chem.*, (2001) 276(37):34664-34670.

31

32

33

34

PIPERIDINE DERIVATIVES

The present application is entitled to and claims the benefit under 35 U.S.C. § 119(e) of U.S. Provisional Application No. 60/413,335, filed Sep. 24, 2002, which application is hereby incorporated by reference in its entirety.

1. FIELD OF THE INVENTION

The present invention relates to compounds and compositions useful in the treatment of conditions and disorders associated with, for example, energy metabolism, feeding behavior and other neuronal functions.

2. BACKGROUND OF THE INVENTION

G-protein coupled receptors play important roles in diverse signaling processes, including those involved with sensory and hormonal signal transduction. Eating disorders, which represent a major health concern throughout the world, have been linked to GPCR regulation. On the one hand, disorders such as obesity, the excess deposition of fat in the subcutaneous tissues, manifest themselves by an increase in body weight. Individuals who are obese often have, or are susceptible to, medical abnormalities including respiratory difficulties, cardiovascular disease, diabetes and hypertension. On the other hand, disorders like cachexia, the general lack of nutrition and wasting associated with chronic disease and/or emotional disturbance, are associated with a decrease in body weight.

The neuropeptide melanin-concentrating hormone (MCH), a cyclic hypothalamic peptide involved in the regulation of several functions in the brain, has previously been found to be a major regulator of feeding behavior and energy homeostasis (Qu et al. (1996) *Nature* 380:243–247; Rossi et al. (1997) *Endocrinology* 138:351–355; Shimada et al. (1998) *Nature* 396:670–674). It has previously been determined that MCH is the natural ligand for the 353-amino acid orphan G-protein-coupled-receptor (GPCR) termed SLC-1 (also known as GPR24). Subsequent to this determination, SLC-1, which is sequentially homologous to the somatostatin receptors, is frequently referred to as melanin-concentrating hormone receptor (MCH receptor, MCHR or MCHR1) (see Chambers et al. (1999) *Nature* 400:261–265; Saito et al. (1999) *Nature* 400:265–269; and Saito et al. (2000) *Trends Endocrinol. Metab.* 11(8):299–303).

MCHR1 has been shown to couple with $G_i$, $G_o$ and $G_q$ proteins (Saito et al. (2000) *Trends Endocrinol. Metab.* 11(8):299–303; Hawes et al. (2000) *Endocrinology* 141:4524–4532). Moreover, analysis of the tissue localization of MCHR1 indicates that it is expressed in those regions of the brain involved in olfactory learning and reinforcement. The cumulative data suggest that modulators of MCHR1 should have an effect on neuronal regulation of food intake (see Saito et al. (1999) *Nature* 400:265–269).

Compelling evidence exists that MCH is involved in regulation of feeding behavior. First, intracerebral administration of MCH in rats resulted in stimulation of feeding. Next, mRNA corresponding to the MCH precursor is upregulated in the hypothalamus of genetically obese mice and of fasted animals. Finally, mice deficient in MCH are leaner and have a decreased food intake relative to normal mice.

MCH has also been reported to be involved in the regulation or modulation of other physiological processes, including regulation of the hypothalamus-pituitary-adrenal axis (Jezova et al. (1992) *Endocrinology* 130:1024–1029), modulation of water and electrolyte fluxes in the gastrointestinal tract (Hervieu et al. (1996) *Endocrinology* 137:561–571), stimulation of oxytocin secretion (Parkes et al. (1993) in *Melanotropic Peptides*, eds. Eberle, A. & Vaudry, H., New York Academy of Sciences, NY, pp. 558), regulation of sensory processing (Miller et al. (1993) *Peptides* 14:431–440) and modulation of the activity of monoaminergic systems (Gonzalez et al. (1997) *Peptides* 18:387–392).

MCH is believed to exert its activity by binding to an MCH receptor, resulting in the mobilization of intracellular calcium and a concomitant reduction in cAMP levels (see Chambers et al. (1999) *Nature* 400:261–265 and Shimada et al. (1998) *Nature* 396:670–674). MCH also activates inwardly rectifying potassium channels (Bachner et al. (1999) *FEBS Lett.* 457(3):522–524).

Recently, an additional GPCR for MCH, designated MCHR2 (also known as MCH-2R, MCH2, $MCH_2$, SLT) has been identified (An et al. (2001) *Proc. Natl. Acad. Sci.* 98:7576–7581, Sailer et al. (2001) *Proc. Natl. Acad. Sci.* 98:7564–7569, Hill et al. (2001) *J. Biol. Chem.* 276(23):20125–20129, Wang et al. (2001) *J. Biol. Chem.* 276(37):34664–34670, Mori et al. (2001) *Biochem. Biophys. Res. Commun.* 283:1013–1018, Rodriguez et al. (2001) *Mol. Pharmacol.* 60(4):632–639). Protein sequence analysis indicates that MCHR2 has only 36% overall homology to MCHR1, but analysis of the tissue localization of MCHR2 indicates that its expression pattern is similar to that of MCHR1. Both receptors are expressed in regions of the brain, including the hypothalamus, and MCHR2 has been detected in other tissues that have been reported to express MCHR1, including adipose tissue and pituitary. In contrast to MCHR1, MCHR2 has been shown to couple primarily to $G_q$ protein.

While the similar expression patterns suggest that both MCHR1 and MCHR2 are important in processes regulated by MCH, such as regulation of feeding behavior and energy homeostasis, the differences in G protein coupling suggest that MCHR2 may have a role in diverse processes, such as fluid balance, behavioral responses, learning and processes regulated by ligands other than MCH.

The discovery of small molecules that modulate the function of MCHR2 is useful for the study of physiological processes mediated by MCHR2 and the development of therapeutic agents to treat conditions and disorders associated with processes mediated by MCHR2. In this application we describe novel compounds which display such desirable activity.

3. SUMMARY OF THE INVENTION

The present invention provides piperidine derivatives useful for treating or preventing conditions and disorders associated with energy metabolism, feeding behavior and neurologic function.

Certain compounds of the invention have the general formula:

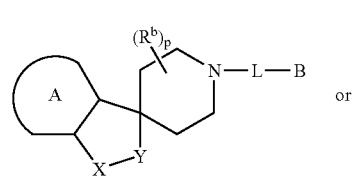

I or

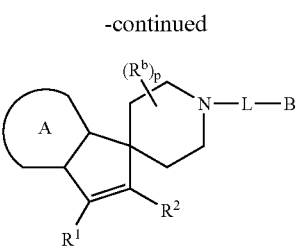

wherein A represents a substituted or unsubstituted ring selected from the group consisting of an aromatic ring, a 5- or 6-membered heteroaromatic ring, a 5- or 6-membered cycloalkane ring and a 5- or 6-membered heterocycloalkane ring; B represents cyclo($C_5$–$C_8$)alkyl, heterocyclo($C_5$–$C_8$)alkyl, cyclo($C_5$–$C_8$)alkenyl, heterocyclo($C_5$–$C_8$)alkenyl, aryl or heteroaryl; L represents ($C_1$–$C_4$)alkylene; X and Y independently represent a divalent linkage selected from ($C_1$–$C_2$)alkylene, ($C_1$–$C_2$)alkylene-$OR^3$, ($C_1$–$C_2$)alkylene-$N(R^3)COR^4$, ($C_1$–$C_2$)alkylene-$C(O)NR^3R^4$, ($C_1$–$C_2$)alkylene-$N(R^3)CO_2R^4$, ($C_1$–$C_2$)alkylene-$N(R^3)C(O)N(R^4)(R^5)$, ($C_1$–$C_2$)alkylene-C(O), O, C(O), $N(R^3)$, $C(O)N(R^3)$, $S(O)_k$ and $SO_2N(R^3)$; the subscript k is an integer of from 0 to 2; $R^1$ and $R^2$ are independently H, ($C_1$–$C_4$)alkyl, ($C_2$–$C_8$)alkenyl, ($C_2$–$C_8$)alkynyl, ($C_1$–$C_8$)heteroalkyl, aryl, aryl($C_1$–$C_4$)alkyl, $NR^6C(O)R^5$, $C(O)R^5$ or $NR^5C(O)NR^6$; each $R^b$ is selected from ($C_1$–$C_4$)alkyl, aryl, $OR^7$, $C(O)R^7$ and $C(O)NR^7R^8$ and the subscript p is an integer of from 0 to 4.

$R^3$ and $R^4$ are independently selected from H, ($C_1$–$C_8$) alkyl, hetero($C_1$–$C_8$)alkyl, aryl, aryl($C_1$–$C_4$)alkyl, C(O)R', $CO_2R'$ and C(O)NR'R"; $R^5$ and $R^6$ are independently H, ($C_1$–$C_8$)alkyl, ($C_1$–$C_8$)heteroalkyl, aryl($C_1$–$C_4$)alkyl or aryl; $R^7$ and $R^8$ are independently H, ($C_1$–$C_8$)alkyl, ($C_1$–$C_8$) heteroalkyl, aryl($C_1$–$C_4$)alkyl, or aryl and, optionally, $R^7$ and $R^8$ may be combined with the nitrogen to which each is attached to form a 5-, 6- or 7-membered ring; and R' and R" are independently selected from the group consisting of H, ($C_1$–$C_8$)alkyl, aryl and aryl($C_1$–$C_4$)alkyl.

In compounds of formula I, X and Y are not both O, $N(R^3)$, $S(O)_k$ or $SO_2N(R^3)$.

The invention also provides compounds of formula (VII):

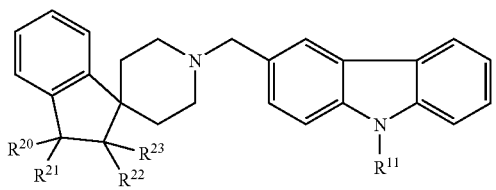

wherein $R^{20}$ and $R^{23}$ independently represent H or $OR^3$; $R^{21}$ and $R^{22}$ independently represent H, $OR^3$, $N(R^3)COR^4$, $C(O)NR^3R^4$, $N(R^3)CO_2R^4$, $N(R^3)C(O)N(R^4)R^5$, $N(R^3)R^4$, $C(O)N(R^3)R^4$, $N(R^3)C(O)R^4$, $(CH_2)C(O)N(R^3)(R^4)$, $(CH_2)CO_2R^3$, or ($C_1$–$C_4$)alkyl; $R^{11}$ represents H, ($C_1$–$C_4$)alkyl, ($C_2$–$C_8$)alkenyl, ($C_2$–$C_8$)alkynyl, ($C_1$–$C_8$)heteroalkyl, aryl, aryl($C_1$–$C_4$)alkyl, heteroaryl, heteroaryl($C_1$–$C_4$)alkyl, ($C_3$–$C_8$)cycloalkyl, ($C_5$–$C_8$)cycloalkenyl, ($C_3$–$C_8$)cycloalkyl-alkyl, ($C_3$–$C_8$)cycloheteroalkyl, ($C_3$–$C_8$)cycloheteroalkyl-alkyl, $C(O)R^{12}$, $CO_2R^{12}$, $C(O)NR^{12}R^{13}$, $S(O)_kR^{12}$ or $S(O)_kNR^{12}R^{13}$; $R^{12}$ and $R^{13}$ independently represent H, ($C_1$–$C_8$)alkyl, ($C_1$–$C_8$)heteroalkyl, aryl($C_1$–$C_4$)alkyl or aryl; $R^3$ and $R^4$ independently represent H, ($C_1$–$C_8$)alkyl, hetero ($C_1$–$C_8$)alkyl, aryl, aryl($C_1$–$C_4$)alkyl, C(O)R', $CO_2R'$ or C(O)NR'R"; and R', R" and R'" are independently selected from the group consisting of H, ($C_1$–$C_8$)alkyl, aryl and aryl($C_1$–$C_4$)alkyl.

In a preferred embodiment, $R^{20}$ and $R^{23}$ each represent H, $R^{22}$ represents OH, and $R^{21}$ represents $N(R^3)C(O)R^4$. In another preferred embodiment, $R^{20}$ represents OH, and $R^{22}$ and $R^{23}$ each represent H, and $R^{21}$ represents $C_2$ alkyl. In yet another preferred embodiment, $R^{20}$, $R^{22}$, and $R^{23}$ each represent H and $R^{21}$ represents $N(R^3)C(O)R^4$. In still another preferred embodiment, $R^{21}$, $R^{22}$, and $R^{23}$ each represent H and $R^{21}$ represents $(CH_2)CO_2R^3$. In yet another preferred embodiment, $R^{20}$, $R^{22}$, and $R^{23}$ each represent H and $R^{21}$ represents $(CH_2)C(O)N(R^3)(R^4)$.

The invention also provides compounds useful for treating or preventing conditions and disorders associated with energy metabolism, feeding behavior and neurologic function having the general formula (III):

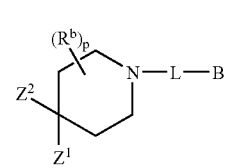

wherein B represents cyclo($C_5$–$C_8$)alkyl, heterocyclo ($C_5$–$C_8$)alkyl, cyclo($C_5$–$C_8$)alkenyl, heterocyclo($C_5$–$C_8$) alkenyl, aryl or heteroaryl; L is ($C_1$–$C_4$)alkylene; $Z^1$ represents $C(O)NR^9R^{10}$, $OR^9$, $NC(O)R^9$, $NSO_2R^9$ or $NR^9R^{10}$; $Z^2$ is aryl or heteroaryl; each $R^b$ is ($C_1$–$C_4$)alkyl, aryl, $OR^7$, $C(O)R^7$ or $C(O)NR^7R^8$ and the subscript p is an integer of from 0 to 4.

$R^7$ and $R^8$ are independently selected from the group consisting of H, ($C_1$–$C_8$)alkyl, hetero($C_1$–$C_8$)alkyl, aryl, alkoxy, thioalkoxy and aryl($C_1$–$C_4$)alkyl; $R^9$ and $R^{10}$ are independently selected from the group consisting of H, ($C_1$–$C_8$)alkyl, ($C_1$–$C_8$)heteroalkyl, aryl($C_1$–$C_4$)alkyl and aryl and, optionally, $R^9$ and $R^{10}$ may be combined with the nitrogen atom to which they are attached to form a 5-, 6- or 7-membered ring.

Unless otherwise indicated, the compounds provided in the above formulas are meant to include all pharmaceutically acceptable salts, hydrates, solvates and prodrugs thereof.

The present invention also provides pharmaceutical compositions comprising a compound of the invention and a pharmaceutically acceptable carrier or excipient.

The present invention further provides methods for treating or preventing a condition or disorder selected from the group consisting of obesity, diabetes, anorexia nervosa, bulimia, pain, cancers, asthma, Parkinson's disease, acute heart failure, congestive heart failure, hypotension, hypertension, urinary retention, osteoporosis, angina pectoris, myocardial infarction, stroke, ulcers, allergies, benign prostatic hypertrophy, migraine, vomiting, anxiety, schizophrenia, manic depression, depression, delirium, dementia, severe mental retardation, Huntington's disease, Gilles de la Tourette's Syndrome, Syndrome X, insulin resistance, hyperglycemia, hyperuricemia, hyperinsulinemia, hypercholesterolemia, hyperlipidemia, dyslipidemia, mixed dyslipidemia, hypertriglyceridemia, male sexual dysfunction, female sexual dysfunction, fever, inflammation, rheumatoid arthritis, atherosclerosis, Alzheimer's disease, epilepsy, autism, bipolar disorder, neuroses, substance abuse, generalized anxiety disorder, panic disorder, obsessive-compulsive disorder, posttraumatic stress syndrome, gall bladder disease, sleep apnea syndrome, narcolepsy, insomnia, Shy-Drager Syndrome, multiple sclerosis, dystonia, coronary artery disease, cardiomyopathy, cachexia, osteoarthritis, Prader-Willi Syndrome, hypothyroidism, hypogonadism, hyperprolactinemia, traumatic brain injury, ischemic reperfusion injury, aneurysm, spinal cord injury and Pickwick Syndrome, comprising administering to a subject in need thereof a therapeutically effective amount of a compound of the invention.

The present invention also provides methods for treating or preventing a condition or disorder mediated by MCHR2.

The present invention further provides methods for modulating MCHR2 comprising contacting a cell with a compound of the invention.

Other objects, features and advantages of the present invention will become apparent to those skilled in the art from the following description and claims.

4. BRIEF DESCRIPTION OF THE DRAWINGS

Figure 2:
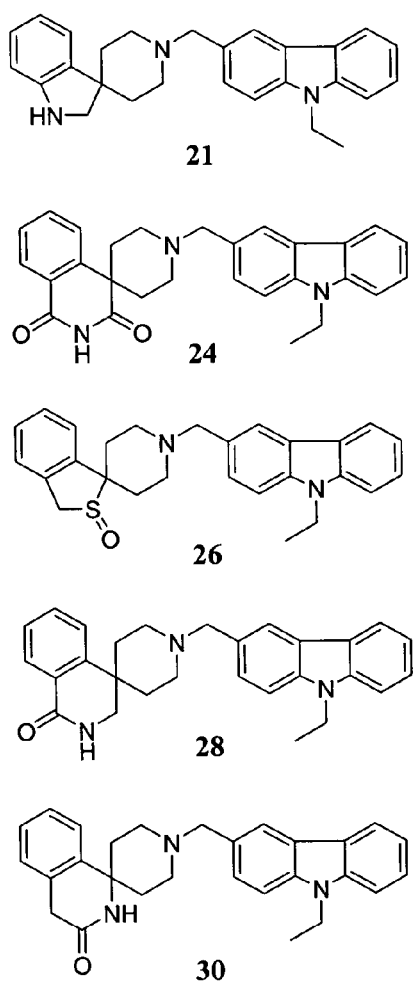
Figure 3:
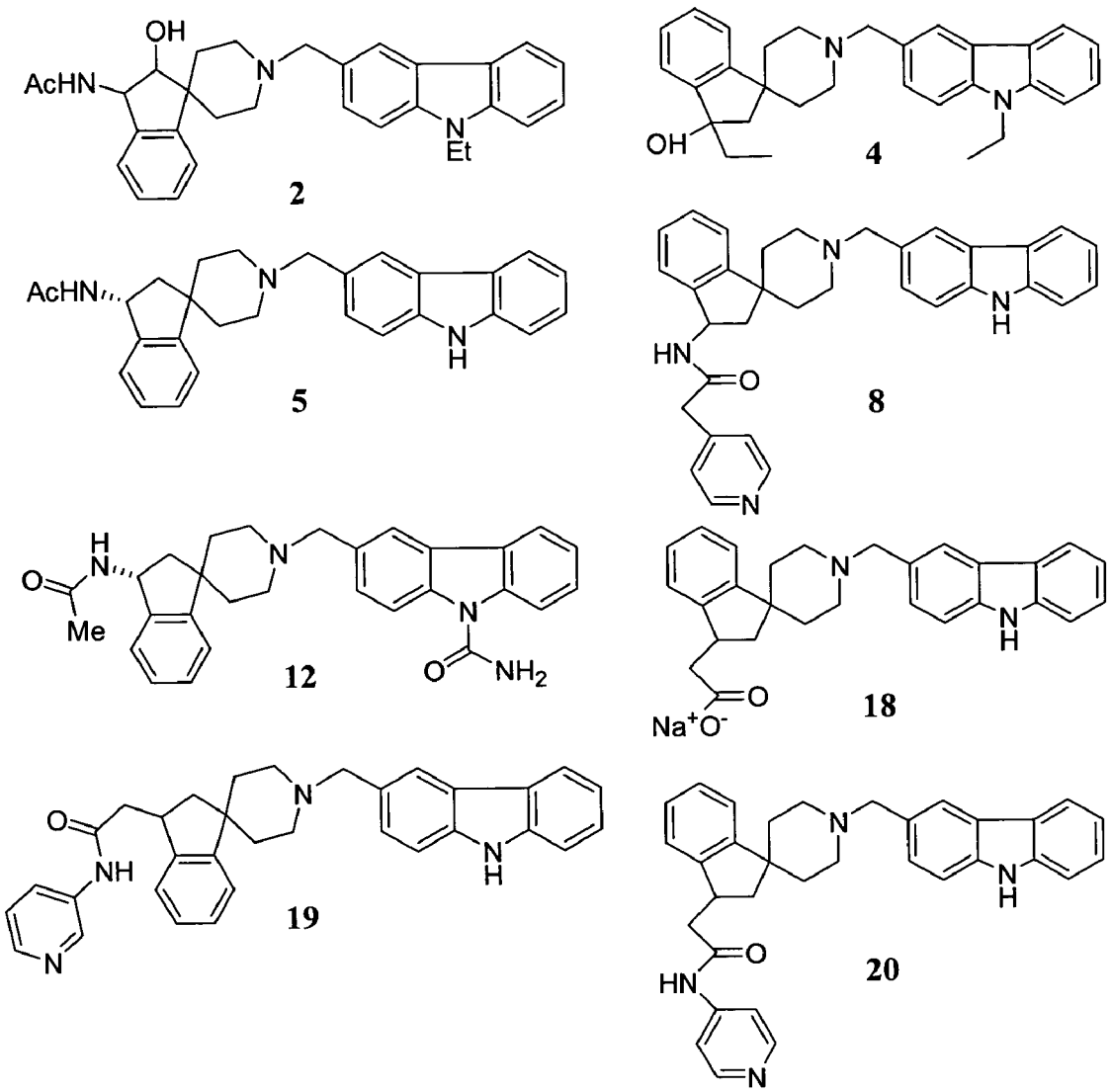

FIG. 1 provides exemplary structures of compounds of the invention;

FIG. 2 provides exemplary structures of compounds of the invention;

FIG. 3 provides exemplary structures of compounds of the invention; and

Figure 4:
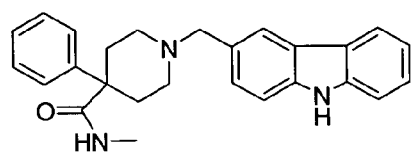
Figure 4:
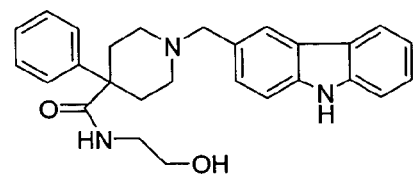
Figure 4:
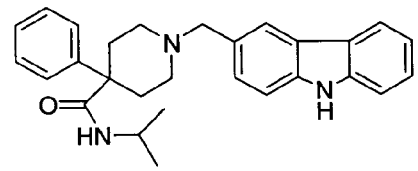
Figure 4:
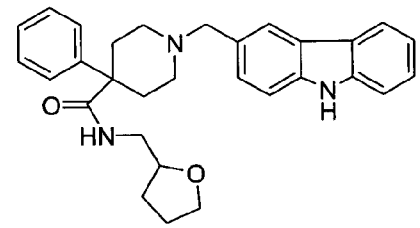

FIG. 4 provides exemplary structures of compounds of the invention.

5. DETAILED DESCRIPTION OF THE INVENTION

5.1. Abbreviations and Definitions

The abbreviations used herein are conventional, unless otherwise defined.

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of MCHR2. Modulation, as described herein, includes the inhibition or activation of MCHR2, either directly or indirectly. Inhibitors are compounds that, e.g., bind to, partially or totally block stimulation, decrease, prevent, delay activation, inactivate, desensitize, or downregulate signal transduction, e.g., antagonists. Activators are compounds that, e.g., bind to, stimulate, increase, open, activate, facilitate, enhance activation, sensitize or upregulate signal transduction, e.g., agonists.

As used herein, "diabetes" refers to type I diabetes mellitus (juvenile onset diabetes, insulin dependent-diabetes mellitus or IDDM) or type II diabetes mellitus (non-insulin-dependent diabetes mellitus or NIDDM), preferably, type II diabetes.

As used herein, "Syndrome X" refers to a collection of abnormalities including hyperinsulinemia, obesity, elevated levels of triglycerides, uric acid, fibrinogen, small dense LDL particles and plasminogen activator inhibitor 1 (PAI-1), and decreased levels of HDL cholesterol. Syndrome X is further meant to include metabolic syndrome.

As used herein, the term "obesity" refers to the excessive accumulation of body fat. Obesity may have genetic, environmental (e.g., expending less energy than is consumed) and regulatory determinants. Obesity includes exogenous, hyperinsulinar, hyperplasmic, hypothyroid, hypothalamic, symptomatic, infantile, upper body, alimentary, hypogonadal, simple and central obesity, hypophyseal adiposity and hyperphagia. Cardiovascular disorders, such as hypertension and coronary artery disease, and metabolic disorders, such as hyperlidemia and diabetes, are commonly associated with obesity.

As used herein, the terms "eating disorder", "feeding disorder" and the like refer to an emotional and/or behavioral disturbance associated with an excessive decrease in body weight and/or inappropriate efforts to avoid weight gain, e.g., fasting, self-induced vomiting, laxative or diuretic abuse. Depression is commonly associated with eating disorders. Exemplary eating disorders include anorexia nervosa and bulimia.

As used herein, the term "anxiety disorder" refers to an emotional and/or behavioral disturbance characterized by persistent and pervasive worry or restlessness, tension or irritability about, e.g., health, work, money or family, for no clear reason. An anxiety disorder may be accompanied by tachycardia or dyspnea. Exemplary anxiety disorders include anxiety, generalized anxiety disorder, panic attacks, panic disorder and obsessive-compulsive disorder.

The "subject" is defined herein to include animals such as mammals, including, but not limited to, primates (e.g., humans), cows, sheep, goats, horses, dogs, cats, and the like. In preferred embodiments, the subject is a human.

The term "MCHR2" refers to the melanin-concentrating hormone receptor protein 2 (MCHR2) or a variant thereof, unless otherwise stated. MCHR2 variants include proteins substantially homologous to native MCHR2, i.e., proteins having one or more naturally or non-naturally occurring amino acid deletions, insertions or substitutions (e.g., MCHR2 derivatives, homologs and fragments). The amino acid sequence of an MCHR2 variant preferably is at least about 80% identical to a native MCHR2, more preferably at least about 90% identical, and most preferably at least about 95% identical. Human MCHR2 includes the melanin-concentrating hormone receptor proteins described in An et al. (2001) *Proc. Natl. Acad. Sci.* 98:7576–7581, Sailer et al. (2001) *Proc. Natl. Acad. Sci.* 98:7564–7569, Hill et al. (2001) *J. Biol. Chem.* 276(23):20125–20129, Wang et al. (2001) *J. Biol. Chem.* 276(37):34664–34670, Mori et al. (2001) *Biochem. Biophys. Res. Commun.* 283:1013–1018 and Rodriguez et al. (2001) *Mol. Pharmacol.* 60(4):632–639, incorporated by reference herein, and assigned GenBank Accession Nos. AB060151, AF399937 and AF347063.

As used herein, the term "condition or disorder responsive to MCHR2 modulation" refers to a condition or disorder associated with inappropriate, e.g., less than or greater than normal, MCHR2 activity and at least partially responsive to or affected by MCHR2 modulation (e.g., an MCHR2 inhibitor or antagonist results in some improvement in patient well-being in at least some subjects suffering from said condition or disorder). Inappropriate MCHR2 functional activity might arise as the result of MCHR2 expression in cells which normally do not express MCHR2 decreased MCHR2 expression (leading to, e.g., metabolic disorders) or increased MCHR2 expression. A condition or disorder responsive to MCHR2 modulation includes a condition or disorder characterized by inappropriate MCHR2 activity, or an "MCHR2-mediated condition or disorder". An MCHR2-mediated condition or disorder may be completely or partially mediated by inappropriate MCHR2 activity.

The term "alkyl", by itself or as part of another substituent, means, unless otherwise stated, a straight or branched chain, or cyclic hydrocarbon radical, or combination thereof, which may be fully saturated, mono- or polyunsaturated and can include di- and multi-valent radicals, having the number of carbon atoms designated (i.e., $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene."

The term "alkylene" by itself or as part of another substituent means a divalent radical derived from an alkane, as exemplified by —$CH_2CH_2CH_2CH_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—$SO_2$—$CH_3$, —CH═CH—O—$CH_3$, —Si($CH_3$)$_3$, —$CH_2$—CH═N—$OCH_3$, and —CH═CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 1-pyrrolidinyl, 2-pyrrolidinyl, 3-pyrrolidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl. For example, the term "halo ($C_1$–$C_4$)alkyl" is meant to include trifluoromethyl, 2,2,2-trifluoroethyl, 4-chlorobutyl, 3-bromopropyl, and the like.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1H-indazolyl, carbazolyl, α-carbolinyl, β-carbolinyl, γ-carbolinyl, 1-isoquinolyl, 5-isoquinolyl, 2-quinoxalinyl, 5-quinoxalinyl, 3-quinolyl and 6-quinolyl. Substituents for each of the above noted aryl ring systems are selected from the group of acceptable substituents described below.

The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

As used herein, each of the above terms (e.g., "alkyl," "heteroalkyl" and "aryl") is meant to include both substituted and unsubstituted forms of the indicated radical, unless otherwise stated. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', ═O, ═NR', ═N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"$CO_2$R', —NH—C($NH_2$)═NH, —NR'C($NH_2$)═NH, —NH—C ($NH_2$)=NR', —S(O)R', —$SO_2$R', —$SO_2$NR'R", —CN and —$NO_2$ in a number ranging from zero to (2N+1), where N is the total number of carbon atoms in such radical. R', R" and R'" each independently refer to H, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl groups are varied and are selected from: -halogen, —OR', —OC(O)R', —NR'R", —SR', —R', —CN, —$NO_2$, —$CO_2$R', —C(O)NR'R", —C(O)R', —OC(O)NR'R", —NR"C(O)R', —NR"$CO_2$R', —NR'—C(O)NR"R'", —NH—C(NH2)=NH, —NR'C($NH_2$)=NH, —NH—C($NH_2$)=NR', —S(O)R', —$SO_2$R', —$SO_2$NR'R", —$N_3$, —CH(Ph)$_2$, perfluoro($C_1$–$C_4$)alkoxy, perfluoro($C_1$–$C_4$)alkyl, halo($C_1$–$C_8$)alkyl, ($C_1$–$C_4$)alkoxy, aryl($C_1$–$C_4$)alkyl, —S(O)NR'R", ($C_4$–$C_8$)cycloalkyl, ($C_5$–$C_8$)cycloalkenyl, aryl heteroaryl, ($C_1$–$C_8$)alkyl, ($C_2$–$C_8$)alkenyl, ($C_2$–$C_8$)alkynyl, ($C_1$–$C_8$)heteroalkyl, aryl, heteroaryl, heteroaryl($C_1$–$C_4$)alkyl, ($C_3$–$C_8$)cycloalkyl, ($C_5$–$C_8$)cycloalkenyl, ($C_3$–$C_8$)cycloalkyl-alkyl, ($C_3$–$C_8$)cycloheteroalkyl, ($C_3$–$C_8$)cycloheteroalkyl-alkyl, N(R")S(O)R', N(R', and OCO$_2$R'; in a number ranging from zero to the total number of open valences on the aromatic ring system; and where R', R" and R'" are independently selected from H, ($C_1$–$C_8$)alkyl and heteroalkyl, aryl, (aryl)-($C_1$–$C_4$)alkyl, and (unsubstituted aryl)oxy-($C_1$–$C_4$)alkyl.

Two of the substituents on adjacent atoms of the aryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl ring may optionally be replaced with a substituent of the formula -A-(CH$_2$)$_r$-B-, wherein A and B are independently —CH$_2$—, —O—, —NH—, —S—, —S(O)—, —SO$_2$—, —SO$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —SO$_2$—, or —SO$_2$NR'—. The substituent R' in —NR'— and —SO$_2$NR — is selected from H or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic and the like. Also included are salts of amino acids such as arginate and the like, and salts of organic acids like glucuronic or galactunoric acids and the like (see, for example, Berge, S. M., et al. (1977) *J. Pharm. Sci.* 66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, enantiomers, diastereomers, geometric isomers and individual isomers are all intended to be encompassed within the scope of the present invention. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatagraphic means well known in the art, and subsequent recovery of the pure enantiomers.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are intended to be encompassed within the scope of the present invention.

5.2. Embodiments of the Invention

Human MCHR2 is highly expressed in brain, in particular in cortical regions. MCHR1 is more broadly expressed in the brain and is detected at moderate levels in peripheral tissues, such as the eye, skeletal muscle, the tongue and the pituitary gland. Evidence suggests that MCHR2 is involved in feeding and neuroendocrine modulation, e.g., fluid balance, behavioral responses, learning and other physiological processes regulated by MCH or ligands other than MCH.

Compounds useful for the treatment or prevention of conditions and disorders related to or associated with MCHR2 in animals, particularly humans, are provided herein. While the precise understanding of the mechanism by which the compounds of the invention have an effect on physiological processes regulated by MCH or other MCHR2 ligands is not required to practice the invention, the compounds are believed to modulate the function, or activity, of MCHR2. Thus, the compounds are useful in, for example, the treatment or prevention of conditions and disorders associated with physiological processes regulated by an MCHR2 ligand. Such conditions and disorders include, but are not limited to obesity, diabetes, eating disorders, such as anorexia nervosa and bulimia; pain; cancers; asthma; Parkinson's disease; acute heart failure; congestive heart failure; hypotension; hypertension; urinary retention; osteoporosis; angina pectoris; myocardial infarction; stroke; ulcers; allergies; benign prostatic hypertrophy; migraine; vomiting; psychotic and neurologic disorders, including anxiety, schizophrenia, manic depression, depression, delirium, dementia and severe mental retardation; dyskinesias, such as Huntington's disease or Gilles de la Tourette's Syndrome; Syndrome X, insulin resistance, hyperglycemia, hyperuricemia, hyperinsulinemia, hypercholesterolemia, hyperlipidemia, dyslipidemia, mixed dyslipidemia and hypertriglyceridemia; male and female sexual dysfunction, including impotence, loss of libido and erectile dysfunction; fever; inflammation; rheumatoid arthritis; atherosclerosis; Alzheimer's disease; epilepsy; autism; bipolar disorder; neuroses; substance abuse; generalized anxiety disorder; panic disorder; obsessive-compulsive disorder; posttraumatic stress syndrome; gall bladder disease; sleep disorders, such as sleep apnea syndrome; narcolepsy and insomnia; Shy-Drager Syndrome; multiple sclerosis; dystonia; cardiovascular disease, e.g., coronary artery disease and cardiomyopathy; cachexia; osteoarthritis; Prader-Willi Syndrome; hypothyroidism; hypogonadism; hyperprolactinemia; traumatic brain injury; ischemic reperfusion injury; aneurysm; spinal cord injury and Pickwick Syndrome.

The invention encompasses novel compounds, novel pharmaceutical compositions and/or novel methods of use. While some compounds disclosed herein may be available from commercial sources, the pharmaceutical compositions or methods of using these compounds are novel. Unless otherwise indicated, it is to be understood that the invention includes those compounds that are novel, as well as pharmaceutical compositions, various methods (e.g., methods of treating or preventing certain MCHR2-mediated diseases or conditions), and the like which include both the novel compounds of the invention and compounds that are commercially available.

5.2.1. Compounds

In one aspect, the invention provides compounds of formula:

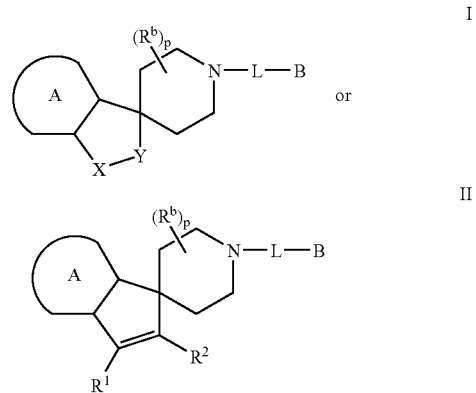

or a pharmaceutically acceptable salt, hydrate, solvate and prodrug thereof.

In formulas I and II, A represents a substituted or unsubstituted ring selected from the group consisting of an aromatic ring, a 5- or 6-membered heteroaromatic ring, a 5- or 6-membered cycloalkane ring and a 5- or 6-membered heterocycloalkane ring.

B is cyclo($C_5$–$C_8$)alkyl, heterocyclo($C_5$–$C_8$)alkyl, cyclo($C_5$–$C_8$)alkenyl, heterocyclo($C_5$–$C_8$)alkenyl, aryl or heteroaryl. Examples of particular values for B are phenyl, naphthyl, pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, carbazolyl, indazolyl, carbolinyl, dibenzofuryl, dibenzothienyl, phenoxazinyl, phenothiazinyl, phenoxathiinyl, isoquinolyl, quinoxalinyl and quinolyl.

In a preferred embodiment, B contains from 1 to 3 nitrogen atoms. Exemplary values for B are indolyl, carbazolyl and carbolinyl. In a particularly preferred embodiment, B is 3-carbazolyl. In another particularly preferred embodiment, B is 5-indolyl.

L is ($C_1$–$C_4$)alkylene.

X and Y are independently a divalent linkage selected from ($C_1$–$C_2$)alkylene, ($C_1$–$C_2$)alkylene-$OR^3$, ($C_1$–$C_2$)alkylene-$N(R^3)COR^4$, ($C_1$–$C_2$)alkylene-C(O)$NR^3R^4$, ($C_1$–$C_2$)alkylene-$N(R^3)CO_2R^4$, ($C_1$–$C_2$)alkylene-$N(R^3)C(O)N(R^4)R^5$, ($C_1$–$C_2$)alkylene-C(O), O, C(O), N($R^3$), C(O)N($R^3$), S(O)$_k$ and SO$_2$N($R^3$), wherein $R^3$ and $R^4$ are independently selected from the group consisting of H, $(C_1-C_8)$alkyl, hetero$(C_1-C_8)$alkyl, aryl, aryl$(C_1-C_4)$alkyl, C(O)R', CO$_2$R and C(O)NR'R", wherein R' and R" are independently selected from the group consisting of H, $(C_1-C_8)$alkyl, aryl and aryl$(C_1-C_4)$alkyl, and the subscript k is an integer from 0 to 2, provided that X and Y are not both O, N(R$^3$), S(O)$_k$ or SO$_2$N(R$^3$).

In one preferred embodiment, X or Y is $(C_1-C_2)$alkylene-OH. In another preferred embodiment, Y is CH—OH. In another preferred embodiment, X is $(C_1-C_2)$alkylene-N(R$^3$)COR$^4$. In another preferred embodiment, X is CH—N(R$^3$)COR$^4$ and Y is CH—OH. In still another preferred embodiment, X is N(R$^3$) and Y is C(O). In another preferred embodiment, X is $(C_1-C_2)$alkylene, N(R$^3$), C(O)N(R$^3$) or S(O)$_k$ and Y is $(C_1-C_2)$alkylene. In another preferred embodiment, X is $(C_1-C_2)$alkylene and Y is C(O), N(R$^3$), C(O)N(R$^3$) or S(O)$_k$.

R$^1$ and R$^2$ are independently H, $(C_1-C_4)$alkyl, $(C_2-C_8)$alkenyl, $(C_2-C_8)$alkynyl, $(C_1-C_8)$heteroalkyl, aryl, aryl$(C_1-C_4)$alkyl, NR$^6$C(O)R$^5$, C(O)R$^5$ or NR$^5$C(O)NR$^6$, wherein R$^5$ and R$^6$ are independently H, $(C_1-C_8)$alkyl, $(C_1-C_8)$heteroalkyl, aryl$(C_1-C_4)$alkyl or aryl. In a preferred embodiment, R$^1$ and R$^2$ are H.

Each R$^b$ is selected from $(C_1-C_4)$alkyl, aryl, OR$^7$, C(O)R$^7$ and C(O)NR$^7$R$^8$, wherein R$^7$ and R$^8$ are independently H, $(C_1-C_8)$alkyl, $(C_1-C_8)$heteroalkyl, aryl$(C_1-C_4)$alkyl or aryl, and, optionally, R$^7$ and R$^9$ may be combined with the nitrogen to which each is attached to form a 5-, 6- or 7-membered ring. The subscript p is an integer of from 0 to 4. In a preferred embodiment, the subscript p is 0.

In formula I, A is fused to the ring system containing X and Y via adjacent carbon atoms. In formula II, A is fused to the cycloalkene ring system via adjacent carbon atoms. Embodiments represented by formulas I and II can be appreciated by replacing the ring system containing X and Y or the cycloalkene ring system with a wavy line. Thus, the A-fused ring system can be represented as:

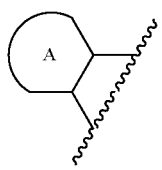

For example, the A-fused ring system is meant to include the following (including substituted versions thereof), wherein A is selected from those embodiments shown as:

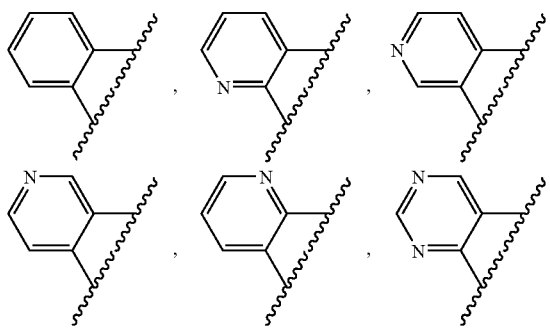

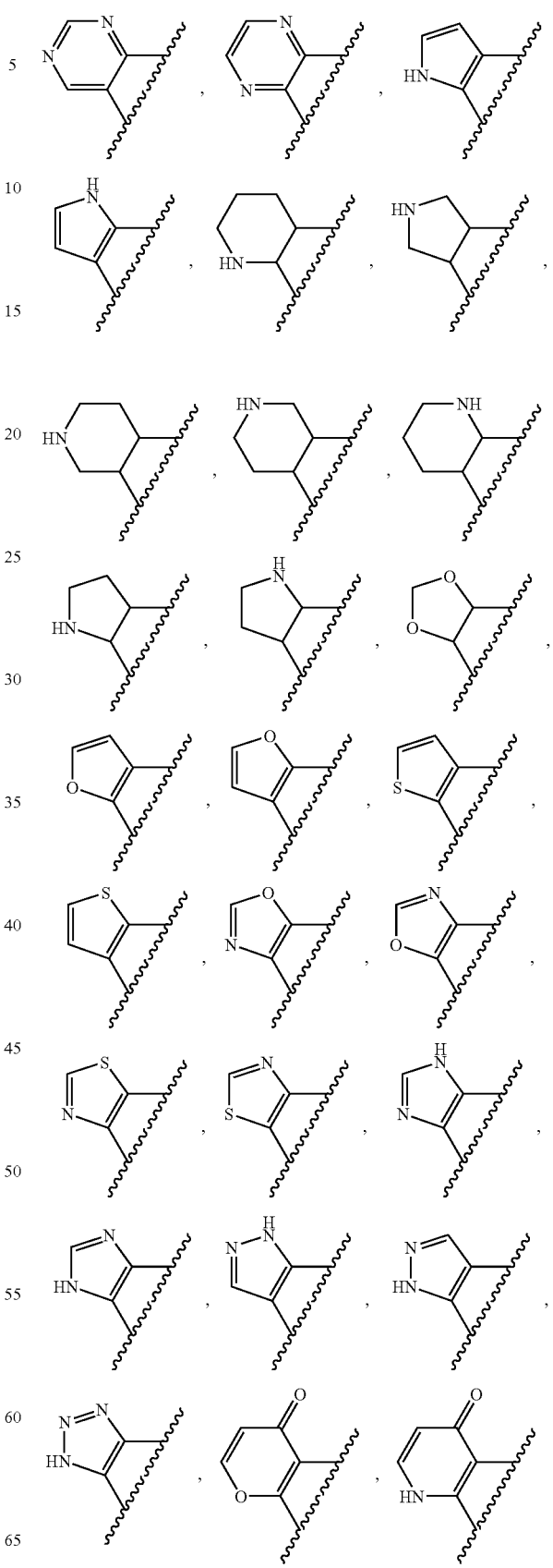

-continued

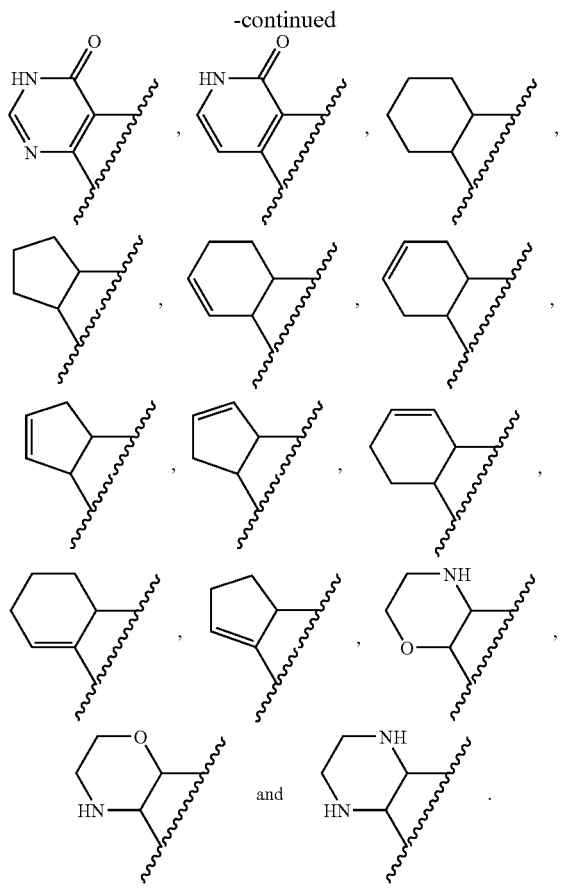

In a preferred embodiment, A is benzene, cyclohexane or cyclohexene. In a particularly preferred embodiment, A is benzene.

Within these embodiments are several groups of preferred embodiments, described below.

In one group of preferred embodiments, A is benzene and B is 3-carbazolyl.

One group of preferred embodiments is represented by formula (IV):

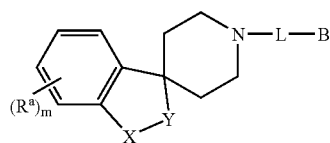

IV

In this formula, each $R^a$ is independently halogen, halo$(C_1-C_4)$alkyl, $(C_1-C_4)$alkoxy, aryl$(C_1-C_4)$alkyl, $OC(O)R^{17}$, $NR^{17}R^{18}$, $SR^{17}$, cyano, nitro, $CO_2R^{17}$, $CONR^{17}R^{18}$, $C(O)R^{17}$, $OC(O)NR^{17}R^{18}$, $NR^{18}C(O)R^{17}$, $NR^{18}CO_2R^{17}$, $NR^{19}C(O)NR^{17}R^{18}$, $S(O)_kR^{17}$, $S(O)_kNR^{17}R^{18}$, $N_3$, $(C_4-C_8)$cycloalkyl, $(C_5-C_8)$cycloalkenyl, aryl or heteroaryl, wherein $R^{17}$, $R^{18}$ and $R^{19}$ are independently selected from the group consisting of H, $(C_1-C_8)$alkyl, $(C_1-C_8)$heteroalkyl, aryl $(C_1-C_4)$alkyl and aryl, and the subscript k is an integer of from 1 to 2.

The subscript m is an integer of from 0 to 4.

B, L, X and Y have the meanings and preferred groupings provided above.

Another group of preferred embodiments is represented by the formula (V):

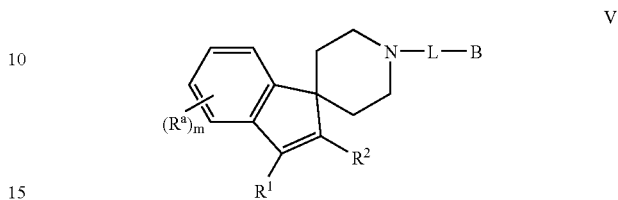

V wherein B, L, $R^1$, $R^2$, $R^a$ and the subscript m have the meanings and preferred groupings provided above.

Another group of preferred embodiments is represented by the formulas:

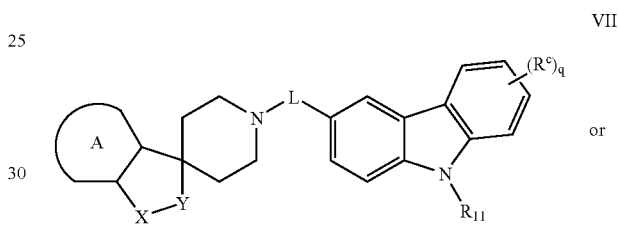

VII or

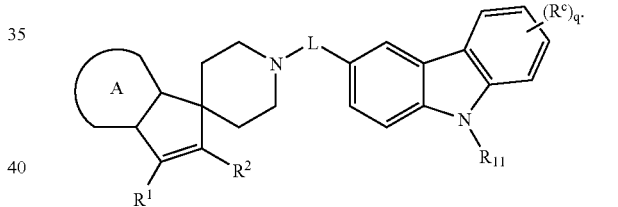

VIII

In formulas VII and VIII, $R^{11}$ is selected from the group consisting of H, $(C_1-C_4)$alkyl, $(C_2-C_8)$alkenyl, $(C_2-C_8)$alkynyl, $(C_1-C_8)$heteroalkyl, aryl, aryl$(C_1-C_4)$alkyl, heteroaryl, heteroaryl$(C_1-C_4)$alkyl, $(C_3-C_8)$cycloalkyl, $(C_5-C_8)$cycloalkenyl, $(C_3-C_8)$cycloalkyl-alkyl, $(C_3-C_8)$cycloheteroalkyl, $(C_3-C_8)$cycloheteroalkyl-alkyl, $C(O)R^{12}$, $CO_2R^2$, $C(O)NR^{12}R^3$, $S(O)_kR^{12}$ and $S(O)_kNR^{12}R^{13}$, wherein $R^{12}$ are $R^{13}$ are independently selected from the group consisting of H, $(C_1-C_8)$alkyl, $(C_1-C_8)$heteroalkyl, aryl$(C_1-C_4)$alkyl and aryl and the subscript k is an integer of from 1 to 2.

Each $R^c$ is independently selected from the group consisting of $(C_1-C_8)$alkyl, $(C_2-C_8)$alkenyl, $(C_2-C_8)$alkynyl, $(C_1-C_8)$heteroalkyl, halo$(C_1-C_8)$alkyl, halogen, CN, $NO_2$, $OR^{14}$, $SR^{14}$, $NR^{14}R^{15}$, $(C_3-C_8)$cycloalkyl, $(C_5-C_8)$cycloalkenyl, $(C_3-C_8)$cycloalkyl-alkyl, $(C_3-C_8)$cycloheteroalkyl, $(C_3-C_8)$cycloheteroalkyl-alkyl, $C(O)R^{14}$, $CO_2R^{14}$, $C(O)NR^{14}R^{15}$, aryl, aryl$(C_1-C_4)$alkyl, heteroaryl, heteroaryl$(C_1-C_4)$alkyl, $S(O)_kR^{14}$, $S(O)_kNR^{14}R^{15}$, $N(R^{15})S(O)_kR^{14}$, $OC(O)R^{14}$, $OCO_2R^{14}$, $OC(O)NR^{14}R^{15}$, $N(R^{16})C(O)NR^{14}R^{15}$, $N(R^{15})C(O)R^{14}$ and $N(R^{15})CO_2R^{14}$, wherein $R^{14}$, $R^{15}$ and $R^{16}$ are independently selected from the group consisting of H, $(C_1-C_8)$alkyl, $(C_1-C_8)$heteroalkyl, aryl $(C_1-C_4)$alkyl and aryl, and the subscript k is an integer of from 1 to 2. Optionally, any two adjacent $R^c$ groups may be combined to form a fused aryl ring or $(C_5–C_8)$cycloalkyl ring.

The subscript q is an integer of from 0 to 7.

Still another group of preferred embodiments is represented by the formulas:

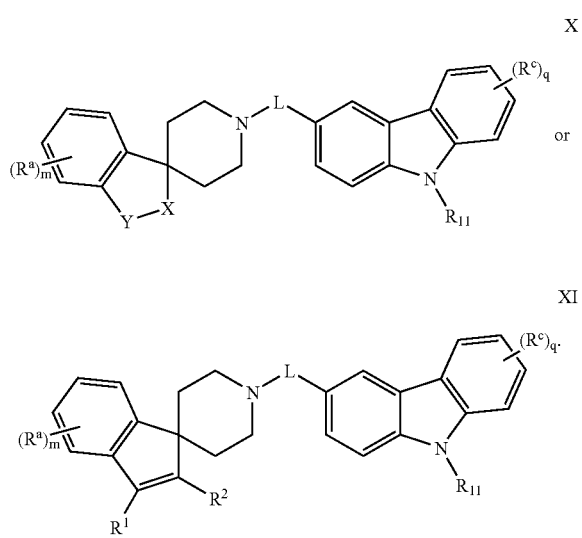

In formulas X and XI, each $R^a$ is independently halogen, halo$(C_1–C_4)$alkyl, $(C_1–C_4)$alkoxy, aryl$(C_1–C_4)$alkyl, OC(O)$R^{17}$, $NR^{17}R^{19}$, $SR^{17}$, cyano, nitro, $CO_2R^{17}$, $CONR^{17}R^{18}$, C(O)$R^{17}$, OC(O)$NR^{17}R^{18}$, $NR^{18}C(O)R^{17}$, $NR^{18}CO_2R^{17}$, $NR^{19}C(O)NR^{17}R^{15}$, $S(O)_kR^7$, $S(O)_kNR^{17}R^{15}$, $N_3$, $(C_4–C_8)$cycloalkyl, $(C_5–C_8)$cycloalkenyl, aryl or heteroaryl, wherein $R^{17}$, $R^{18}$ and $R^{19}$ are independently H, $(C_1–C_8)$alkyl, $(C_1–C_8)$heteroalkyl, aryl$(C_1–C_4)$alkyl or aryl, and the subscript k is an integer of from 1 to 2.

The subscript m is an integer of from 0 to 4.

X, Y, $R^{11}$, $R^c$ and the subscript q have the meanings and preferred groupings provided above.

Within each group of preferred embodiments, methylene is a preferred group for L.

Particularly preferred are those embodiments that combine preferred groups. Accordingly, one group of particularly preferred embodiments is represented by formula (Xa):

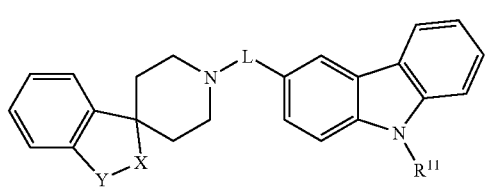

wherein L is methylene and X and Y are independently selected from $(C_1–C_2)$alkylene, $(C_1–C_2)$alkylene-$OR^3$, $(C_1–C_2)$alkylene-$N(R^3)COR^4$, $(C^1–C_2)$alkylene-C(O)$NR^3R^4$ and $(C_1–C_2)$alkylene-$N(R^3)$C(O)$N(R^4)R^5$. In one particularly preferred embodiment, L is methylene and X or Y is $(C_1–C_2)$alkylene-OH. In another particularly preferred embodiment, L is methylene and Y is CH—OH. In another particularly preferred embodiment, L is methylene and X is $(C_1–C_2)$alkylene-$N(R^3)COR^4$. In another particularly preferred embodiment, L is methylene and X is CH—N($R^3$)$COR^4$ and Y is CH—OH. In still another particularly preferred embodiment, L is methylene and X is N($R^3$) and Y is C(O). In another particularly preferred embodiment, L is methylene and X is $(C_1–C_2)$alkylene, N($R^3$), C(O)N($R^3$) or $S(O)_k$ and Y is $(C_1–C_2)$alkylene. In another particularly preferred embodiment, L is methylene and X is $(C_1–C_2)$alkylene and Y is C(O), N($R^3$), C(O)N($R^3$) or $S(O)_k$.

Another group of particularly preferred embodiments is represented by formula Xa, wherein L is methylene; X and Y are independently selected from $(C_1–C_2)$alkylene, $(C_1–C_2)$alkylene-$OR^3$, $(C_1–C_2)$alkylene-$N(R^3)COR^4$, $(C^1–C_2)$alkylene-C(O)$NR^3R^4$ and $(C_1–C_2)$alkylene-$N(R^3)$C(O)$N(R^4)$; and $R^{11}$ is selected from H, $(C_1–C_4)$alkyl, C(O)$NR^{12}R^{13}$, $S(O)_kR^{12}$ and $S(O)_kNR^{12}R^{13}$. In one particularly preferred embodiment, L is unsubstituted methylene (—$CH_2$—); X and Y are independently selected from —$CH_2$—, —CH(OH, —CH—(NHC(O)$R^4$), —H—($CH_2C(O)NHR^4R^5$) and —CH—(NHC(O)$NR^4R^5$)—; and $R^{11}$ is selected from H, ethyl and C(O)$NR^{12}R^3$.

Exemplary compounds of the invention are provided in FIG. 1, FIG. 2, FIG. 3, and FIG. 4.

The invention also provides compounds of formula (VII):

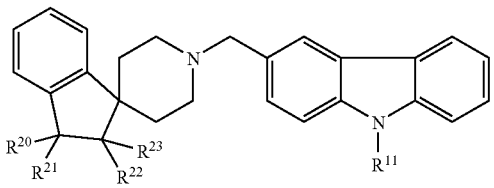

wherein $R^{20}$ and $R^{23}$ independently represent H or $OR^3$; $R^{21}$ and $R^{22}$ independently represent H, $OR^3$, N($R^3$)$COR^4$, C(O)$NR^3R^4$, N($R^3$)$CO_2R^4$, N($R^3$)C(O)N($R^4$)$R^5$, N($R^3$)$R^4$, C(O)N($R^3$)$R^4$, N($R^3$)C(O)$R^4$, ($CH_2$)C(O)N($R^3$)($R^4$), ($CH_2$)$CO_2R^3$, or $(C_1–C_4)$alkyl; $R^{11}$ represents H, $(C_1–C_4)$alkyl, $(C_2–C_8)$alkenyl, $(C_2–C_8)$alkynyl, $(C_1–C_8)$heteroalkyl, aryl, aryl$(C_1–C_4)$alkyl, heteroaryl, heteroaryl$(C_1–C_4)$alkyl, $(C_3–C_8)$cycloalkyl, $(C_5–C_8)$cycloalkenyl, $(C_3–C_8)$cycloalkyl-alkyl, $(C_3–C_8)$cycloheteroalkyl, $(C_3–C_8)$cycloheteroalkyl-alkyl, C(O)$R^2$, $CO_2R^{12}$, C(O)$NR^{12}R^{13}$, $S(O)_kR^{12}$ or $S(O)_kNR^{12}R^{13}$; $R^{12}$ and $R^{13}$ independently represent H, $(C_1–C_8)$alkyl, $(C_1–C_8)$heteroalkyl, aryl$(C_1–C_4)$alkyl or aryl; $R^3$ and $R^4$ independently represent H, $(C_1–C_8)$alkyl, hetero$(C_1–C_8)$alkyl, aryl, aryl$(C_1–C_4)$alkyl, C(O)R', $CO_2$R' or C(O)NR'R''; and R', R and R''' are independently selected from the group consisting of H, $(C_1–C_8)$alkyl, aryl and aryl$(C_1–C_4)$alkyl.

In a preferred embodiment, $R^{20}$ and $R^{23}$ each represent H, $R^{22}$ represents OH, and $R^{21}$ represents N($R^3$)C(O)$R^4$. In another preferred embodiment, $R^{20}$ represents OH, and $R^{22}$ and $R^{23}$ each represent H, and $R^{21}$ represents $C_2$ alkyl. In yet another preferred embodiment, $R^{20}$, $R^{22}$, and $R^{23}$ each represent H and $R^{21}$ represents N($R^3$)C(O)$R^4$. In still another preferred embodiment, $R^{20}$, $R^{22}$, and $R^{23}$ each represent H and $R^{21}$ represents ($CH_2$)$CO_2R^3$. In yet another preferred embodiment, $R^{20}$, $R^{22}$, and $R^{23}$ each represent H and $R^{21}$ represents ($CH_2$)C(O)N($R^3$)($R^4$).

The invention also provides compounds of formula (III):

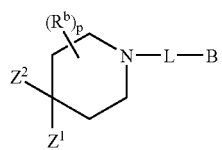

III or a pharmaceutically acceptable salt, hydrate, solvate and prodrug thereof.

In formula III, B is cyclo($C_5$–$C_8$)alkyl, heterocyclo ($C_5$–$C_8$)alkyl, cyclo($C_5$–$C_8$)alkenyl, heterocyclo($C_5$–$C_8$) alkenyl, aryl or heteroaryl. Examples of particular values for B are phenyl, naphthyl, pyrrolyl, pyrazolyl, imidazolyl, pyrazinyl, oxazolyl, isoxazolyl, thiazolyl, furyl, thienyl, pyridyl, pyrimidyl, benzothiazolyl, purinyl, benzimidazolyl, indolyl, carbazolyl, indazolyl, carbolinyl, dibenzofuryl, dibenzothienyl, phenoxazinyl, phenothiazinyl, phenoxathiinyl, isoquinolyl, quinoxalinyl or quinolyl.

In a preferred embodiment, B contains from 1 to 3 nitrogen atoms. Exemplary values for B are indolyl, carbazolyl and carbolinyl. In a particularly preferred embodiment, B is 3-carbazolyl. In another particularly preferred embodiment, B is 5-indolyl.

L is ($C_1$–$C_4$)alkylene.

$Z^1$ is ($C_1$–$C_8$)alkyl, ($C_1$–$C_4$)alkyl-$OR^9$, ($C_1$–$C_4$)alkyl-$NR^9COR^{10}$, ($C_1$–$C_4$)alkyl-$NR^9CONR^9R^{10}$, cycloakyl, heterocycloakyl, $C(O)NR^9R^{10}$, $OR^9$, $NC(O)R^9$, $NSO_2R^9$ or $NR^9R^{10}$, wherein $R^9$ and $R^{10}$ are independently selected from the group consisting of H, ($C_1$–$C_8$)alkyl, ($C_1$–$C_8$) heteroalkyl, aryl($C_1$–$C_4$)alkyl and aryl and, optionally, $R^9$ and $R^{10}$ may be combined with the nitrogen atom to which they are attached to form a 5-, 6- or 7-membered ring.

$Z^2$ is aryl or heteroaryl. In a preferred embodiment, $Z^2$ is phenyl.

Each $R^b$ is ($C_1$–$C_4$)alkyl, aryl, $OR^7$, $C(O)R^7$ or $C(O)NR^7R^8$, wherein $R^7$ and $R^8$ are independently selected from the group consisting of H, ($C_1$–$C_8$)alkyl, hetero($C_1$–$C_8$) alkyl, aryl, alkoxy, thioalkoxy and aryl($C_1$–$C_4$)alkyl, and the subscript p is an integer from 0 to 4. In a preferred embodiment, the subscript p is 0.

In one group of preferred embodiments, B is 3-carbazolyl.

Another group of preferred embodiments is represented by the formula-(VI):

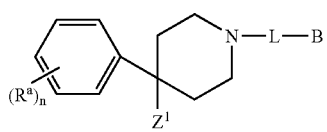

VI

In this formula, each $R^a$ is independently halogen, halo ($C_1$–$C_4$)alkyl, ($C_1$–$C_4$)alkoxy, aryl($C_1$–$C_4$)alkyl, $OC(O)R^{17}$, $NR^{17}R^{18}$, $SR^{17}$, cyano, nitro, $CO_2R^{17}$, $CONR^{17}R^1$, $C(O)R^{17}$, $OC(O)NR^{17}R^{18}$, $NR^{18}C(O)R^{17}$, $NR^{18}CO_2R^{17}$, $NR^{19}C(O)NR^{17}R^{18}$, $S(O)_kR^{17}$, $S(O)_kNR^{17}R^{18}$, $N_3$, ($C_4$–$C_8$)cycloalkyl, ($C_5$–$C_8$)cycloalkenyl, aryl or heteroaryl, wherein $R^{17}$, $R^{18}$ and $R^{19}$ are independently selected from the group consisting of H, ($C_1$–$C_8$)alkyl, ($C_1$–$C_8$)heteroalkyl, aryl ($C_1$–$C_4$)alkyl and aryl, and each subscript k is an integer from 1 to 2. Optionally, any two adjacent $R^a$ groups may be combined to form a fused aryl or ($C_5$–$C_8$)cycloalkyl ring.

The subscript n is an integer of from 0 to 5.

B, L and $Z^1$, have the meanings and preferred groupings provided above.

Another group of preferred embodiments is represented by the formula (IX):

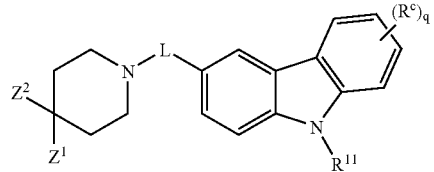

IX

In this formula, $R^{11}$ is H, ($C_1$–$C_4$)alkyl, ($C_2$–$C_8$)alkenyl, ($C_2$–$C_8$)alkynyl, ($C_1$–$C_8$)heteroalkyl, aryl, aryl($C_1$–$C_4$) alkyl, heteroaryl, heteroaryl($C_1$–$C_4$)alkyl, ($C_3$–$C_8$)cycloalkyl, ($C_5$–$C_8$)cycloalkenyl, ($C_3$–$C_8$)cycloalkylalkyl, ($C_3$–$C_8$)cycloheteroalkyl, ($C_3$–$C_8$) cycloheteroalkyl-alkyl, $C(O)R^{12}$, $CO_2R^{12}$, $C(O)NR^{12}R^{13}$, $S(O)_kR^{12}$ or $S(O)_kNR^{12}R^{13}$, wherein the subscript k is an integer of from 1 to 2.

Each $R^c$ is independently selected from the group consisting of ($C_1$–$C_8$)alkyl, ($C_2$–$C_8$)alkenyl, ($C_2$–$C_8$)alkynyl, ($C_1$–$C_8$)heteroalkyl, halo($C_1$–$C_8$)alkyl, halogen, CN, $NO_2$, $OR^{14}$, $NR^{14}R^{15}$, ($C_3$–$C_8$)cycloalkyl, ($C_5$–$C_8$)cycloalkenyl, ($C_3$–$C_8$)cycloalkyl-alkyl, ($C_3$–$C_8$)cycloheteroalkyl, ($C_3$–$C_8$) cycloheteroalkyl-alkyl, $C(O)R^{14}$, $CO_2R^{14}$, $C(O)NR^{14}R^{15}$, aryl, aryl($C_1$–$C_4$)alkyl, heteroaryl, heteroaryl($C_1$–$C_4$)alkyl, $S(O)_kR^{14}$, $S(O)_kNR^{14}R^{15}$, $N(R^{15})S(O)_kR^{14}$, $OC(O)R^{14}$, $OCO_2R^{14}$, $OC(O)N^{14}R^{15}$, $N(R^{16})C(O)NR^{14}R^{15}$, $N(R^{15})C(O)R^{14}$ and $N(R^{15})CO_2R^{14}$, wherein $R^{12}$, $R^{13}$, $R^{14}$, $R^{15}$ and $R^{16}$ are independently H, ($C_1$–$C_8$)alkyl, ($C_1$–$C_8$)heteroalkyl, aryl($C_1$–$C_4$)alkyl or aryl, and the subscript k is an integer from 1 to 2. Optionally, any two adjacent $R^c$ groups may be combined to form a fused aryl or ($C_5$–$C_8$)cycloalkyl ring.

The subscript q is an integer of from 0 to 7.

L, $Z^1$ and $Z^2$ have the meanings and preferred groupings provided above.

Another group of preferred embodiments is represented by the formula (XII):

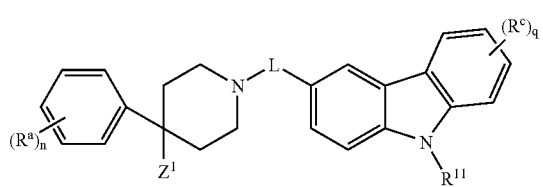

XII

In this formula, $R^a$, L, $Z^1$, $R^{11}$, $R^c$ and the subscripts n and q have the meanings and preferred groupings provided above.

Within each group of preferred embodiments, methylene is a preferred group for L.

Compounds contemplated by the invention include, but are not limited to, the exemplary compounds provided herein.

5.2.2. Compositions

In another aspect, the present invention provides pharmaceutical compositions comprising a compound of the invention, in combination with a pharmaceutically acceptable carrier or excipient. The subject compositions are useful for treating or preventing conditions and disorders mediated by MCHR2.

For preparing pharmaceutical compositions from the compounds of the invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from about 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

The compositions may be advantageously combined and/or used in combination with other agents useful in the treatment and/or prevention of obesity and complications thereof, diabetes, pain, cancers, Parkinson's disease, stroke, migraine, anxiety, schizophrenia, depression, atherosclerosis, Alzheimer's disease, epilepsy, multiple sclerosis and those pathologies noted above. In many instances, administration of the subject compounds or compositions in conjunction with these alternative therapeutic agents enhances the efficacy of such agents. Accordingly, in some instances, the present compounds, when combined or administered in combination with, e.g., anti-obesity agents, can be used in dosages which are less than the expected amounts when used alone, or less than the calculated amounts for combination therapy.

Other agents may be administered, by a route and in an amount commonly used therefor, simultaneously or sequentially with a compound of the present invention. When a compound of the present invention is used contemporaneously with one or more other drugs, in some cases a pharmaceutical composition containing such other drugs in addition to the compound of the present invention may be preferred. Accordingly, the pharmaceutical compositions of the present invention include those that also contain one or more other active ingredients, in addition to a compound of the invention.

Examples of therapeutic agents or active ingredients that may be combined with a compound of the invention, either administered separately or in the same pharmaceutical composition, include, but are not limited to: (a) VLA-4 antagonists, (b) corticosteroids, such as beclomethasone, methylprednisolone, betamethasone, prednisone, prenisolone, dexamethasone, fluticasone and hydrocortisone, and corticosteroid analogs such as budesonide; (c) immunosuppressants such as cyclosporine (cyclosporine A, Sandimmune®, Neoral®), tacrolimus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, terfenadine, loratadine, cetirizine, fexofenadine, descarboethoxyloratadine and the like; (e) non-steroidal anti-asthmatics such as β2-agonists (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafirlukast, montelukast, pranlukast, iralukast, pobilukast and SKB-106,203), leukotriene biosynthesis inhibitors (zileuton, BAY-1005); (f) nonsteroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine), the pyrazolones (e.g., apazone, bezpiperylon, feprazone, mofebutazone, oxyphenbutazone and phenylbutazone) and cyclooxygenase-2 (COX-2) inhibitors such as celecoxib (Celebrex®) and rofecoxib (Vioxx®); (g) inhibitors of phosphodiesterase type IV (PDE-IV); (h) opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; (i) cholesterol lowering agents such as HMG-CoA reductase inhibitors (e.g., lovastatin, simvastatin, pravastatin, fluvastatin, atorvastatin and other statins), bile acid sequestrants (e.g., cholestyramine, colestipol and dialkylaminoalkyl derivatives of a cross-linked dextran), vitamin $B_3$ (also known as nicotinic acid or niacin), vitamin $B_6$ (pyridoxine), vitamin $B_{12}$ (cyanocobalamin), fibric acid derivatives (gemfibrozil, clofibrate, fenofibrate and benzafibrate), probucol, nitroglycerin, inhibitors of cholesterol absorption (e.g., beta-sitosterol and acylCoA-cholesterol acyltransferase (ACAT) inhibitors, e.g., melinamide), HMG-CoA synthase inhibitors, squalene epoxidase inhibitors, squalene synthetase inhibitors; (j) anti-diabetic agents such as insulin or insulin mimetics, sulfonylureas (e.g., glyburide, meglinatide, tolbutamide and glipizide), biguamides, e.g., metformin (Glucophage®), α-glucosidase inhibitors (e.g., acarbose), thiazolidinedione compounds, e.g., rosiglitazone (Avandia®), troglitazone (Rezulin®), ciglitazone, pioglitazone (Actos®) and englitazone; (k) preparations of interferon beta (interferon β-1α, interferon β-1β); (1) TNF inhibitors, e.g., etanercept (Enbrel®) (m) multiple sclerosis therapeutic agents such as interferon β-1β (Betaseron®), interferon β-1α (Avonex®), azathioprine (Imurek®S, Imuran®), glatiramer acetate (Capoxone®), a glucocorticoid (e.g., prednisolone) and cyclophosphamide, (n) anti-obesity agents such as fenfluramine, dexfenfluramine, phentermine, sibutramine, gastrointestinal lipase inhibitors (e.g., orlistat), phenylpropanolamine, diethylprorion, mazindol, β3 adrenergic receptor agonists, leptin or derivatives thereof and neuropeptide Y antagonists (e.g., NPY5); (o) agents useful in the treatment of anxiety and/or mood disorders such as benzodiazepines (e.g., alprazolam, chlordiazepoxide, clonazepam, clorazepate, diazepam, lorazepam, oxazepam, and the like), heterocyclic antidepressants (e.g, amitriptyline, nortriptyline, imipramine, desipramine, doxepin, trimipramine, clomipramine, protryptyline, amoxapine and maprotiline), monoamine oxidase inhibitors (MAOIs) (e.g., phenelzine and tranylcypromine), serotonin reuptake inhibitors (SRIs), selective serotonin reuptake inhibitors (SSRIs) (e.g., fluoxetine, fluvoxamine, paroxetine and sertraline), serotonergic-noradrenergic antidepressants (e.g., venlafaxine), 5-HT2 antagonists (e.g., trazadone, nefazodone and mirtazapine) and catecholaminergic antidepressants (e.g., buproprion); (p) growth hormone secretagogues (e.g., MK-0677); (q) agents useful in the treatment of male and/or female sexual dysfunction, such as phophodiester V inhibitors (sildenafil) and α-2 adrenergic receptor antagonists; (r) hormone therapy (e.g., thyroxine, testosterone); (s) other MCHR antagonists, especially MCHR1 antagonists; (t) antineoplastic agents, such as DNA alkylating agents (e.g., mechlorethamine, chlorambucil, cyclophosphamide, melphalan and ifosfamide), antimetabolites (e.g., methotrexate, azathioprine, 6-mercaptopurine, 5-fluorouracil, cytarabine and gemcitabine), microtubule disruptors and/or spindle poisons (e.g., vinblastine, vincristine, vinorelbine, colchicine, nocodazole, paclitaxel, docetaxel, etoposide, irinotecan and topotecan,), DNA intercalators (e.g., doxorubicin, daunomycin, bleomycin, mitomycin, cisplatin and carboplatin), nitrosoureas (e.g., carmustine and lomustine), interferon, aspariginase and hormones (e.g., tamoxifen, leuoprolide, flutamide and megestrol acetate); (u) antithrombotic agents, such as thrombolytic agents (e.g., streptokinase, alteplase, anistreplase and reteplase), heparin, hirudin and warfarin derivatives, β-blockers (e.g., atenolol), β-adrenergic agonists (e.g., isoproterenol), ACE inhibitors, vasodilators (e.g., sodium nitroprusside, nicardipine hydrochloride, nitroglycerin and enaloprilat); (v) recombinant tissue plasminogen activator (tPA); (w) anticonvulsants (e.g., acetazolamide, carbamazepine, clonazepam, ethosuximide, fosphenyloin, gabapentin, lamotrigine, phenobarbital, phenyloin, primidone, topiramate and valproate); (x) antipsychotic drugs, such as chlorpromazine, fluphenazine, haloperidol, loxapine, mesoridazine, molindone, perphenazine, pimozide, thioridazine, thiothixene, trifluoperazine, clozapine, risperidone, olanzapine, quetiapine, sertindole and ziprasidone; (y) cholinesterase inhibitors, such as galantamine (Reminyl®), donepezil hydrochloride (Aricept®) and rivastigmine (Exelon®) and (z) anticholinergic agents (e.g., diphenhydramine, orphenadrine, amitriptyline, doxepin, imipramine, nortriptyline, benztropine, biperiden, ethopropazine, procyclidine and trihexyphenidyl), dopaminergic agents (e.g., carbidopa/levodopa, bromocriptine and pergolide), selegiline and amantadine; and prodrugs thereof.

The weight ratio of the compound of the present invention to the second active ingredient may be varied and will depend upon the effective dose of each ingredient. Generally, an effective dose of each will be used. Thus, for example, when a compound of the present invention is combined with, e.g., an anti-obesity agent, the weight ratio of the compound of the present invention to the anti-obesity agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

5.2.3. Methods of Use

In yet another aspect, the invention provides methods of treating or preventing a condition or disorder associated with energy metabolism, feeding behavior and neuronal functions described herein. In one group of embodiments, conditions or disorders, including chronic diseases, of humans or other species can be treated with inhibitors of MCHR2 function. These diseases or conditions include (1) inflammatory or allergic diseases such as systemic anaphylaxis and hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis and urticaria, (5) vasculitis, (6) spondyloarthropathies, (7) scleroderma, (8) asthma and respiratory allergic diseases such as allergic asthma, allergic rhinitis, allergic conjunctivitis, hypersensitivity lung diseases and the like, and (9) autoimmune diseases, such as arthritis (including rheumatoid and psoriatic), systemic lupus erythematosus, type I diabetes, glomerulonephritis and the like, (10) graft rejection (including allograft rejection and graft-v-host disease), (11) myositis, encephalitis, meningitis, hepatitis, nephritis, gall bladder disease, sepsis, sarcoidosis, allergic conjunctivitis, otitis, chronic obstructive pulmonary disease, sinusitis, Behcet's syndrome, gout, (12) metabolic disorders, such as obesity, type II diabetes, Syndrome X, insulin resistance, hypoglycemia, hyperuricemia, hyperinsulinemia, cachexia, hypercholesterolemia, hyperlipidemia, dyslipidemia, mixed dyslipidemia and hypertriglyceridemia, eating disorders, such as anorexia nervosa and bulimia, (13) fever, (14) cardiovascular disorders, such as acute heart failure, hypotension, hypertension, angina pectoris, myocardial infarction, cardiomyopathy, congestive heart failure, atherosclerosis, coronary artery disease, arteriosclerosis, restenosis and vascular stenosis, (15) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood and lymphatic system; (16) genitourinary disorders, such as urinary retention, urinary incontinence, benign prostatic hypertrophy, male and/or female sexual dysfunction and erectile dysfunction, (17) osteoporosis, osteoarthritis and Paget's disease, (18) gastrointestinal disorders, such as inflammatory bowel diseases (e.g., Crohn's disease, ulcerative colitis, ileitis and enteritis), gastritis, ulcers, nausea, pancreatitis and vomiting, (19) psychiatric disorders, such as anxiety disorders (e.g., panic disorder, panic attacks, obsessive-compulsive disorder, posttraumatic stress disorder, generalized anxiety disorder), mood disorders (e.g., depression, manic depression, major depressive disorder, bipolar disorder), schizophrenia and related disorders, compulsive behavior, aggressive behavior, neuroses and drug use and dependence, (20) endocrine disorders, such as Prader-Willi Syndrome, hypothyroidism, hypogonadism, and hyperprolactinemia, and (21) neurologic disorders, such as Alzheimer's disease, Parkinson's disease, Shy-Drager Syndrome, dyskinesias (e.g., Gilles de la Tourette's Syndrome, Huntington's disease, dystonia and the like), delirium, dementia, cognitive dysfunction or impairment, sleep disorders (e.g., insomnia, narcolepsy, sleep apnea syndrome and Pickwick Syndrome), epilepsy, severe mental retardation, cerebrovascular disease (e.g., traumatic brain injury, stroke, ischemic reperfusion injury, aneurysm), spinal cord injury, autism, pain, migraine, diabetic neuropathy and multiple sclerosis.

In one embodiment, the present methods are directed to the treatment or prevention of conditions or disorders selected from obesity, diabetes, anorexia nervosa, bulimia, pain, cancers, asthma, Parkinson's disease, acute heart failure, congestive heart failure, hypotension, hypertension, urinary retention, osteoporosis, angina pectoris, myocardial infarction, stroke, ulcers, allergies, benign prostatic hypertrophy, migraine, vomiting, anxiety, schizophrenia, manic depression, depression, delirium, dementia, severe mental retardation, Huntington's disease, Gilles de la Tourette's Syndrome, Syndrome X, insulin resistance, hyperglycemia, hyperuricemia, hyperinsulinemia, hypercholesterolemia, hyperlipidemia, dyslipidemia, mixed dyslipidemia, hypertriglyceridemia, male sexual dysfunction, female sexual dysfunction, fever, inflammation, rheumatoid arthritis, atherosclerosis, Alzheimer's disease, epilepsy, autism, bipolar disorder, neuroses, substance abuse, generalized anxiety disorder, panic disorder, obsessive-compulsive disorder, posttraumatic stress syndrome, gall bladder disease, sleep apnea syndrome, narcolepsy, insomnia, Shy-Drager Syndrome, multiple sclerosis, dystonia, coronary artery disease, cardiomyopathy, cachexia, osteoarthritis, Prader-Willi Syndrome, hypothyroidism, hypogonadism, hyperprolactinemia, traumatic brain injury, ischemic reperfusion injury, aneurysm, spinal cord injury and Pickwick Syndrome. The methods comprise administering to a subject in need thereof a therapeutically effective amount of a compound of the invention or a composition thereof.

In another embodiment, the presesnt methods are directed to the treatment or prevention of a condition or disorder that is responsive to MCHR2 modulation. The methods comprise administering to a subject in need thereof a therapeutically effective amount of a compound of the invention or a composition thereof.

In another embodiment, the presesnt methods are directed to the treatment or prevention of a condition or disorder that is mediated by MCHR2. The methods comprise administering to a subject in need thereof a therapeutically effective amount of a compound of the invention or a composition thereof.

In another aspect, the invention provides methods for modifying feeding behavior, comprising administering to a subject an amount of a compound of the invention or a composition thereof, effective to reduce or enhance food intake by the subject. Preferably, food intake is reduced or enhanced by at least 5%.

In another aspect, the invention provides methods for reducing body mass, comprising administering to a subject an amount of a compound of the invention or a composition thereof, effective to decrease the body mass of the subject. Preferably, the body mass of the subject is decreased by at least 5% of baseline. More preferably, the body mass of the subject is decreased by at least 10% of baseline.

In still another aspect, the invention provides methods of using a compound of the invention to modulate MCHR2. The methods comprise contacting a cell with a compound of the invention or a composition thereof.

The compounds of the invention can be prepared and administered in a wide variety of oral and parenteral dosage forms. Thus, the compounds of the present invention can be administered by injection, for example, intravenously, ICV, intracisternally, intramuscularly, intracutaneously, subcutaneously, intraduodenally or intraperitoneally. Also, the compounds described herein can be administered by inhalation, for example, intranasally. Additional, routes of administration include vaginal, rectal, sublingual or topical (e.g., transdermal). The compounds of the present invention may be formulated, alone or together, in suitable dosage unit formulations containing conventional non-toxic pharmaceutically acceptable carriers, adjuvants and vehicles appropriate for each route of administration. The present invention also contemplates administration of the compounds of the present invention in a depot formulation, in which the active ingredient is released over a defined time period.

In the treatment or prevention of conditions or disorders responsive to MCHR2 modulation, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

5.3. Preparation of the Compounds

The compounds of the invention can be synthesized generally via reductive amination of a substituted carbazole aldehyde with a spiroamine prepared according to methods described in, e.g., Efange et al. (1997) *J. Med. Chem.* 40:3905–3914, Kubata et al. (1998) *Chem. Pharm. Bull.* 46(2):351–354, Kubata et al. (1998) *Chem. Pharm. Bull.* 46(2):242–254, Takemoto et al. (1999) *Tetrahedron (Asymmetry)* 10:1787–1793, Maligres et al. (1997) *Tetrahedron* 53(32):10983–10992, Tata et al. (1997) *Bioorg. Med. Chem. Lett.* 7(6):663–668 and Evans et al. (1992) *J. Med. Chem.* 35:3919–3927.

Synthetic routes to the compounds provided herein are described in the Examples. One of skill in the art will understand that the synthetic routes can be modified to use different starting materials and/or alternate reagents to accomplish the desired transformations. Accordingly, the methods and reagents described herein are all expressed as non-limiting embodiments.

5.4. Analysis of the Compounds

The activity of MCHR2 can be assessed using a variety of in vitro and in vivo assays to determine functional, chemical, and physical effects, e.g., measuring ligand binding (e.g., radioactive ligand binding), second messenger (e.g., cAMP, cGMP, $IP_3$, DAG or $Ca^{2+}$) levels, ion flux, phosphorylation levels, transcription levels, neurotransmitter levels, and the like. Furthermore, such assays can be used to test for inhibitors and activators of MCHR2. Screening assays may be used to identify modulators that can be used as therapeutic agents, e.g., antagonists of MCHR2 activity.

Compounds can be tested for MCHR2 modulation using either recombinant or naturally occurring MCHR2 polypeptides, as described above. The protein can be isolated, expressed in a cell, expressed in a membrane derived from a cell, expressed in tissue or in an animal, either recombinant or naturally occurring. For example, kidney cells, liver cells, colon cells, transformed cells, or membranes can be used. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Gene expression can also be examined. Furthermore, ligand-binding domains of the protein of interest can be used in vitro in soluble or solid state reactions to assay for ligand binding.

Ligand binding to MCHR2, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index), or hydrodynamic (e.g., shape), chromatographic, or solubility properties.

MCHR2-G-protein interactions can also be examined, by, for example, analysis of binding of the G-protein to MCHR2 or its release from MCHR2 can be examined. For example, in the absence of GTP, an activator will lead to the formation of a tight complex of a G protein (all three subunits) with MCHR2. This complex can be detected in a variety of ways, as noted above. Such an assay can be modified to search for inhibitors. In one embodiment, an activator is added to MCHR2 and G protein in the absence of GTP, allowed to form a tight complex, and screened for inhibitors by looking at dissociation of the MCHR2-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and inositol triphosphate (IP3) by phospholipase C, and in turn, for calcium mobilization by IP3.

Activated MCHR2 becomes a substrate for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For a general review of GPCR signal transduction and methods of assaying signal transduction, see, e.g., *Methods in Enzymology*, vols. 237 and 238 (1994) and volume 96 (1983); Bourne et al., *Nature* 10:349:117–27 (1991); Bourne et al., *Nature* 348:125–32 (1990); Pitcher et al., *Annu. Rev. Biochem.* 67:653–92 (1998).

Samples or assays that are treated with a potential MCHR2 inhibitor or activator are compared to control samples without the test compound, to examine the extent of modulation. Control samples (untreated with activators or inhibitors) are assigned a relative MCHR2 activity value of 100. Inhibition of MCHR2 is achieved when the MCHR2 activity value relative to the control is about 90%, optionally 50%, optionally 25–0%. Activation of MCHR2 is achieved when the MCHR2 activity value relative to the control is 110%, optionally 150%, 200–500%, or 1000–2000%.

Changes in ion flux may be assessed by determining changes in polarization (i.e., electrical potential) of the cell or membrane expressing MCHR2. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981)). Other known assays include radiolabeled ion flux assays and fluorescence assays using voltage-sensitive dyes (see, e.g., Vestergarrd-Bogind et al., *J. Membrane Biol.* 88:67–75 (1988); Gonzales & Tsien, Chem. Biol. 4:269–277 (1997); Daniel et al., *J. Pharmacol. Meth.* 25:185–193 (1991); Holevinsky et al., *J. Membrane Biology* 137:59–70 (1994)). Generally, the compounds to be tested are present in the range from 1 pM to 100 mM.

The effects of the test compounds upon the function of the polypeptides can be measured by examining any of the parameters described above. Any suitable physiological change that affects MCHR2 activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3 or cAMP.

Preferred assays for MCHR2 include cell-based assays using cells that are loaded with ion or voltage sensitive dyes to report receptor activity. Assays for determining activity of MCHR2 can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as G$\alpha$15 and G$\alpha$16 can be used in the assay of choice (Wilkie et al., *Proc. Nat'l Acad. Sci. USA* 88:10049–10053 (1991)). Such promiscuous G-proteins allow coupling of a wide range of receptors to signal transduction pathways in heterologous cells.

Receptor activation typically initiates subsequent intracellular events, e.g., increases in second messengers such as IP3, which releases intracellular stores of calcium ions. Activation of some G-protein coupled receptors stimulates the formation of IP3 through phospholipase C-mediated hydrolysis of phosphatidylinositol (Berridge & Irvine, *Nature* 312:315–21 (1984)). IP3 in turn stimulates the release of intracellular calcium ion stores. Thus, a change in cytoplasmic calcium ion levels, or a change in second messenger levels such as IP3 can be used to assess GPCR function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA or EDTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868–9872 (1991) and Dhallan et al., *Nature* 347:184–187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.* 270: 15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference. In another embodiment, phosphatidyl inositol (PI) hydrolysis can be analyzed according to U.S. Pat. No. 5,436,128, herein incorporated by reference.

In another embodiment, transcription levels can be measured to assess the effects of a test compound on signal transduction. A host cell containing the protein of interest is contacted with a test compound for a sufficient time to effect any interactions, and the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using a reporter gene may be used as described in U.S. Pat. No. 5,436,128, herein incorporated by reference. The reporter genes can be, e.g., chloramphenicol acetyltransferase, firefly luciferase, bacterial luciferase, $\beta$-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

The following examples are provided by way of illustration only and not by way of limitation. Those of skill in the art will readily recognize a variety of noncritical parameters that could be changed or modified to yield essentially similar results.

6. EXAMPLES

Reagents and solvents used below can be obtained from commercial sources such as Aldrich Chemical Co. (Milwaukee, Wis., USA). $^1$H-NMR spectra were recorded on a Varian Gemini 400 MHz NMR spectrometer. Significant peaks are tabulated in the order: multiplicity (br s, broad singlet; d, doublet; t, triplet; q, quartet; m, multiplet; s, singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses) or a single m/z value for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NH_4OAc$ in acetonitrile/water as delivery solvent. Enantiomeric purity was determined using a Hewlett-Packard Series 1050 system equipped with a chiral HLPC column (ChiralPak AD, 4.6 mm×150 mm) and isocratic elution using 10:90 isopropanol-hexane (each containing 0.1% diethylamine) as a mobile phase.

6.1. Example 1

Step 1: A mixture of indene i (5.0 g, 17.5 mmol) and mCPBA (5.75 g, purity 77% max.) in $CH_2Cl_2$ was stirred for 3 h at room temperature. The reaction mixture was poured into aqueous $NaHCO_3$ and extracted with EtOAc. The organic layer was separated, washed with brine, dried with anhydrous $Na_2SO_4$, concentrated by rotary evaporation and purified by flash chromatography on silica gel with a gradient elution of 20–40% EtOAc/hexanes to yield epoxide ii as a white solid (4.1 g).

Step 2: Epoxide ii (4.1 g, 13.6 mmol) was heated with $HCO_2NH_4$ (6.60 g, 104.7 mmol) and 10% Pd/C (0.88 g) in dioxane at 80° C. for 1 h. The mixture was cooled to room temperature and filtered through a Celite pad. The filtrate was partitioned between EtOAc and water. The organic layer was separated, washed with brine, dried with anhydrous $Na_2SO_4$, concentrated by rotary evaporation and purified by flash chromatography on silica gel with a gradient elution of 40–70% EtOAc/hexanes to yield a white semi-solid iii (3.60 g).

Step 3: Alcohol iii (3.60 g, 11.8 mmol) was stirred with pyridinium dichromate (PDC) (11.30 g, 30 mmol) in $CH_2Cl_2$ overnight. The mixture was filtered through a Celite pad. The filtrate was collected, concentrated and purified by flash

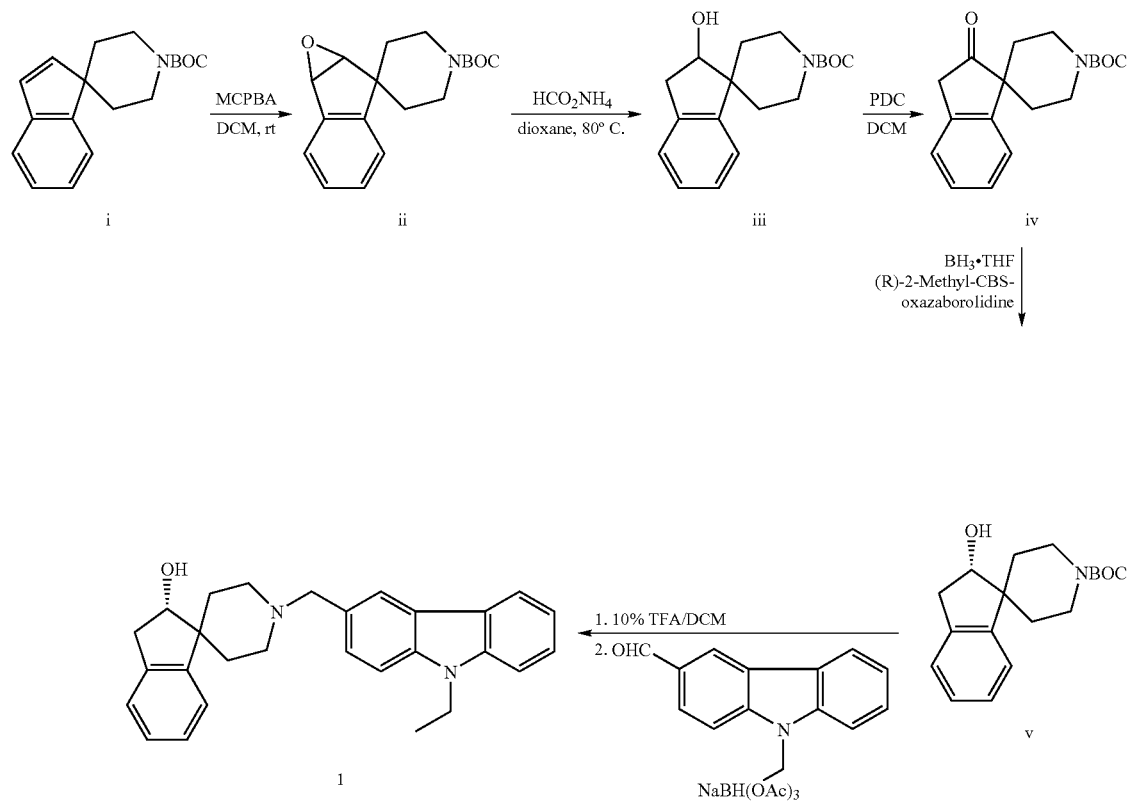

chromatography on silica gel with a gradient elution of 20–30% EtOAc/hexanes to yield ketone iv as a solid (2.60 g).

Step 4: Asymmetric reduction of ketone iv (Tetrahedron: Asymmetry (1999) 20:1787) was performed as follows. A

6.2. Example 2

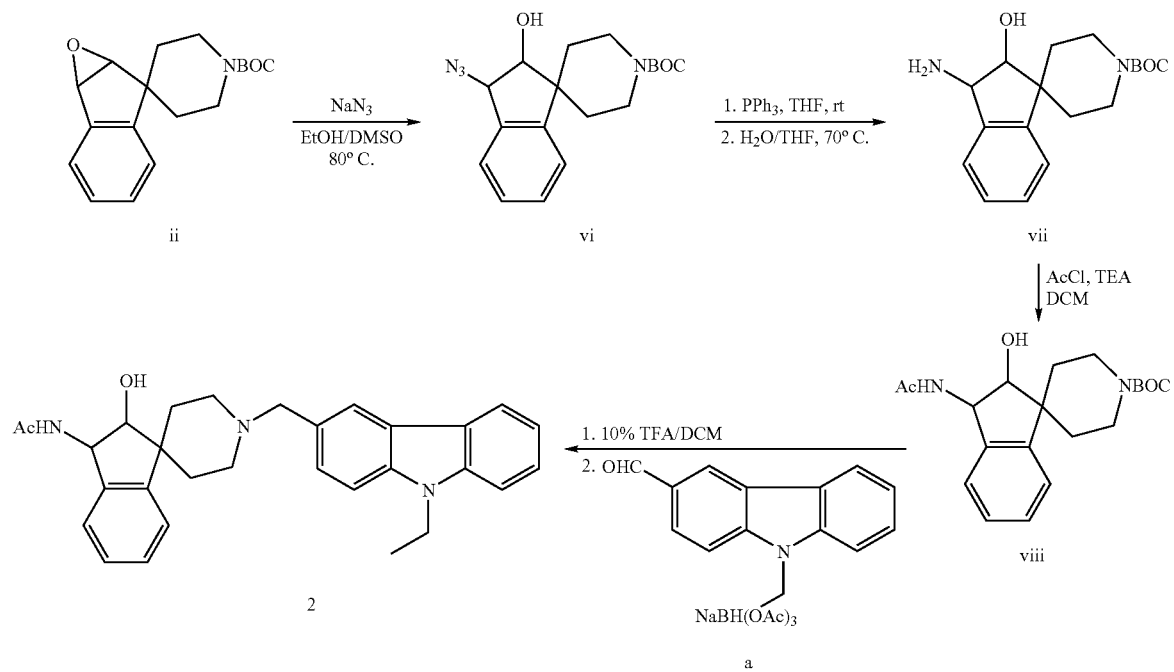

mixture was formed by adding ketone iv (0.151 g, 0.5 mmol) in TBF (1 mL) to (R)-2-methyl-CBS oxazaborolidine (0.050 mL) under $N_2$ dropwise. $BH_3$-THF (1.0 mL, 1 mmol, 1 M in THF) was added to the above mixture dropwise at −13° C. The reaction mixture was stirred for 40 min. at room temperature, cooled to 0° C. and quenched with water. The mixture was extracted with EtOAc. The organic layer was separated, washed with brine, dried with anhydrous $Na_2SO_4$, concentrated by rotary evaporation and purified by flash chromatography on silica gel with a gradient elution of 40–60% EtOAc/hexanes to yield alcohol v as a white solid (0.085 g). The obtained ee was approx. 87%.

Step 5: Compound v was deprotected by stirring v (0.26 mmol) with 10% $TFA/CH_2Cl_2$ (3 mL) for 30 min. The solvent was removed in vacuo and the residue was treated with 9-ethyl-9H-carbazole-3-carboxaldehyde (a) (0.090 g, 0.40 mmol) and $NaBH(OAc)_3$ (0.300 g, 1.41 mmol) in 1,2-dichloroethane (2 mL). The medium was brought to neutral or slightly acidic by adding $NEt_3$/HOAc. After 2 h, the reaction mixture was poured into aqueous $NaHCO_3$ and extracted with EtOAc. The organic layer was separated, washed with brine, dried with anhydrous $Na_2SO_4$, concentrated by rotary evaporation and purified by flash chromatography on silica gel with a gradient elution of 5–15% $MeOH/CH_2Cl_2$ to yield compound 1 as a white solid (0.025 g). $^1H$ NMR (DMSO-$d_6$): δ 8.15 (d, J=7.7 Hz, 1H), 8.10 (s, br, 1H), 7.58 (m, 2H), 7.44 (m, 2H), 7.15 (m, 5H), 4.77 (s, 1H), 4.43 (q, J=7.0 Hz, 2H), 4.30 (s, br, 1H), 3.69 (s, br, 2H), 3.14 (m, br, 1H), 2.79 (s, br, 2H), 2.69 (m, 1H), 2.40 (s, 2H), 2.01 (m, 1H), 1.82 (s, br, 1H), 1.56 (s, br, 2H), 1.30 (t, J=7.1 Hz, 3H). MS (ES): 411 [M+H].

Step 1: A mixture of epoxide ii (0.482 g, 1.6 mmol) and $NaN_3$ (0.416 g, 6.4 mmol) in EtOH (8 mL) and DMSO (8 mL) was heated to 80° C. for 30 min. The reaction mixture was cooled to room temperature, poured into aqueous $NaHCO_3$ and extracted with EtOAc. The organic layer was separated, washed with brine, dried with anhydrous $Na_2SO_4$, concentrated by rotary evaporation and purified by flash chromatography on silica gel with a gradient elution of 30–40% EtOAc/hexanes to yield azide vi as a yellowish solid (0.145 g).

Step 2: Azide vi (0.100 g, 0.29 mmol) was stirred with $PPh_3$ (0.152 g, 0.58 mmol) in THF (2 mL) under $N_2$ at room temperature for 5 h. Water (0.20 mL) was added and the mixture was heated to 70° C. for 4 h. The mixture was loaded directly on a silica gel column. Elution with a gradient of 20–30% MeOH—$CH_2Cl_2$ with 0–10% ammonium hydroxide to afforded amine vii as a white solid (0.071 g).

Step 3: Amine vii (0.070 g, 0.22 mmol) was stirred with AcCl (0.017 mL, 0.24 mmol) and TEA (0.042 mL, 0.3 mmol) in $CH_2Cl_2$ (0.8 mL) for 10 min. The mixture was loaded directed on a column and eluted with a gradient of 0–20% MeOH/EtOAc to yield viii as a white solid (0.047 g).

Step 4: Deprotection of viii was accomplished by stirring viii (0.047 g, 0.13 mmol) with 10% $TFA/CH_2Cl_2$ (1 mL) for 15 min. The solvent was removed in vacuo and the residue was treated with 9-ethyl-9H-carbazole-3-carboxaldehyde (a) (0.090 g, 0.40 mmol) and $NaBH(OAc)_3$ (0.424 g, 2 mmol) in 1,2-dichloroethane (1.5 mL). The medium was brought to neutral or slightly acidic by adding $NEt_3$/HOAc. After 1 h, the reaction mixture was poured into aqueous NaHCO₃ and extracted with EtOAc. The organic layer was separated, washed with brine, dried with anhydrous Na₂SO₄, concentrated by rotary evaporation and purified by flash chromatography on silica gel with a gradient elution of 5–15% MeOH/CH₂Cl₂ to yield compound 2 as a white solid (0.030 g). MS (ES): 468 [M+H].

6.3. Example 3

Step 3: Compound ix (0.050 g, 0.16 mmol) was refluxed with HCO₂NH₄ (0.120 g, 1.9 mmol) and 10% Pd/C (0.05 g) in MeOH (2 mL) for 30 min. After cooling to room temperature, the reaction mixture was filtered through a Celite pad. The filtrate was collected and concentrated in vacuo to obtain x.

Step 4: Amine x (0.16 mmol) was mixed with 9-ethyl-9H-carbazole-3-carboxaldehyde (a) (0.10 g, 0.44 mmol) and

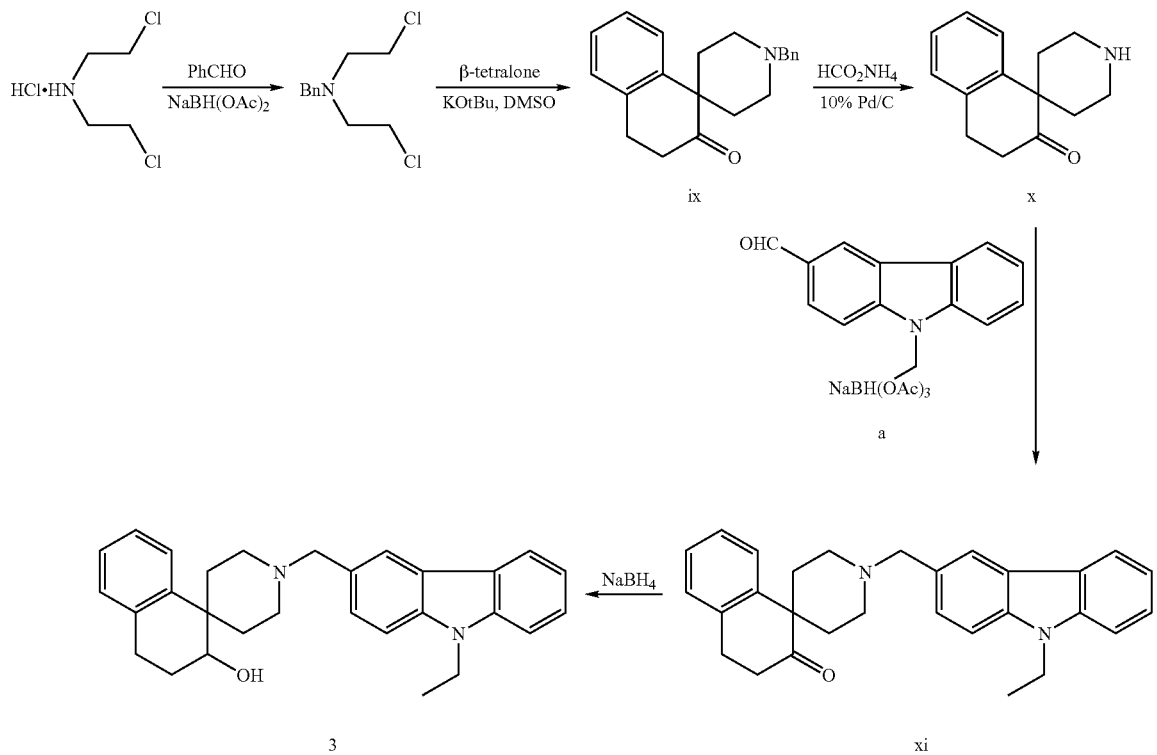

Step 1: A mixture of bis(2-chloroethyl)amine HCl (4.462 g, 25 mmol), benzyl aldehyde (2.6 mL, 30 mmol), NaBH(OAc)₃ and TEA (3.5 mL, 25 mmol) in 1,-2-dichloroethane (150 mL) was stirred at room temperature for 6 h. The reaction mixture was poured into aqueous NaHCO₃ and extracted with EtOAc. The organic layer was separated, washed with brine, dried with anhydrous Na₂SO₄, concentrated by rotary evaporation and purified by flash chromatography on silica gel with a gradient elution of 10–40% EtOAc/hexanes to yield N-benzyl-N,N-di(2-chloroethyl) amine as a clear oil (4.48 g).

Step 2: To a mixture of KOtBu (37.6 mL, 37.6 mmol, 1M/tBuOH) in DMSO (80 mL) under N₂ was added β-tetralone (2.50 g, 17.1 mmol, in DMSO) dropwise followed by addition of N-benzyl-N,N-di(2-chloroethyl)amine (3.82 mL, 18.8 mmol). After stirring overnight at room temperature, the mixture was poured into water and extracted with EtOAc. The organic layer was separated, washed with brine, dried with anhydrous Na₂SO₄, concentrated by rotary evaporation and purified by flash chromatography on silica gel with a gradient elution of 25–60% EtOAc/hexanes to yield compound ix as a brown oil (1.30 g).

NaBH(OAc)₃ (0.20 g, 0.94 mmol) in 1,2-dichloroethane (2 mL). The medium was brought to neutral or slightly acidic by adding NEt₃/HOAc. After stirring overnight, the reaction mixture was poured into aqueous NaHCO₃ and extracted with EtOAc. The organic layer was separated, washed with brine, dried with anhydrous Na₂SO₄, concentrated by rotary evaporation and purified by flash chromatography on silica gel with a gradient elution of 3–10% MeOH/CH₂Cl₂ to yield xi as a white solid (0.037 g).

Step 5: Ketone xi was stirred with NaBH₄ (0.010 g, 0.26 mmol) in MeOH (1 mL) and CH₂Cl₂ (0.2 mL) for 15 min. at room temperature. The reaction mixture was poured into aqueous NaHCO₃ and extracted with EtOAc. The organic layer was separated, washed with brine, dried with anhydrous Na₂SO₄, concentrated by rotary evaporation and purified by flash chromatography on silica gel with a gradient elution of 5–15% MeOH/CH₂Cl₂ to yield compound 3 as a white solid (0.010 g). ¹H NMR (DMSO-d₆): δ 8.16 (s, br, 1H), 8.14 (d, J=7.7 Hz, 1H), 7.60 (m, 2H), 7.52 (m, 1H), 7.46 (dd, J=7.6 Hz, 1H), 7.39 (d, J=8.1 Hz, 1H), 7.20 (dd, J=7.6 Hz, 1H), 7.12 (dd, J=7.5 Hz, 1H), 7.02 (m, 2H), 4.60 (s, br, 2H), 4.44 (q, J=7.2 Hz, 2H), 4.28 (s, br, 1H), 3.95 (s, br, 2H), 2.98 (m, 2H), 2.82 (s, br, 1H), 2.53 (s, br, 1H), 2.13

(m, 2H), 2.06 (m, 1H), 1.84 (m, 3H), 1.68 (m, 1H), 1.32 (t, J=7.0 Hz, 3H). MS (ES): 425 [M+H].

6.4. Example 4

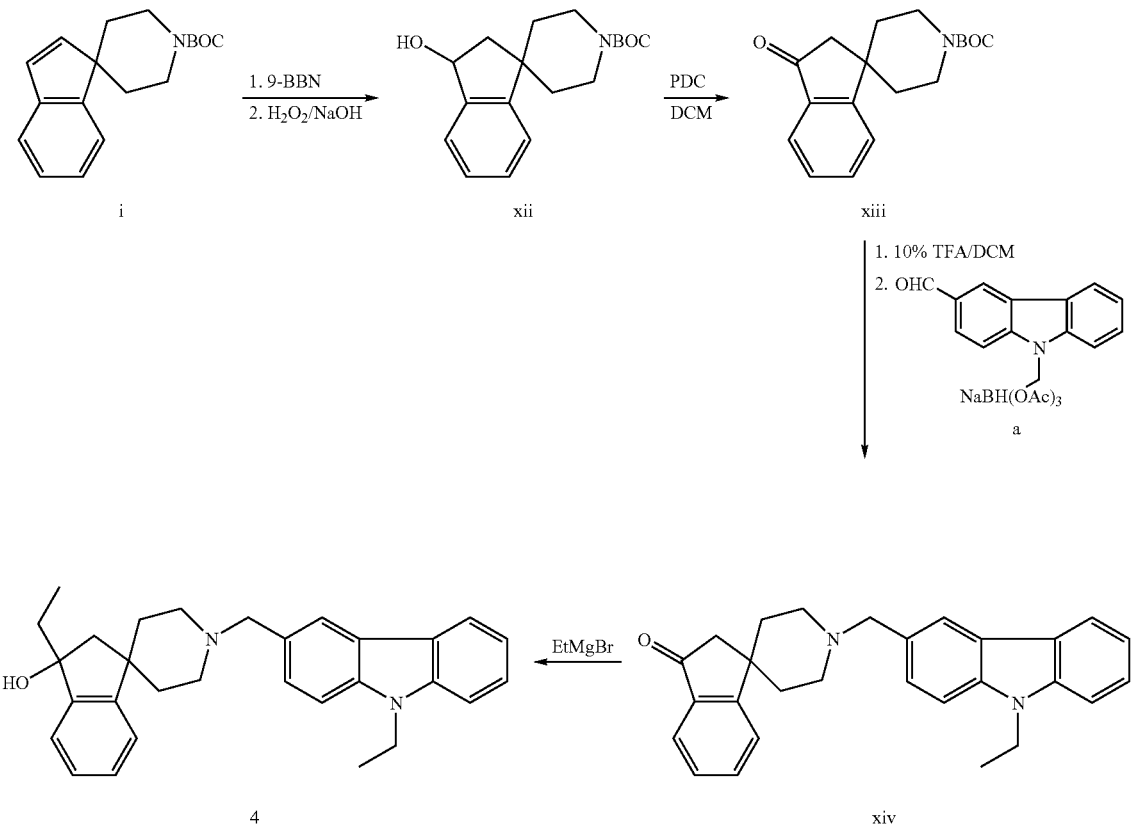

Step 1: A mixture of i (6.0 g, 21 mmol) and 9-BBN (83 mL, 41.5 mmol, 0.5 M/THF) in THF (40 mL) was refluxed for 2 h. The mixture was cooled to 0° C. NaOH (15 mL, 3MMH$_2$O) was added to the above mixture followed by H$_2$O$_2$ (15 mL, 30% w/w). The mixture was stirred for 1.5 h at room temperature, poured into aqueous NH$_4$Cl and extracted with EtOAc. The organic layer was separated, washed with brine, dried with anhydrous Na$_2$SO$_4$, concentrated by rotary evaporation and purified by flash chromatography on silica gel with a gradient elution of 40–70% EtOAc/hexanes to yield xii as a white solid (5.20 g).

Step 2: Alcohol xii (5.20 g, 17 mmol) was stirred with PDC (13 g, 34.5 mmol) in CH$_2$Cl$_2$ (100 mL) overnight. The reaction mixture was filtered through a Celite pad. The filtrate was collected, concentrated and purified by flash chromatography on silica gel with a gradient elution of 30–50% EtOAc/hexanes to yield ketone xiii as a white solid (4.93 g, 95%).

Step 3: Deprotection of xiii was accomplished by stirring xiii (2.10 g, 6.8 mmol) with 15% TFA/CH$_2$Cl$_2$ (40 mL) for 1 h. The solvent was removed in vacuo and the residue was treated with 9-ethyl-9H-carbazole-3-carboxaldehyde (a) (2.34 g, 10.5 mmol) and NaBH(OAc)$_3$ (7.42 g, 35 mmol) in 1,2-dichloroethane (40 mL). The medium was brought to neutral or slightly acidic by adding NEt$_3$/HOAc. The reaction continued overnight at room temperature. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 50%–100% EtOAc/hexanes followed 5–20% MeOH/EtOAc to yield xiv as a foam solid (2.70 g).

Step 4: Ketone xiv (0.062 g, 0.15 mmol) was heated with EtMgBr (0.60 mL, 0.6 mmol, 1 M in tBuOMe) to 60° C. for 10 min. The reaction mixture was poured into water and extracted with EtOAc. The organic layer was separated, washed with brine, dried with anhydrous Na$_2$SO$_4$, concentrated by rotary evaporation and purified by flash chromatography on silica gel with a gradient elution of 5%–15% MeOH/CH$_2$Cl$_2$ to yield compound 4 as a white solid (0.045 g). $^1$H NMR (DMSO-d$_6$): δ 8.15 (d, J=7.7 Hz, 1H), 8.10 (s, br, 1H), 7.58 (m, 2H), 7.45 (m, 2H), 7.22 (m, 5H), 4.73 (s, 1H), 4.43 (q, J=7.2 Hz, 2H), 3.67 (s, br, 2H), 2.86 (s, br, 2H), 2.15 (s, br, 2H), 2.03 (s, 2H), 1.83 (m, 3H), 1.61 (m, 3H), 1.31 (t, J=7.1 Hz, 3H), 0.88 (t, J=7.2 Hz, 3H). MS (ES): 439 [M+H].

6.5. Example 5

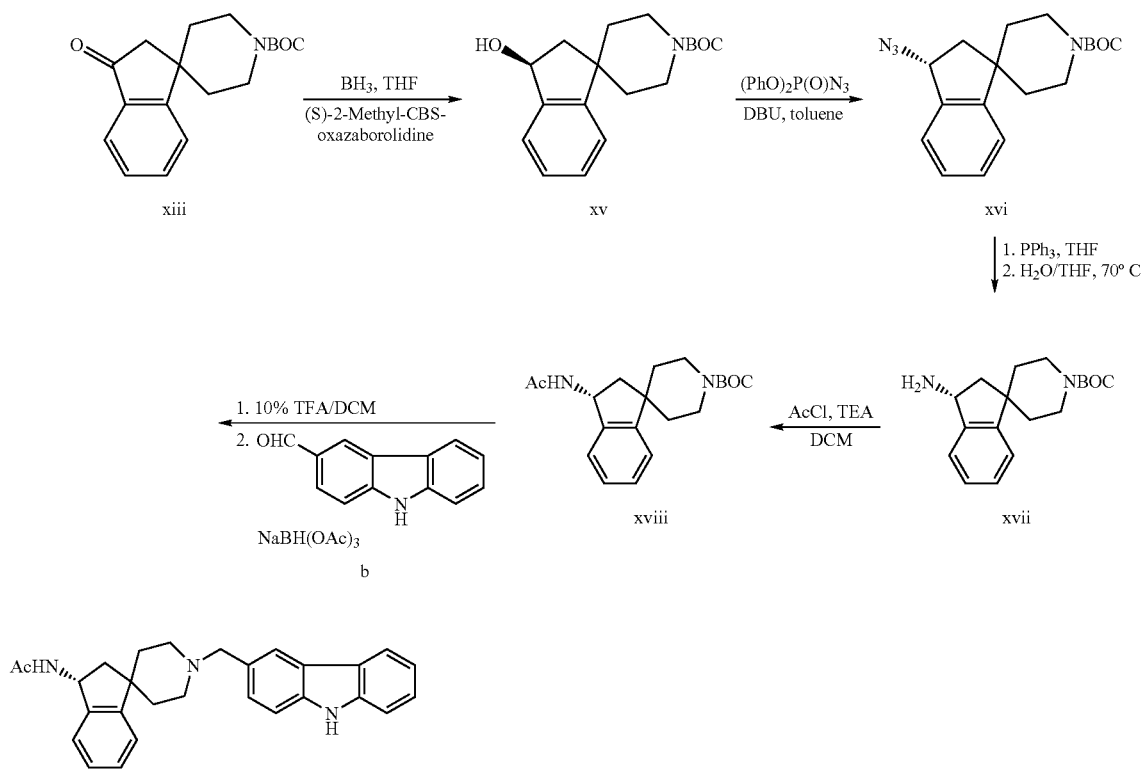

Step 1: A mixture of BH$_3$.THF (39 mL, 39 mmol, 1 M/THF) and (S)-2-methyl-CBS oxazaborolidine (39 mL, 39 mmol, 1 M/toluene) was added to a mixture of ketone xiii (9.0 g, 30 mmol) and TEA (4.2 mL, 30 mmol) in THF (80 mL) at −13° C. dropwise. The reaction continued for 1.5 h at −13° C. The reaction mixture was poured into water and extracted with EtOAc. The organic layer was separated, washed with brine, dried with anhydrous Na$_2$SO$_4$, concentrated by rotary evaporation and purified by flash chromatography on silica gel with a gradient elution of 30–65% EtOAc/hexanes to yield alcohol xv as a foam solid (7.5 g, ee>99%).

Step 2: To a mixture of alcohol xv (7.5 g, 24.75 mmol) and DPPA (6.4 mL, 29.7 mmol) in toluene (50 mL) was added DBU (4.07 mL, 27.2 mmol) dropwise. After 1.5 h, the reaction mixture was poured into water and extracted with EtOAc. The organic layer was separated, washed with brine, dried with anhydrous Na$_2$SO$_4$, concentrated by rotary evaporation and purified by flash chromatography on silica gel with a gradient elution of 15–20% EtOAc/hexanes to yield xvi as a oil (8.1 g, ee=95%).

Step 3: Azide xvi (8.1 g, 24.75 mmol) was stirred with PPh$_3$ (13.39 g, 51 mmol) in THF (150 mL) under N$_2$ at room temperature for 8 h. Water (15 mL) was added to the mixture and the reaction mixture was heated to 70° C. for 8 h. The content was directly loaded on a silica gel column eluting with a gradient of 5–30% MeOH/EtOAc with 0–8% ammonia to yield xvii as a foam solid (5.7 g).

Step 4: To a solution of xvii (4.5 g, 15 mmol) in CH$_2$Cl$_2$ (100 mL) was added AcCl (1.38 mL, 19.5 mmol) and TEA (3.22 mL, 23 mmol) at 0° C. The mixture was stirred for 10 min. at 0° C. followed by 30 min. at room temperature. The mixture was loaded directly on a column and chromatographed with a gradient elution of 0–7% MeOH/EtOAc to yield xviii as a white solid (5.0 g, 100%).

Step 5: Deprotection of xviii was accomplished by stirring xvii (4.90 g, 14.7 mmol) with 2M HCl/DCM/dioxane (50 mL) for 1 h. The solvent was removed in vacuo. The amine salt (13.1 mmol) was converted to the free base by adding TEA (1.8 mL, 13 mmol) in a mixed solvent of CH$_2$Cl$_2$ (60 mL) and 1,2-dichloroethane (60 mL). The free amine was treated with 9H-carbazole-3-carboxaldehyde (b) (3.11 g, 15.7 mmol) in the presence of NaBH(OAc)$_3$ (12.32 g, 58 mmol). The reaction continued overnight at room temperature. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 5%–30% MeOH/CH$_2$Cl$_2$ to yield compound 5 as a white solid (3.50 g). $^1$H NMR (HCl salt) (DMSO-d$_6$): δ 11.52 (s, 1H), 10.70 (s, 1H), 8.36 (s, 1H), 8.26 (d, J=8.0 Hz, 1H), 8.06 (d, J=7.7 Hz, 1H), 7.64 (dd, J=8.3, 1.5 Hz, 1H), 7.53 (m, 2H), 7.42 (dd, J=7.6 Hz, 1H), 7.2–7.4 (m, 5H), 5.32 (m, 1H), 4.47 (d, J=5.1 Hz, 2H), 3.35 (m, 2H), 3.18 (m, 2H), 2.65 (m, 1H), 2.08 (m, 1H), 1.87 (s, 3H), 1.67 (m, 3H), 1.05 (t, J=7.0 Hz, 1H). MS (ES): 424 [M+H].

6.6. Example 6

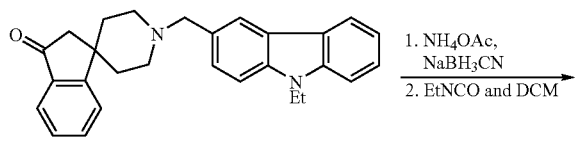

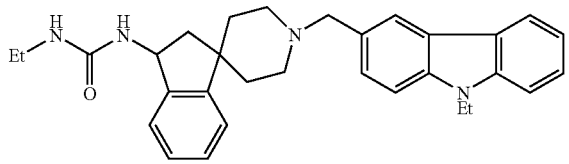

6

Step 1: Compound xiv (1.0 g, 2.44 mmol) was heated with NH$_4$OAc (1.88 g, 24.4 mmol) and NaBH$_3$CN (1.53 g, 24.4 mmol) in MeOH (20 mL) and CH$_2$Cl$_2$ (20 mL) to 60° C. overnight. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20%–40% MeOH/CH$_2$Cl$_2$ with 0–10% NH$_4$OH to yield the corresponding amine (xix) (0.40 g).

Step 2: The amine from Step 1 (xix) (0.041 g, 0.1 mmol) was stirred with EtNCO (0.015 mL, 0.2 mmol) in CH$_2$Cl$_2$ (1 mL) for 15 min. at room temperature. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 5%–15% MeOH/CH$_2$Cl$_2$ to yield compound 6 as a white solid (0.040 g). $^1$H NMR (DMSO-d$_6$): δ 8.15 (d, J=7.5 Hz, 1H), 8.11 (s, br, 1H), 7.62 (m, 2H), 7.45 (m, 2H), 7.21 (m, 5H), 6.15 (m, 1H), 5.76 (m, 1H), 5.12 (m, 1H), 4.43 (q, J=7.0 Hz, 2H), 3.67 (s, br, 2H), 3.06 (m, 2H), 2.87 (s, br, 2H), 2.55 (s, br, 1H), 2.12 (s, 3H), 1.67 (s, br, 1H), 1.48 (s, br, 3H), 1.32 (t, J=7.1 Hz, 3H), 1.01 (t, J=7.1 Hz, 3H). MS (ES): 481 [M+H].

6.7. Example 7

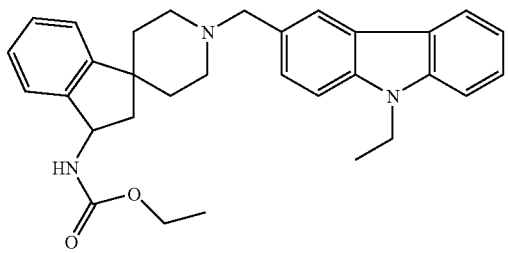

7

Amine xix (see Example 6) (0.041 g, 0.1 mmol) was stirred with ClCO$_2$Et (0.019 mL, 0.2 mmol) in CH$_2$Cl$_2$ (1 mL) for 15 min. at room temperature. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 5%–15% MeOH/CH$_2$Cl$_2$ to yield compound 7 as a white solid (0.030 g). $^1$H NMR (DMSO-d$_6$): δ 8.15 (d, J=7.7 Hz, 1H), 8.07 (s, 1H), 7.57 (m, 2H), 7.45 (m, 3H), 7.22 (m, 4H), 5.06 (m, 1H), 4.43 (q, J=7.0 Hz, 2H), 4.04 (q, J=7.0 Hz, 2H), 3.67 (s, br, 2H), 3.31 (m, 1H), 2.83 (s, br, 2H), 2.65 (m, 1H), 2.16 (m, 3H), 1.61 (m, 2H), 1.45 (m, 2H), 1.32 (t, J=7.1 Hz, 3H), 1.19 (t, J=7.1 Hz, 3H). MS (ES): 482 [M+H].

6.8. Example 8

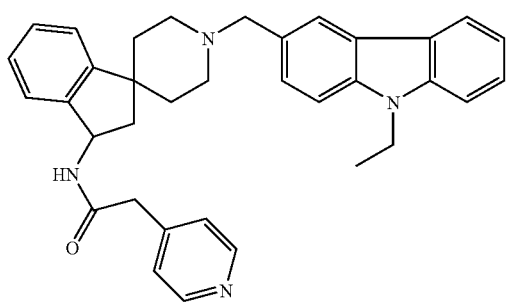

8

Step 1: Amine xvii (see Example 5) (0.040 g, 0.13 mmol) was stirred with 4-pyridylacetic acid HCl (0.035 g, 0.20 mmol), EDC (0.036 g, 0.26 mmol), HOBt (0.051 g, 0.26 mmol) and TEA (0.056 mL, 0.4 mmol) in CH$_2$Cl$_2$ (1 mL) and DMF (1 mL) overnight. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 0–20% MeOH/EtOAc to yield the corresponding amide as a white solid (0.045 g).

Step 2: Deprotection of the above amide (0.048 g, 0.113 mmol) was accomplished by stirring with 2M HCl/DCM/dioxane (1.5 mL) for 30 min. The solvent was removed in vacuo and the residue was neutralized with TEA in 1,2-dichloroethane (1 mL). The solution was treated with 9H-carbazole-3-carboxaldehyde (b) (0.050 g, 0.25 mmol) in the presence of NaBH(OAc)$_3$ (0.12 g, 0.56 mmol). The reaction continued overnight at room temperature. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 10%–40% MeOH/CH$_2$Cl$_2$ to yield compound 8 as a white solid (0.024 g). $^1$H NMR (DMSO-d$_6$): δ 11.21 (s, br, 1H), 8.57 (s, br, 1H), 8.49 (m, 2H), 8.10 (m, 1H), 8.02 (s, br, 1H), 7.42 (m, 4H), 7.07–8.32 (m, 7H), 5.28 (m, 1H), 3.62 (m, 2H), 3.52 (s, 2H), 2.82 (s, 2H), 2.12 (m, 2H), 1.37–1.77 (m, 6H). MS (ES): 501 [M+H].

6.9. Example 9

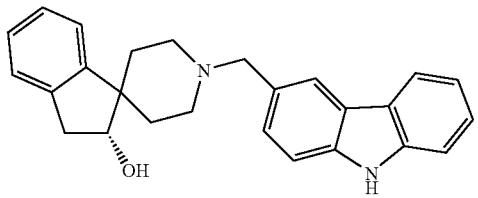

Compound 9 was synthesized following the procedure described in Example 1, step 5, replacing 9-ethyl-9H-carbazole-3-carboxaldehyde (a) with 9H-carbazole-3-carboxaldehyde (b). $^1$H NMR (400 MHz, CD$_3$OD) δ 8.22 (s, 1H), 8.09 (d, J=8 Hz, 1H), 7.47–7.53 (m, 3H), 7.40(t, J=8 Hz, 1H), 7.15–7.21 (m, 5H), 4.42 (m, 1H), 4.38 (s, 2H), 3.19–3.41 (m, 5H), 2.83 (d, J=16 Hz, 1H), 2.20 (d, J=16 Hz, 1H), 2.07 (m, 2H), 1.65 (d, J=16 Hz, 1H); ESI (MH$^+$) m/z 383.

6.10. Example 10

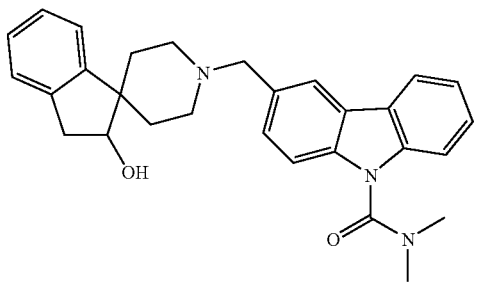

Compound 10 was synthesized following the procedure described in Example 1, step 5, replacing 9-ethyl-9H-carbazole-3-carboxaldehyde (a) with 9-N,N-dimethylcarbomylcarbazole-3-carboxaldehyde. $^1$H NMR (400 MHz, CD$_3$OD) δ 8.23 (s, 1H), 8.13 (d, J=8 Hz, 1H), 7.49–7.61 (m, 4H), 7.34 (td, J=1 Hz, J=8 Hz, 1H), 7.11–7.22 (m, 4H), 4.40 (m, 1H), 4.15 (s, 2H), 3.20–3.29 (m, 3H), 3.11 (s, 6H), 3.00 (qd, J=3 Hz, J=12 Hz, 2H), 2.82 (dd, J=3 Hz, 16 Hz, 1H), 2.18 (d, J=12 Hz, 1H), 2.10 (m, 1H), 1.83–1.89 (m, 1H), 1.64 (d, J=12 Hz, 1H); ESI (MH$^+$) m/z 454.

6.11. Example 11

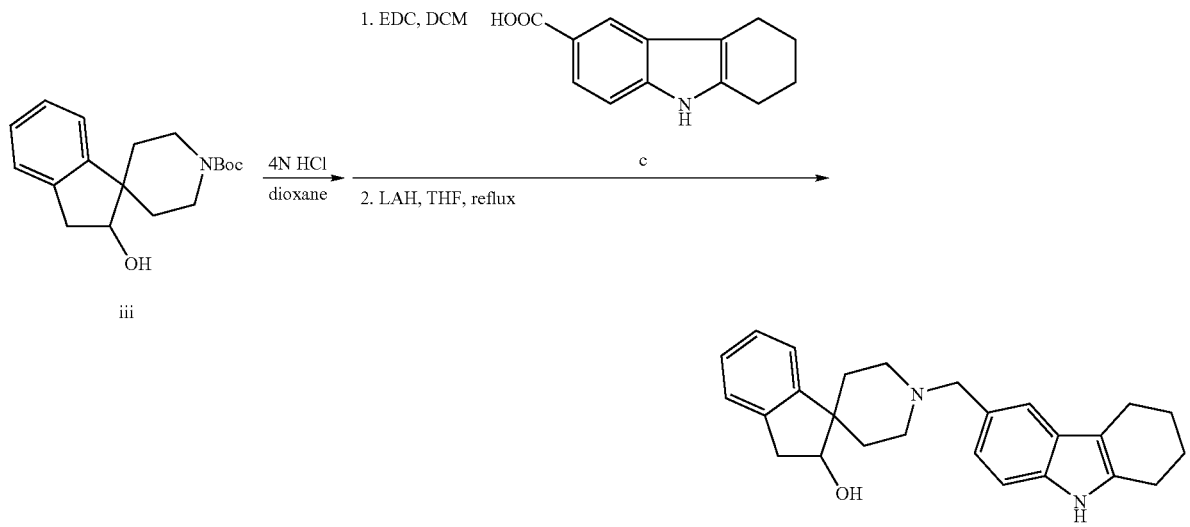

Boc protected alcohol (70 mg, 0.30 mmol) was deprotected by stirring with 2M HCl/DCM/dioxane (1.5 mL) for 30 min. The solvent was removed in vacuo and the residue was neutralized with TEA in 1,2-dichloroethane (1 mL). EDC (65 mg, 0.35 mmol) was added to the solution followed by addition of carboxylic acid c (*J. Am. Chem. Soc.* (1940) 62:527–530) (126 mg, 0.60 mmol) at room temperature. After stirring for 24 h, the solution was partitioned with water washed with 1 N HCl, brine, dried over Na$_2$SO$_4$, and concentrated. The resulting material was dissolved in dry THF and LAH (100 mg, 2.6 mmol) was added. After heating at reflux for 5 h, the solution was cooled to room temperature and treated with water (0.1 mL), 1 N NaOH (0.1 mL), and followed by another addition of water (0.2 mL). The resulting solid was filtered and washed with EtOAc. The filtrate was concentrated, and the remaining residue was purified using preparative reverse phase HPLC. Fractions that contained the desired product (11) were collected and concentrated. $^1$H NMR (400 MHz, CD$_3$OD) δ 7.55 (s, 1H), 7.35 (d, J=8 Hz, 1H), 7.17–7.24 (m, 3H), 7.15–7.16 (m, 2H), 4.53 (m, 1H), 4.39 (d, J=4 Hz, 2H), 3.50 (m, 2H), 3.28–3.40 (m, 2H), 2.88 (dd, J=4 Hz, J=16 Hz, 1H), 2.71–2.78 (m, 4H), 2.30 (dd, J=4 Hz, J=12 Hz, 1H), 1.98–2.10 (m, 2H), 1.88–1.96 (m, 5H), 1.74 (dd, J=4 Hz, J=16 Hz, 1H); ESI (MH$^+$) m/z 387.

6.12. Example 12

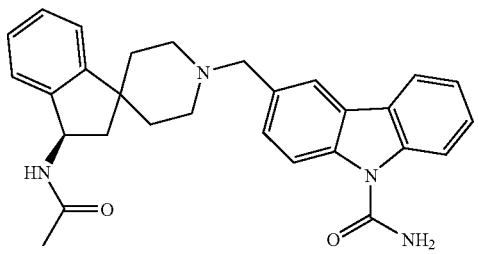

12

Compound 12 was synthesized by reacting compound 5 with trichloroacetylisocynate in dichloromethane followed by stirring with basic Al$_2$O$_3$. The desired compound was isolated by reverse phase HPLC. $^1$H NMR (400 MHz, CD$_3$OD) δ 8.11 (m, 2H), 8.05 (t, J=8 Hz, 2H), 7.46–7.53(m, 2H), 7.37 (t, J=8 Hz, 1H), 7.21–7.30 (m, 4H), 5.39 (t, J=8 Hz, 1H), 3.79 (s, 2H), 3.00(d, J=8 Hz, 2H), 2.67 (dd, J=8 Hz, J=12 Hz, 1H), 2.24–2.41 (m, 3H), 2.00 (s, 3H), 1.82 (td, J=4 Hz, J=8 Hz, 1H), 1.53–1.69 (m, 3H); ESI (MH$^+$) m/z 467.

6.13. Example 13

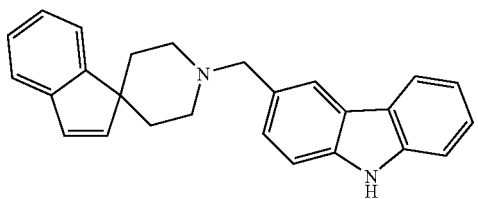

13

Compound i (see Example 1) was deprotected by stirring i (0.26 mmol) with 10% TFA/CH$_2$Cl$_2$ (3 mL) for 30 min. The solvent was removed in vacuo and the residue was treated with 9H-carbazole-3-carboxaldehyde (b) (0.090 g, 0.40 mmol) and NaBH(OAc)$_3$ (0.300 g, 1.41 mmol) in 1,2-dichloroethane (2 mL). The medium was brought to neutral or slightly acidic by adding NEt$_3$/HOAc. After stirring overnight, the reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 5–15% MeOH/CH$_2$Cl$_2$ to yield compound 13 as a white solid (0.025 g). $^1$H NMR (400 MHz, CD$_3$OD) δ 8.06 (m, 2H), 7.34–7.48 (m, 4H), 7.29 (d, J=8 Hz, 1H), 7.23 (d, J=8 Hz, 1H), 7.09–7.17 (m, 3H), 6.81 (d, J=8 Hz, 1H), 6.69 (d, J=8 Hz, 1H), 3.78 (s, 2H), 3.3 (d, J=12 Hz, 2H), 2.47 (t, J=12 Hz, 2H), 2.15 (t, J=12 Hz, 2H), 1.23 (d, J=12 Hz, 2H); ESI (MH$^+$) m/z 365.

6.14. Example 14

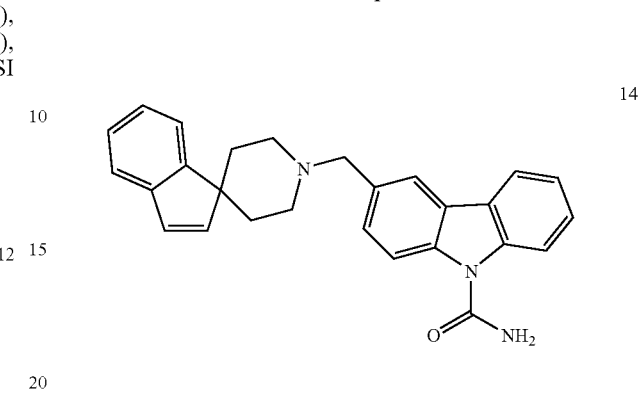

14

Compound 14 was synthesized by reacting compound 13 with trichloroacetylisocynate in dichloromethane followed by stirring with basic Al$_2$O$_3$. following the procedure described in Example 12. The desired compound was isolated by reverse phase HPLC. $^1$H NMR (400 MHz, CD$_3$OD) δ 8.34 (s, 1H), 8.20 (d, J=8 Hz, 1H), 8.15 (d, J=8 Hz, 1H), 8.06 (d, J=8 Hz, 1H), 7.66 (dd, J=4 Hz, J=8 Hz, 1H), 7.56 (td, J=4 Hz, J=8 Hz, 1H), 7.41 (t, J=8 Hz, 1H), 7.31–7.36 (m, 2H), 7.18–7.26 (m, 2H), 7.05 (d, J=8 Hz, 1H), 6.92 (d, J=8 Hz, 1H), 4.62 (s, 2H), 3.70 (d, J=12 Hz, 2H), 3.42 (t, J=12 Hz, 2H), 2.44 (t, J=12 Hz, 2H), 1.51 (d, J=12 Hz, 2H); ESI (MH$^+$) m/z 408.

6.15. Example 15

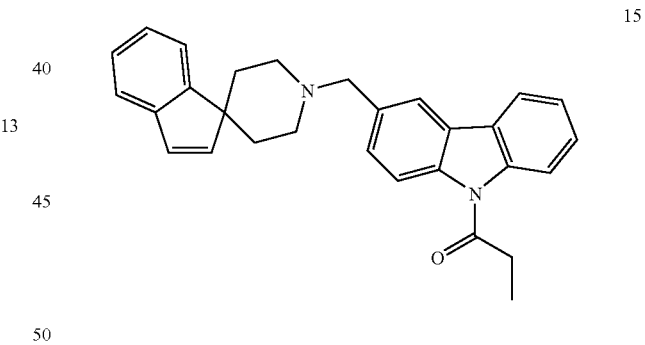

15

Sodium hydride (60% in mineral oil) (28 mg, 0.70 mmol) was added to a DMF solution (0.75 mL) containing compound 13 (50 mg, 0.14 mmol) at room temperature. After stirring 1 min., the corresponding propionyl chloride (0.70–1.40 mmol) was added, and the reaction vessel was sealed and heated at 90° C. for 5–24 h. The reaction mixture was injected directly on a preparative reverse phase HPLC column and fractions containing the desired product (15) were collected and concentrated. $^1$H NMR (400 MHz, CD$_3$OD) δ 8.53 (d, J=8 Hz, 1H), 8.32 (d, J=4 Hz, 1H), 8.27 (d, J=8 Hz, 1H), 8.17 (d, J=8 Hz, 1H), 7.69 (dd, J=4 Hz, J=8 Hz, 1H), 7.58 (t, J=8 Hz, 1H), 7.47 (t, J=8 Hz, 1H), 7.36 (d, J=8 Hz, 1H), 7.32 (d, J=8 Hz, 1H), 7.18–7.28 (m, 2H), 7.06 (d, J=8 Hz, 1H), 6.93 (d, J=8 Hz, 1H), 4.63 (s, 2H), 3.72 (d, J=16 Hz, 2H), 3.48 (t, J=16 Hz, 2H), 3.30 (q, J=8 Hz, 2H), 2.43 (td, J=4 Hz, J=16 Hz, 2H), 1.53 (d, J=16 Hz, 1H), 1.40 (t, J=8 Hz, 3H); ESI (MH$^+$) m/z 421.

6.16. Example 16

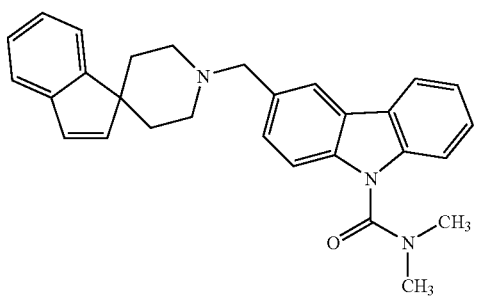

Compound 16 was synthesized following the procedure described in Example 15, substituting N,N-dimethylcarbamyl chloride for propionyl chloride. The desired product was isolated by reverse phase HPLC. $^1$H NMR (400 MHz, CD$_3$OD) δ 8.34 (s, 1H), 8.18 (d, J=8 Hz, 1H), 7.65–7.73 (m, 2H), 7.55–7.58 (m, 2H), 7.13–7.42 (m, 5H), 7.06 (d, J=8 Hz, 1H), 6.93 (d, J=8 Hz, 1H), 4.64 (s, 2H), 7.72 (d, J=16 Hz, 2H), 3.46 (t, J=8 Hz, 2H), 3.14 (s, 6H), 2.42 (td, J=4 Hz, J=16 Hz, 2H), 1.53 (d, J=16 Hz, 2); ESI (MH$^+$) m/z 436.

6.17. Example 17

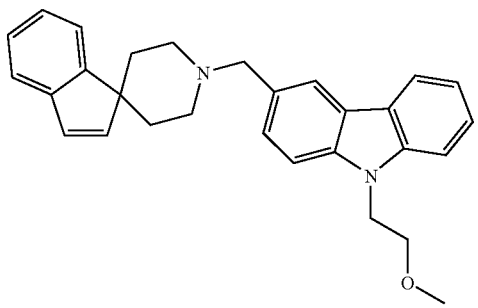

Compound 17 was synthesized following the procedure described in Example 15, substituting 2-chloroethyl methyl ether for propionyl chloride. The desired product was isolated by reverse phase HPLC. $^1$H NMR (400 MHz, CD$_3$OD) δ 8.31 (s, 1H), 8.14 (d, J=8 Hz, 1H), 7.67 (d, J=8 Hz, 1H), 7.60 (m, 2H), 7.50 (t, J=8 Hz, 1H), 7.19–7.35 (m, 5H), 7.05 (d, J=8 Hz, 1H), 6.91 (d, J=8 Hz, 1H), 4.61 (s, 2H), 4.58 (t, J=8 Hz, 2H), 3.80 (t, J=8 Hz, 2H), 3.69 (d, J=12 Hz, 2H), 3.44 (t, J=12 Hz, 2H), 3.24 (s, 3H), 2.42 (td, J=4 Hz, J=12 Hz, 2H), 1.50 (d, J=12 Hz, 2H); ESI (MH$^+$) m/z 423.

6.18. Example 18

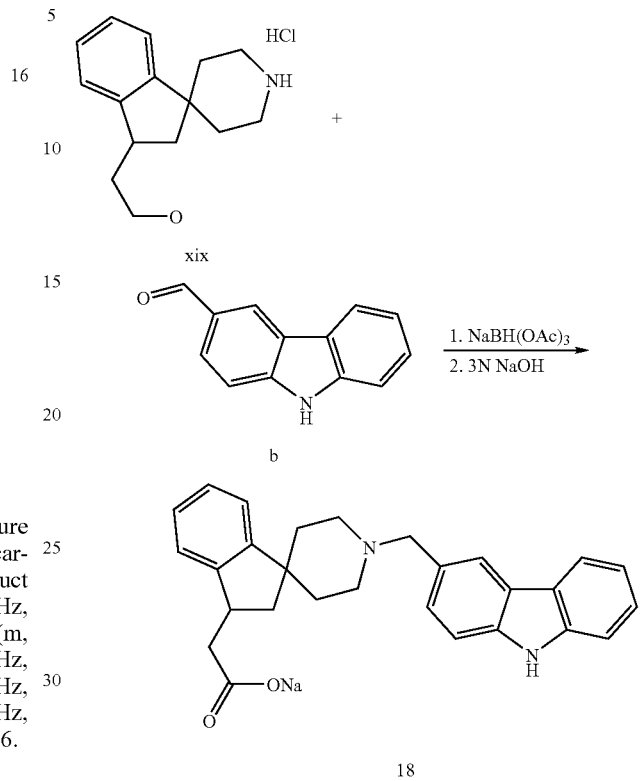

Sodium triacetoxyborohydride (1.12 g, 5.3 mmol) was added to a CH$_2$Cl$_2$ solution (40 mL) containing amine hydrochloride salt of xix (0.78 g, 2.6 mmol) and aldehyde b (0.62 g, 3.2 mmol) at room temperature. After stirring for 15 h, excess solvent was removed using reduced pressure, and the remaining residue was dissolved in a 3:1 MeOH/3N NaOH solution (100 mL) and heated at reflux for 2 h. MeOH was removed from the solution using reduced pressure until a white solid material appeared. The solid was filtered to give compound 18 (0.68 g). $^1$H NMR (400 MHz, CD$_3$OD) δ 8.06 (d, J=8 Hz, 1H), 8.05 (s, 1H), 7.33–7.45 (m, 4H), 7.10–7.21 (m, 5H), 3.76 (s, 2H), 3.56 (qn, J=8 Hz, 1H), 2.96 (t, J=12 Hz, 2H), 2.73 (dd, J=8 Hz, J=12 Hz, 1H), 2.54 (dd, J=8 Hz, J=12 Hz, 1H), 2.14–2.40 (m, 4H), 1.74 (td, J=4 Hz, J=12 Hz, 1H), 1.50–1.58 (m, 3H), ESI (MH$^+$) m/z 425.

6.19. Example 19

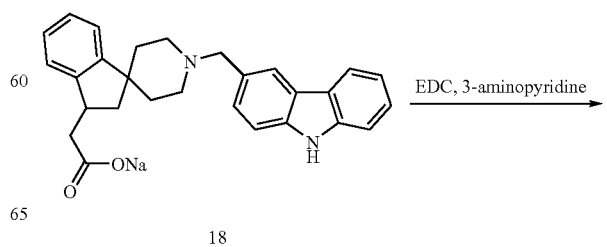

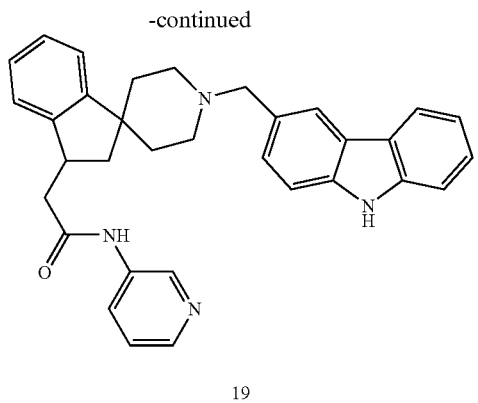

19

EDC (20 mg, 0.11 mmol) was added to a CH$_2$Cl$_2$ solution (1 mL) containing carboxylic acid 18 (30 mg, 0.07 mmol) and the corresponding 3-aminopyridine (0.35 mmol) at room temperature. After stirring for 24 h, the solvent was removed and the remaining residue (compound 19) was purified using preparative reverse phase HPLC. $^1$H NMR (400 MHz, CD$_3$OD) δ 9.41 (s, 1H), 8.54 (d, J=6 Hz, 1H), 8.47 (m, 1H), 8.25 (s, 1H), 8.10 (d, J=8 Hz, 1H), 7.97 (dd, J=6 Hz, J=8 Hz, 1H), 7.48–7.62 (m, 3H), 7.43 (t, J=8 Hz, 1H), 7.19–7.26 (m, 5H), 4.51 (s, 2H), 3.79 (qn, J=8 Hz, 1H), 3.60 (d, J=12 Hz, 1H), 3.54 (d, J=12 Hz, 1H), 3.24 (t, J=12 Hz, 1H), 3.11 (dd, J=8 Hz, J=12 Hz, 1H), 2.72 (dd, J=8 Hz, J=12 Hz, 1H), 2.61 (dd, J=8 Hz, J=12 Hz, 1H), 2.41 (td, J=4 Hz, J=12 Hz, 1H), 1.93 (td, J=4 Hz, J=12 Hz, 1H), 1.73–1.83 (m, 3H); ESI (MH$^+$) m/z 501.

6.20. Example 20

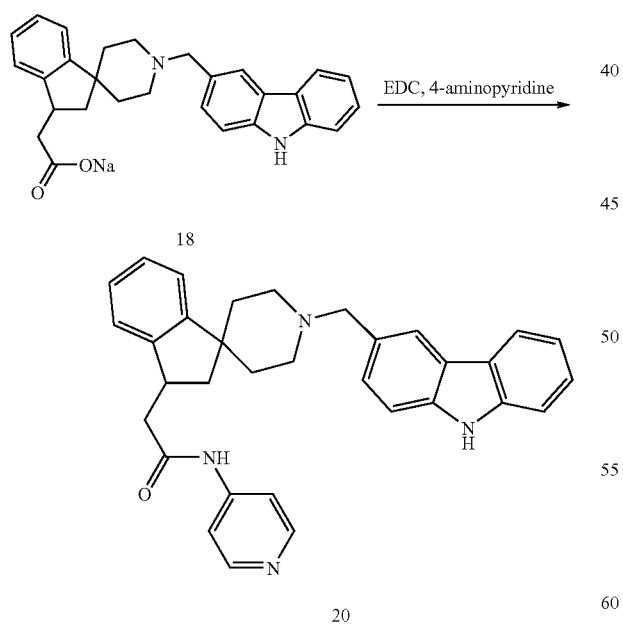

Compound 20 was synthesized following the procedure described in Example 19, substituting 4-aminopyridine for 3-aminopyridine. The desired product was isolated by reverse phase HPLC. $^1$H NMR (400 MHz, CD$_3$OD) δ 8.63 (d, J=8 Hz, 2H), 8.25 (s, 1H), 8.20 (d, J=8 Hz, 2H), 8.10 (d, J=8 Hz, 1H), 7.49–7.57 (m, 3H), 7.43 (t, J=8 Hz, 1H), 7.18–7.26 (m, 5H), 4.52 (s, 2H), 3.80 (qn, J=8 Hz, 1H), 3.58 (t, J=12 Hz, 2H), 3.15–3.36 (m, 2H), 2.65–2.78 (m, 2H), 2.41 (td, J=4 Hz, J=12 Hz, 1H), 1.93 (td, J=4 Hz, J=12 Hz, 1H), 1.72–1.84 (m, 3H); ESI (MH$^+$) m/z 501.

6.21. Example 21

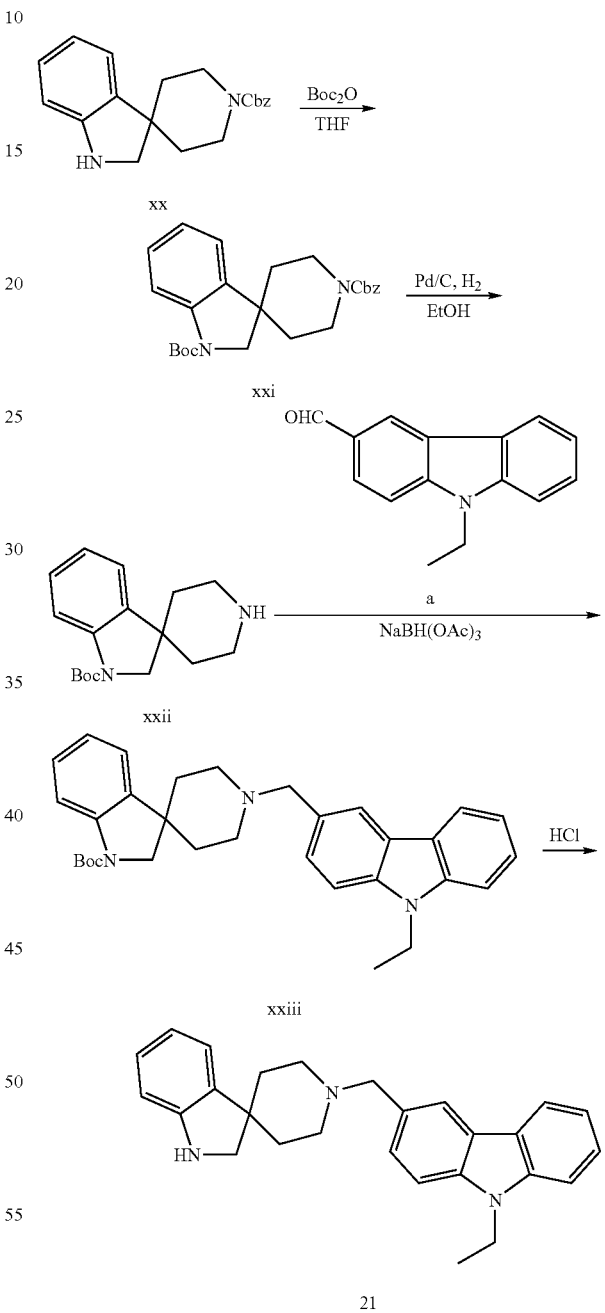

100 mg (0.45 mmol) di-t-butyl dicarbonate was added to a THF solution of amine xx (143 mg, 0.44 mmol). The reaction was stirred overnight followed by removal of solvent. The desired product (xxi) was isolated by silica gel chromatography (150 mg). Amine xxi was dissolved in ethanol followed by addition of 20 mg of Pd/C. The reaction was stirred at room temperature under 1 atm of hydrogen.

After 2 h, the Pd/C was removed by filtration through a Celite pad. Amine xxii was directly used for next reaction without purification.

Compound 21 was synthesized from compound xxii following the procedure described in Example 1, step 5, followed by 2 N HCl treatment. $^1$H NMR (400 MHz, CDCl$_3$) δ 8.31 (s, 1H), 8.15 (d, J=7.8 Hz, 1H), 7.66 (d, J=8.4 Hz, 1H), 7.61 (dd, J=1.3, 8.4 Hz, 1H), 7.57 (d, J=8.2 Hz, 1H), 7.52 (t, J=7.0 Hz, 1H), 4.57 (s, 2H), 4.49 (q, J=7.2, 2H), 3.87 (s, 2H), 3.64 (d, J=10.9, 2H), 3.28 (dd, J=2.0, 11.5 Hz, 2H), 2.23 (dt, J=3.8, 14.3 Hz, 2H), 2.05 (d, J=14.6, 2H), 1.41 (t, J=7.2, 3H); ESI (MH$^+$) m/z 501.

6.22. Example 22

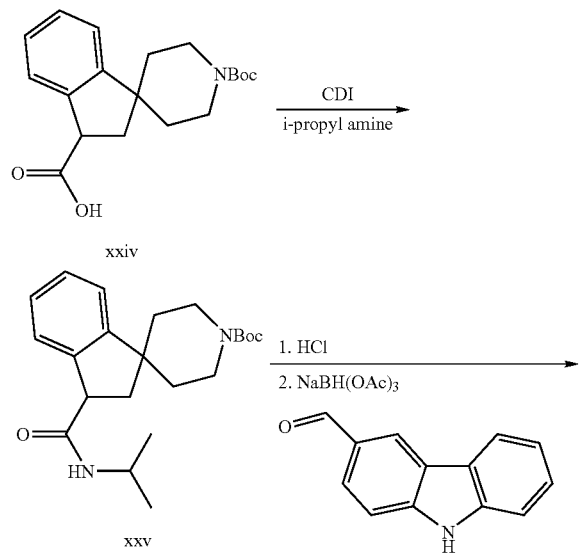

Step 1: CDI (25 mg, 0.15 mmol) was added to a CH$_2$Cl$_2$ solution (1 mL) containing carboxylic acid (50 mg, 0.15 mmol). The reaction was stirred overnight at room temperature followed by addition of 200 μL of isopropyl amine. The desired amide was isolated by flash silica gel chromatography. Compound 22 was synthesized according to the procedure described in Example 1, step 5, replacing 9-ethyl-9H-carbazole-3-carboxaldehyde (a) with 9H-carbazole-3-carboxaldehyde (b). $^1$H NMR (400 MHz, CDCl$_3$) δ 10.9 (br s, 1), 9.55 (br s, 1H), 8.04 (s, 1H), 8.05, (d, J=7.9 Hz, 1H), 7.42 (t, J=10.3 Hz, 1H), 7.38 (t, J=7.9 Hz, 1H), 7.30 (s, 1H), 7.24 (m, 6H), 5.70 (s, 1H), 4.14 (dd, J=3.1, 10.7 Hz, 2H), 4.07 (m, 1H), 3.81 (t, J=7.7 Hz, 1H), 3.28 (t, J=10.9 Hz, 2H), 2.54 (m, 3H), 2.25 (m, 5H), 1.64 (d, J=13.6 Hz, 1H), 1.43 (d, J=13.6 Hz, 1H), 1.13 (d, J=6.6 Hz, 1H), 1.07 (d, J=6.6 Hz, 3H); ESI (MH$^+$) m/z 452.

6.23. Example 23

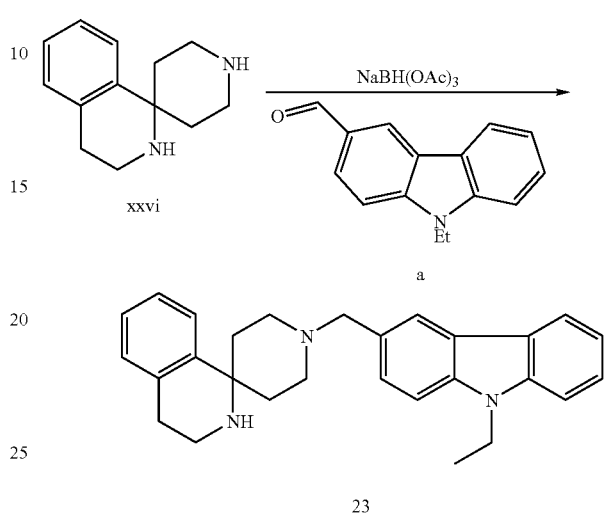

Compound 23 was synthesized from compound xxvi following the procedure described in Example 1, step 5. The desired product was isolated by silica gel column chromatography eluted with 10–20% MeOH and methylene chloride. $^1$H NMR (400 MHz, CDCl$_3$) δ 8.12 (d, J=7.8 Hz, 1H), 8.10 (s, 1H), 7.38–7.49 (m, 5H), 7.04–7.26 (m, 4H), 4.38 (q, J=7.2 Hz, 2H), 3.86 (br, s, 2H), 3.69–3.72 (m, 2H), 3.03–3.06 (m, 2H), 2.90 (br, s, 2H), 2.74–2.77 (m, 2H), 2.25 (br, s, 1H), 1.68–1.73 (m, 2H), 1.44 (t, J=7.2 Hz, 3H); ESI (MH$^+$) m/z 410.

6.24. Example 24

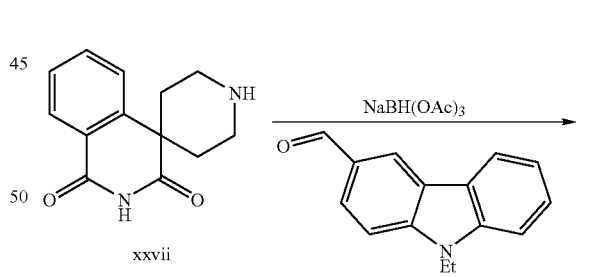

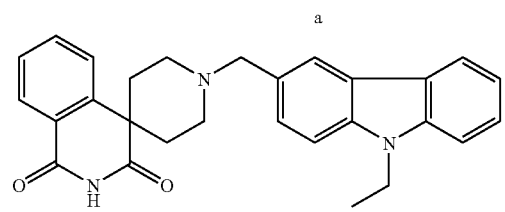

Compound 24 was synthesized from amine xxvii following the procedure described in Example 1, step 5. The desired product was isolated by silica gel column chromatography eluted with 10–20% MeOH and methylene chloride. $^1$H NMR (400 MHz, CDCl$_3$) δ 8.32 (br, s, 1H), 8.21 (d, J=7.4 Hz, 1H), 8.10–8.13 (m, 2H), 7.40–7.72 (m, 7H), 7.23 (t, J=7.6 Hz, 1H), 4.37 (q, J=7.2 Hz, 2H), 3.86 (br, s, 2H), 2.94 (br, s, 2H), 2.35 (br, s, 2H), 2.01–2.10 (m, 2H), 1.44 (t, J=7.2 Hz, 3H); ESI (MH$^+$) m/z 438.

6.25. Example 25

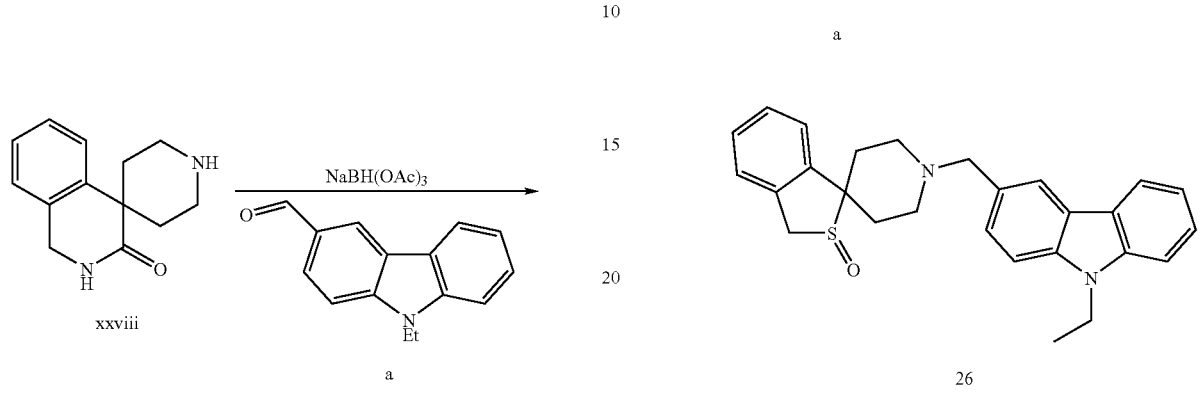

Compound 25 was synthesized from amine xxviii following the procedure described in Example 1, step 5. The desired product was isolated by silica gel column chromatography eluted with 10–20% MeOH and methylene chloride. $^1$H NMR (400 MHz, CDCl$_3$) δ 8.05–8.12 (m, 3H), 7.35–7.52 (m, 7H), 7.23 (t, J=6.9 Hz, 1H), 6.76 (br, s, 1H), 5.50–5.80 (br, m, 2H), 4.37 (q, J=7.2 Hz, 2H), 3.77 (br, s, 2H), 3.53 (br, s, 2H), 2.88–2.92 (m, 2H), 2.12–2.34 (m, 4H), 1.79–1.82 (m, 2H), 1.44 (t, J=7.2 Hz, 3H); ESI (MH$^+$) m/z 424.

6.26. Example 26

Compound 26 was synthesized from amine xxix following the procedure described in Example 1, step 5. The desired product was isolated by silica gel column chromatography eluted with 10–20% MeOH and methylene chloride. $^1$H NMR (400 MHz, CDCl$_3$) δ 8.15 (s, 1H), 8.11 (d, J=7.7 Hz, 1H), 7.26–7.55 (m, 9H), 4.30–4.53 (m, 4H), 4.40 (q, J=7.2 Hz, 2H), 4.10–4.18 (m, 1H), 3.63–3.81 (br, m, 2H), 3.17–3.32 (m, 2H), 2.61–2.90 (m, 2H), 1.87–1.91 (m, 1H), 1.45 (t, J=7.2 Hz, 3H); ESI (MH$^+$) m/z 429.

6.27. Example 27

Compound 27 was synthesized from amine xxx following the procedure described in Example 1, step 5. The desired product was isolated by silica gel column chromatography eluted with 10–20% MeOH and methylene chloride. $^1$H NMR (400 MHz, CDCl$_3$) δ 8.11–8.13 (m, 2H), 7.62 (br, s, 1H), 7.39–7.49 (m, 4H), 7.17–7.25 (m, 3H), 7.02 (t, J=7.4 Hz, 1H), 6.86 (d, 7.7 Hz, 1H) 4.38 (q, J=7.2 Hz, 2H), 3.91 (br, m, 2H), 2.85–3.04 (br, m, 4H), 2.05 (br, m, 2H), 1.77 (br, m, 2H) 1.44 (t, J=7.2 Hz, 3H); ESI (MH$^+$) m/z 410.

6.28. Example 28

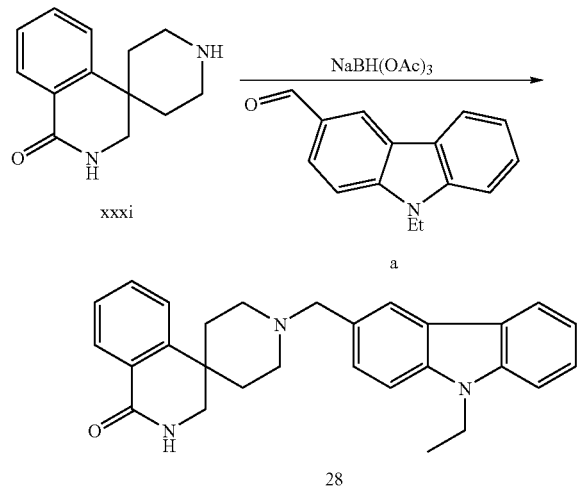

Compound 28 was synthesized from amine xxxi following the procedure described in Example 1, step 5. The desired product was isolated by silica gel column chromatography eluted with 10–20% MeOH and methylene chloride. $^1$H NMR (400 MHz, CDCl$_3$) δ 8.49 (br, s, 1H), 8.12 (s, 1H), 7.99–8.09 (m, 3H), 7.24–7.57 (m, 7H), 4.44 (s, 2H), 4.36 (q, J=7.2 Hz, 2H), 3.52–3.63 (m, 4H), 2.96–2.99 (m, 2H), 2.52–2.58 (m, 2H), 1.93–1.96 (m, 2H), 1.42 (t, J=7.2 Hz, 3H); ESI (MH$^+$) m/z 424.

6.29. Example 29

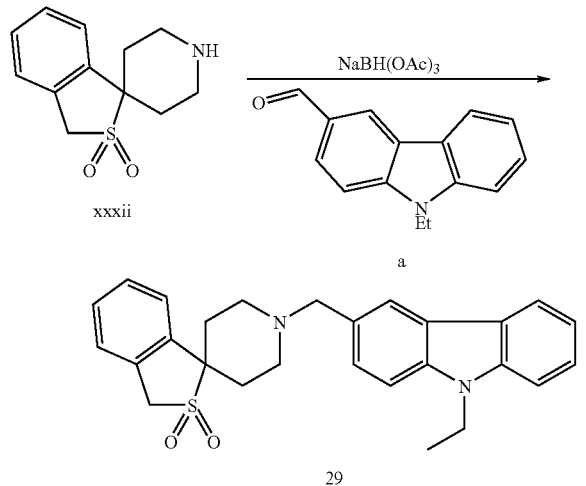

Compound 29 was synthesized from amine xxxii following the procedure described in Example 1, step 5. The desired product was isolated by silica gel column chromatography eluted with 10–20% MeOH and methylene chloride. $^1$H NMR (400 MHz, CDCl$_3$) δ 8.18 (s, 1H), 8.10 (d, J=7.2 Hz, 1H), 7.19–7.57 (m, 9H), 4.40 (s, 2H), 4.39 (q, J=7.1 Hz, 2H), 3.61–3.64 (m, 2H), 3.37–3.39 (br, m, 2H), 2.78–2.85 (m, 2H), 2.49–2.53 (m, 2H), 2.28 (br, m, 2H), 1.45 (t, J=7.1 Hz, 3H); ESI (MH$^+$) m/z 445.

6.30. Example 30

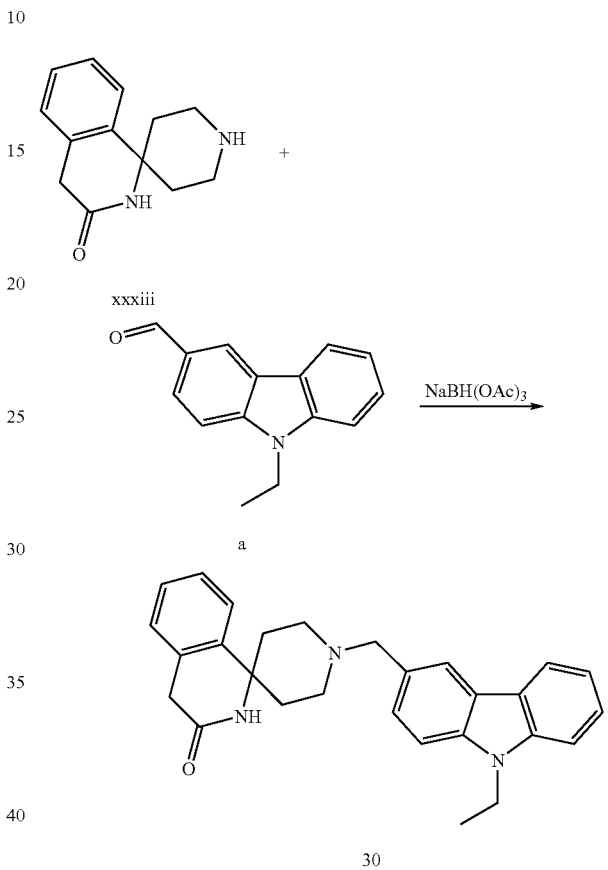

Compound 30 was synthesized from amine xxxiii following the procedure as described in Example 1, step 5. The desired product was isolated by silica gel column chromatography eluted with 10–20% MeOH and methylene chloride. $^1$H NMR (400 MHz, CDCl$_3$) δ 8.12 (d, J=7.7 Hz, 1H), 8.02 (s, 1H), 7.24–7.51 (m, 8H), 7.15 (d, J=7.0 Hz, 1H), 6.47 (br, s, 1H), 4.38 (q, J=7.2 Hz, 2H), 3.78 (br, s, 2H), 3.64 (br, s, 2H), 2.99–3.01 (m, 2H), 2.26–2.35 (m, 4H), 1.78–1.81 (m, 2H), 1.43 (t, J=7.2 Hz, 3H); ESI (MH$^+$) m/z 424.

6.31. Example 31

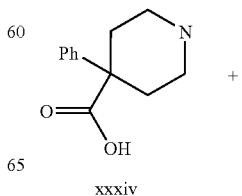

-continued

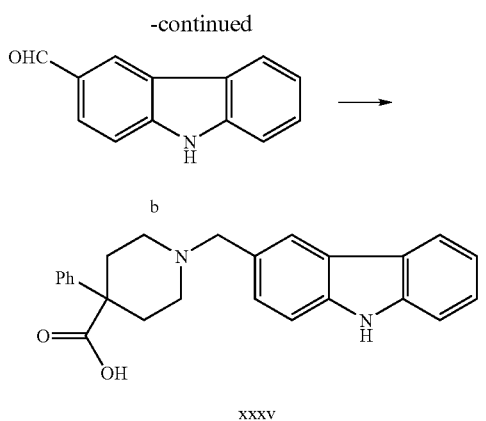

xxxv

Step 1: 4-Phenyl-4-piperidine-carboxylic acid p-methyl benzenesulfonate (xxxiv) (5.3 mmol) was mixed with 9H-carbazole-3-carboxyaldehyde (b) (1.03 g, 5.3 mmol) and NaBH(OAc)$_3$ (2.24 g, 10.5 mmol) in 1,2-dichloroethane (20 mL). The medium was brought to neutral by the addition of 740 μL (5.3 mmol) of triethylamine. After stirring at room temperature overnight and at 80° C. for 2 h, the majority of dichloroethane was removed under vacuum. The mixture was added 2 mL of methanol and 40 mL of ether. The precipitate was filtered. The solid was washed with ether twice and water twice. Then the solid was again washed with ether twice and dried under vacuum to yield carboxylic acid xxxv as a white solid (1.5 g).

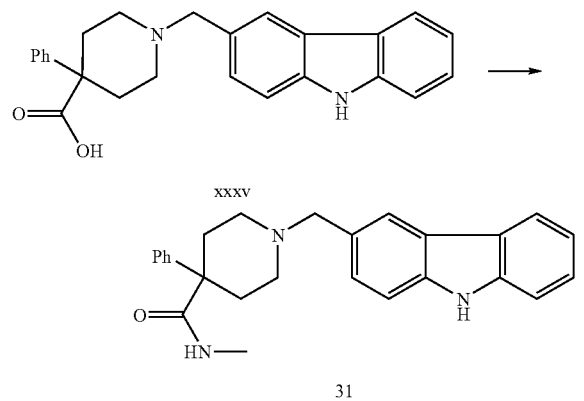

Step 2: Carboxylic acid xxxv (20 mg, 0.05 mmol) in DMF (700 μL) was stirred with 52 μL of methyl amine in THF (2.0M, 0.1 mmol) and HBTU (0.05 mmol) for 6 h at room temperature. The reaction mixture was treated with 500 μL of DMSO and 20 μL of water, and purified by reverse phase HPLC. Lyophilizer removal of water afforded compound 31 as a white solid (15 mg). $^1$H NMR (CD$_3$OD): δ 8.26 (s, 1H), 8.12 (d, J=8.0 Hz, 1H), 7.77 (m, 1H), 7.58 (d, J=8.5 Hz, 1H), 7.51 (dd, J=8.5, 14 Hz, 4H), 7.45 (m, 2H), 7.37 (m, 4H), 7.31 (m, 1H), 7.24 (t, J=7.5 Hz, 2H), 4.54 (s, 2H), 3.63 (d, J=13 Hz, 2H), 3.26 (d, J=12.5 Hz, 2H), 2.85 (d, J=14 Hz, 2H), 2.79 (d, J=4 Hz, 3H), 2.08 (dt, J=3, 13.5 Hz, 2H). MS (ES): 398 [M+H].

6.32. Example 32

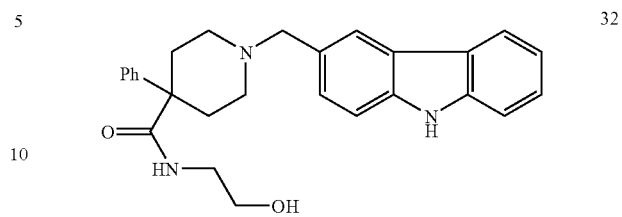

Compound 32 was prepared following the procedure described in Example 31, step 2, substituting ethanolamine for methyl amine. The reaction mixture was purified by reverse phase HPLC. The desired product was obtained after lyophilizer removal of water as a white solid (14 mg). $^1$H NMR (CD$_3$OD): δ 8.26 (s, 1H), 8.12 (d, J=8.0 Hz, 1H), 7.77 (m, 1H), 7.58 (d, J=8.5 Hz, 1H), 7.55 (m, 2H), 7.52 (d, J=8.5 Hz, 2H), 7.46 (m, 2H), 7.38 (m, 4H), 7.30 (m, 1H), 7.24 (t, J=7.5 Hz, 2H), 4.53 (s, 2H), 3.63 (d, J=13 Hz, 2H), 3.58 (t, J=6 Hz, 2H), 3.46 (t J=6 Hz, 1H), 3.34 (m, 2H), 3.20 (m, 1H), 3.03 (m, 1H), 2.87 (d, J=15 Hz, 2H), 2.09 (dt, J=3, 13.5 Hz, 2H). MS (ES): 428 [M+H].

6.33. Example 33

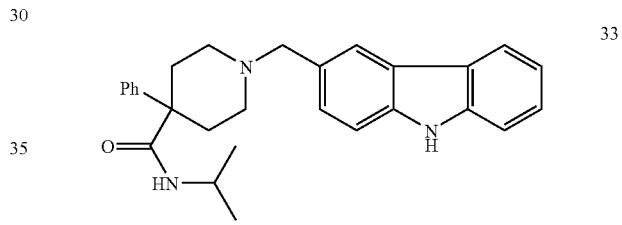

Compound 33 was prepared following the procedure described in Example 1, step 2, substituting isopropylamine for methyl amine. The reaction mixture was purified by reverse phase HPLC. The desired product was obtained after lyophilizer removal of water as a white solid (15 mg). $^1$H NMR (CD$_3$OD): δ 8.26 (s, 1H), 8.12 (d, J=8.0 Hz, 1H), 7.58 (d, J=8.5 Hz, 1H), 7.56 (m, 2H), 7.51 (d, J=8.5 Hz, 2H), 7.45 (m, 3H), 7.38 (m, 4H), 7.30 (m, 1H), 7.25 (t, J=7.5 Hz, 2H), 4.55 (s, 2H), 4.03(sep, J=7 Hz, 1H), 3.64 (d, J=13 Hz, 2H), 3.26 (t J=12 Hz, 2H), 3.04 (m, 1H), 3.02 (m, 1H), 2.86 (d, J=13.5 Hz, 2H), 2.09 (dt, J=3, 13.5 Hz, 2H), 1.03 (d, J=7.0 Hz, 3H). MS (ES): 426 [M+H].

6.34. Example 34

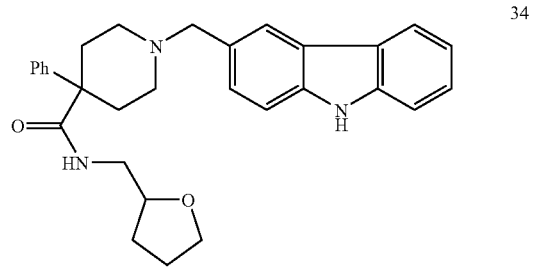

Compound 34 was prepared following the procedure described in Example 1, step 2, substituting tetrahydrofurftirylamine for methyl amine. The reaction mixture was purified by reverse phase HPLC. The desired product was obtained after lyophilizer removal of water as a white solid (12 mg). $^1$H NMR (CD$_3$OD): δ 8.25 (s, 1H), 8.12 (d, J=8.0 Hz, 1H), 7.72 (s, br, 1H), 7.56 (d, J=8.0 Hz, 1H), 7.58 (m, 1H), 7.51 (d, J=8.5 Hz, 2H), 7.38 (m, 4H), 7.30 (m, 1H), 7.24 (t, J=7.5 Hz, 2H), 4.53 (s, 2H), 3.83 (m, J=7 Hz, 1H), 3.63 (m, 5H), 3.30(m, 1H), 3.23 (t J=6 Hz, 2H), 2.88 (d, J=14.5 Hz, 1H), 2.10 (m, 1H), 1.70 (m, 4H), 1.35 (m, 1H). MS (ES): 468 [M+H].

6.35. Example 31

The compounds provided in FIG. 1 were evaluated using a functional cell-based assay (for example, using HEK 293 cells expressing recombinant hMCHR2). Ca$^{2+}$ mobilization was measured using a Fluorometric Imaging Plate Reader (FLIPR) system (Molecular Devices). The compounds displayed potencies of 10 μM or less.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of formula:

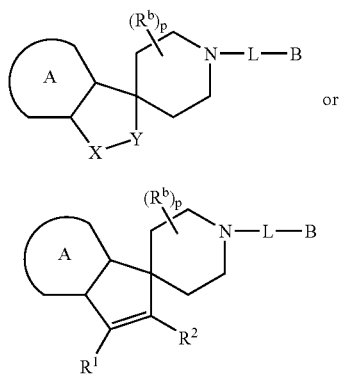

or a pharmaceutically acceptable salt, hydrate, solvate or prodrug thereof, wherein A represents a substituted or unsubstituted benzene ring ring;

B is substituted or unsubstituted carbazolyl;

L is (C$_1$–C$_4$)alkylene;

X and Y are each independently CH or CH2 wherein the C is optionally substituted with —OR$^3$, —N(R$^3$)COR$^4$, —C(O)NR$^3$R$^4$, —N(R$^3$)CO$_2$R$^4$, —N(R$^3$)C(O)N(R$^4$)R$^5$, or —(O);

R$^1$ and R$^2$ are independently selected from the group consisting of H, (C$_1$–C$_4$)alkyl, (C$_2$–C$_8$)alkenyl, (C$_2$–C$_8$)alkynyl, (C$_1$–C$_8$)heteroalkyl, aryl, aryl(C$_1$–C$_4$) alkyl, —NR$^6$C(O)R$^5$, —C(O)R$^5$ and —NR$^5$C(O)NHR$^6$;

each R$^b$ is selected from the group consisting of (C$_1$–C$_4$) alkyl, aryl, OR$^7$, C(O)R$^7$ and C(O)NR$^7$R$^8$;

R$^3$ and R$^4$ are independently selected from the group consisting of H, (C$_1$–C$_8$)alkyl, hetero(C$_1$–C$_8$)alkyl, aryl, aryl(C$_1$–C$_4$)alkyl, C(O)R', CO$_2$R' and C(O) NR'R";

R$^5$, R$^6$, R$^7$ and R$^8$ are independently selected from the group consisting of H, (C$_1$–C$_8$)alkyl, C(O)R''', CO$_2$R''', aryl and aryl(C$_1$–C$_4$)alkyl;

optionally, R$^7$ and R$^8$ may be combined with the nitrogen to which each is attached to form a 5-, 6- or 7-membered ring;

R', R" and R''' are independently selected from the group consisting of H, (C$_1$–C$_8$)alkyl, aryl and aryl(C$_1$–C$_4$) alkyl; and the subscript p is an integer of from 0 to 4.

2. The compound of claim 1, wherein the subscript p is 0.

3. The compound of claim 1, wherein B is substituted or unsubstituted 3-carbazolyl.

4. The compound of claim 1, having the formula (IV):

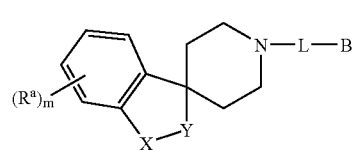

wherein:

each R$^a$ is independently selected from the group consisting of halogen, halo(C$_1$–C$_4$)alkyl, (C$_1$–C$_4$)alkoxy, aryl (C$_1$–C$_4$)alkyl, OC(O)R$^{17}$, NR$^{17}$R$^{18}$, SR$^{17}$, cyano, nitro, CO$_2$R$^{17}$, CONR$^{17}$R$^{18}$, C(O)R$^{17}$, OC(O)NR$^{17}$R$^{18}$, NR$^{18}$C(O)R$^{17}$, NR$^{18}$CO$_2$R$^{17}$, NR$^{19}$C(O)NR$^{17}$R$^{18}$, S(O)$_k$R$^{17}$, S(O)$_k$NR$^{17}$R$^{18}$, N$_3$, (C$_4$–C$_8$)cycloalkyl, (C$_5$–C$_8$)cycloalkenyl, aryl and heteroaryl, and the subscript k is an integer of from 1 to 2;

R$^{17}$, R$^{18}$ and R$^{19}$ are independently selected from the group consisting of H, (C$_1$–C$_8$)alkyl, (C$_1$–C$_8$)heteroalkyl, aryl(C$_1$–C$_4$)alkyl and aryl; and the subscript m is an integer of from 0 to 4.

5. The compound of claim 4, wherein X or Y is CH, wherein the C is substituted with —OH.

6. The compound of claim 4, wherein Y is CH, wherein the C substituted with —OH.

7. The compound of claim 4, wherein X is CH, wherein the C is substituted with —N(R$^3$)COR$^4$.

8. The compound of claim 4, wherein X is CH, wherein the C is substituted with —N(R$^3$)COR$^4$ and Y is —C$_1$ alkylene-substituted with —OH.

9. The compound of claim 1 having the formula (V):

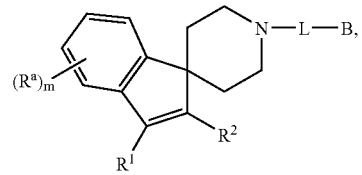

wherein:

each R$^a$ is independently halogen, halo(C$_1$–C$_4$)alkyl, (C$_1$–C$_4$)alkoxy, aryl(C$_1$–C$_4$)alkyl, OC(O)R$^{17}$, NR$^{17}$R$^{18}$, SR$^{17}$, cyano, nitro, CO$_2$R$^{17}$, CONR$^{17}$R$^{18}$, C(O)R$^{17}$, OC(O)NR$^{17}$R$^{18}$, NR$^{18}$C(O)R$^{17}$, NR$^{18}$CO$_2$R$^{17}$, NR$^{19}$C(O)NR$^{17}$R$^{18}$, S(O)$_k$R$^{17}$, S(O)$_k$NR$^{17}$R$^{18}$, N$_3$, (C$_4$–C$_8$)cycloalkyl, (C$_5$–C$_8$)cycloalkenyl, aryl or heteroaryl, wherein R$^{17}$, R$^{18}$ and R$^{19}$ are independently selected from the group consisting of H, (C$_1$–C$_8$)alkyl, (C$_1$–C$_8$)heteroalkyl, aryl(C$_1$–C$_4$)alkyl and aryl, and the subscript k is an integer of from 1 to 2; and the subscript m is an integer of from 0 to 4.

10. The compound of claim 9, wherein R$^1$ and R$^2$ are H.

11. The compound of claim 1, having the formula:

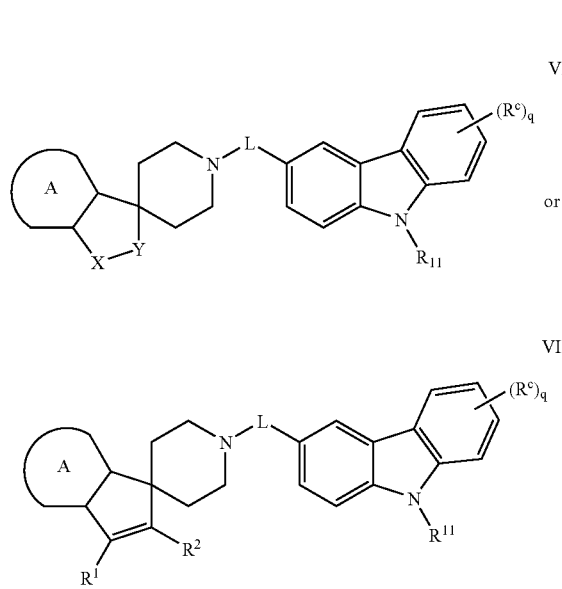

wherein

R$^{11}$ is selected from the group consisting of H, (C$_1$–C$_4$) alkyl, (C$_2$–C$_8$)alkenyl, (C$_2$–C$_8$)alkynyl, (C$_1$–C$_8$)heteroalkyl, aryl, aryl(C$_1$–C$_4$)alkyl, heteroaryl, heteroaryl (C$_1$–C$_4$)alkyl, (C$_3$–C$_8$)cycloalkyl, (C$_5$–C$_8$)cycloalkenyl, (C$_3$–C$_8$)cycloalkyl-alkyl, (C$_3$–C$_8$) cycloheteroalkyl, (C$_3$–C$_8$)cycloheteroalkyl-alkyl, C(O) R$^{12}$, CO$_2$R$^{12}$, C(O)NR$^{12}$R$^{13}$, S(O)$_k$R$^{12}$ and S(O)$_k$ NR$^{12}$R$^{13}$;

each R$^c$ is independently selected from the group consisting of (C$_1$–C$_8$)alkyl, (C$_2$–C$_8$)alkenyl, (C$_2$–C$_8$)alkynyl, (C$_1$–C$_8$)heteroalkyl, halo(C$_1$–C$_8$)alkyl, halogen, CN, NO$_2$, OR$^{14}$, SR$^{14}$, NR$^{14}$R$^{15}$, (C$_3$–C$_8$)cycloalkyl, (C$_5$–C$_8$)cycloalkenyl, (C$_3$–C$_8$)cycloalkyl-alkyl, (C$_3$–C$_8$)cycloheteroalkyl, (C$_3$–C$_8$)cycloheteroalkyl-alkyl, C(O)R$^{14}$, CO$_2$R$^{14}$, C(O)NR$^{14}$R$^{15}$, aryl, aryl (C$_1$–C$_4$)alkyl, heteroaryl, heteroaryl(C$_1$–C$_4$)alkyl, S(O)$_k$ R$^{14}$, S(O)$_k$NR$^{14}$R$^{15}$, N(R$^{15}$)S(O)$_k$R$^{14}$, OC(O) R$^{14}$, OCO$_2$R$^{14}$, OC(O)NR$^{14}$R$^{15}$, N(R$^{16}$)C(O)NR$^{14}$R$^{15}$, N(R$^{15}$)C(O)R$^{14}$ and N(R$^{15}$)CO$_2$R$^{14}$;

R$^{12}$, R$^{13}$, R$^{14}$, R$^{15}$ and R$^{16}$ are independently selected from the group consisting of H, (C$_1$–C$_8$)alkyl, (C$_1$–C$_8$) heteroalkyl, aryl(C$_1$–C$_4$)alkyl and aryl;

the subscript q is an integer of from 0 to 7; and the subscript k is an integer of from 1 to 2.

12. The compound of claim 11, having the formula:

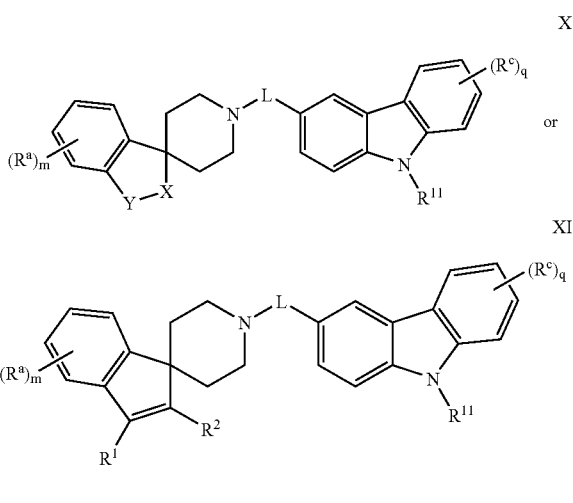

wherein each R$^a$ is independently selected from the group consisting of halogen, halo(C$_1$–C$_4$)alkyl, (C$_1$–C$_4$)alkoxy, aryl (C$_1$–C$_4$)alkyl, OC(O)R$^{17}$, NR$^{17}$R$^{18}$, SR$^{17}$, cyano, nitro, CO$_2$R$^{17}$, CONR$^{17}$R$^{18}$, C(O)R$^{17}$, OC(O)NR$^{17}$R$^{18}$, NR$^{18}$C(O)R$^{17}$, NR$^{18}$CO$_2$R$^{17}$, NR$^{19}$C(O)NR$^{17}$R$^{18}$, S(O)$_k$R$^{17}$, S(O)$_k$NR$^{17}$R$^{18}$, N$_3$, (C$_4$–C$_8$)cycloalkyl, (C$_5$–C$_8$)cycloalkenyl, aryl and heteroaryl;

R$^{17}$, R$^{18}$ and R$^{19}$ are independently selected from the group consisting of H, (C$_1$–C$_8$)alkyl, (C$_1$–C$_8$)heteroalkyl, aryl(C$_1$–C$_4$)alkyl and aryl;

the subscript m is an integer of from 0 to 4; and each subscript k is an integer of from 1 to 2.

13. The compound of any one of claims 1, 9 and 12, wherein L is methylene.

14. The compound of claim 12, having the formula (Xa):

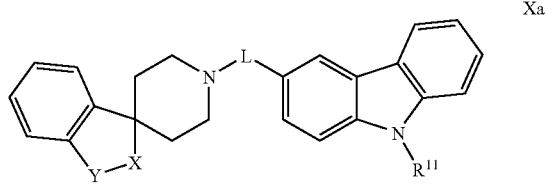

wherein

L is methylene; and

X and Y are independently selected from —(C$_1$–C$_2$) alkylene-, wherein C$_1$ or C$_2$ is optionally subtituted with —OR$^3$, —N(R$^3$)COR$^4$, —C(O)NR$^3$R$^4$ or —N(R$^3$)C(O)N(R$^4$)R$^5$.

15. The compound of claim 14, having a formula selected from the group consisting of:

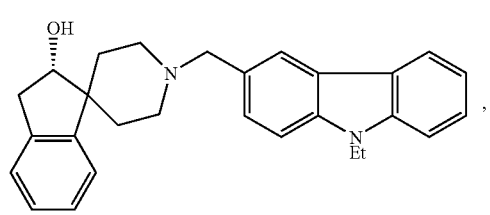

-continued
6
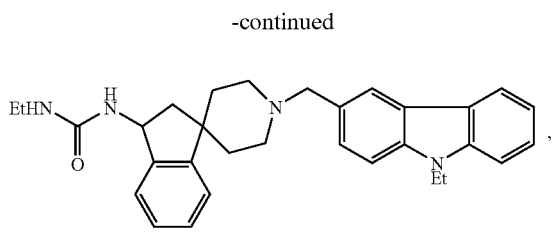
7
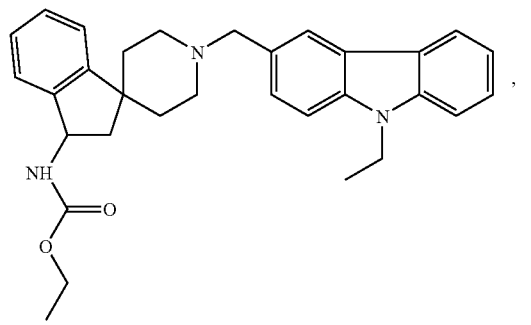
9
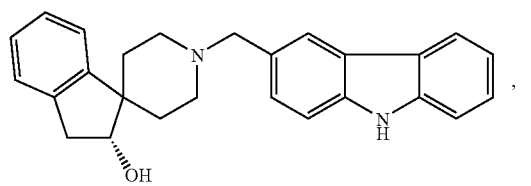
10
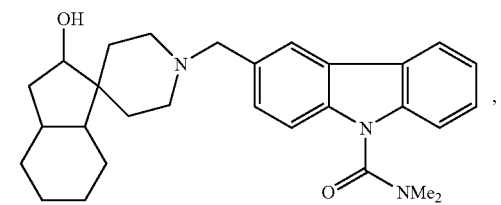
11
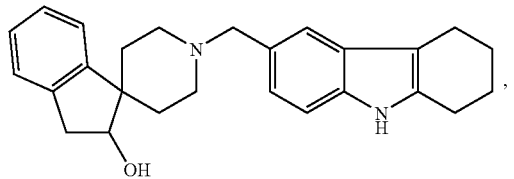
13
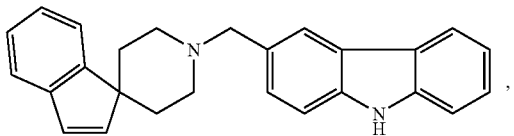
14
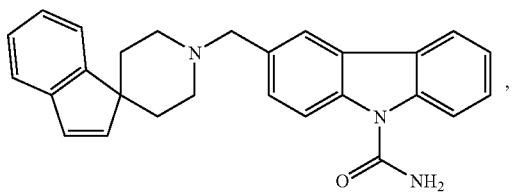
-continued
15
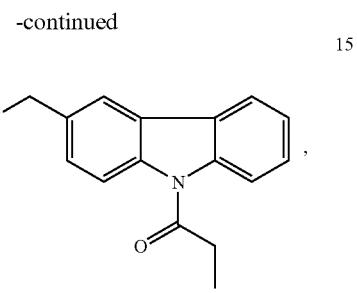
16
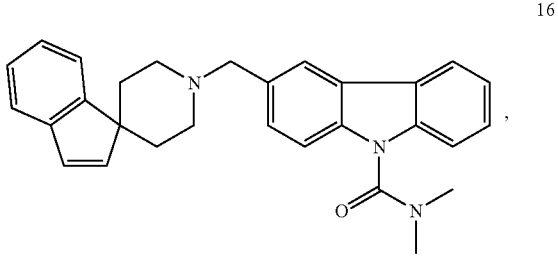
17
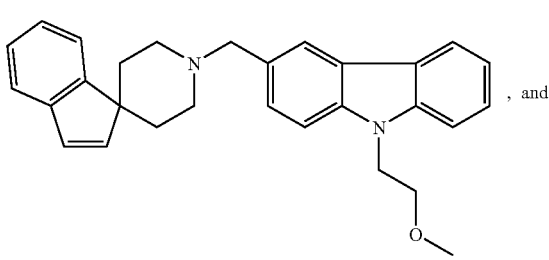
22
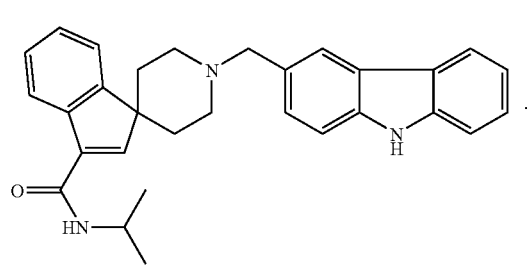
, and
.
16. A compound of formula:
VII
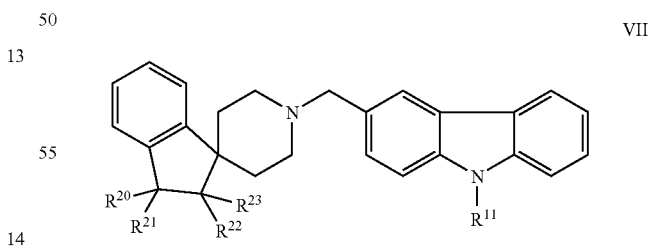
or a pharmaceutically acceptable salt, hydrate, solvate or prodrug thereof, wherein
$R^{20}$ and $R^{23}$ independently represent H or $OR^3$;
$R^{21}$ and $R^{22}$ independently represent H, $OR^3$, $N(R^3)COR^4$, $C(O)NR^3R^4$, $N(R^3)CO_2R^4$, $N(R^3)C(O)N(R^4)R^5$, $N(R^3)R^4$, $C(O)N(R^3)R^4$, $N(R^3)C(O)R^4$, $(CH_2)C(O)N(R^3)(R^4)$, $(CH_2)CO_2R^3$, or $(C_1–C_4)$alkyl;

$R^{11}$ represents H, $(C_1$–$C_4)$alkyl, $(C_2$–$C_8)$alkenyl, $(C_2$–$C_8)$alkynyl, $(C_1$–$C_8)$heteroalkyl, aryl, aryl$(C_1$–$C_4)$alkyl, heteroaryl, heteroaryl$(C_1$–$C_4)$alkyl, $(C_3$–$C_8)$cycloalkyl, $(C_5$–$C_8)$cycloalkenyl, $(C_3$–$C_8)$cycloalkyl-alkyl, $(C_3$–$C_8)$cycloheteroalkyl, $(C_3$–$C_8)$cycloheteroalkyl-alkyl, $C(O)R^{12}$, $CO_2R^{12}$, $C(O)NR^{12}R^{13}$, $S(O)_kR^{12}$ or $S(O)_kNR^{12}R^{13}$, and the subscript k is an integer of from 1 to 2;

$R^{12}$ and $R^{13}$ independently represent H, $(C_1$–$C_8)$alkyl, $(C_1$–$C_8)$heteroalkyl, aryl$(C_1$–$C_4)$alkyl or aryl;

$R^3$ and $R^4$ independently represent H, $(C_1$–$C_8)$alkyl, hetero$(C_1$–$C_8)$alkyl, aryl, aryl$(C_1$–$C_4)$alkyl, $C(O)R'$, $CO_2R'$ or $C(O)NR'R''$; and R', R" and R'" are independently selected from the group consisting of H, $(C_1$–$C_8)$alkyl, aryl and aryl$(C_1$–$C_4)$alkyl.

17. The compound of claim 16, wherein $R^{20}$ and $R^{23}$ each represent H, $R^{22}$ represents OH, and $R^{21}$ represents $N(R^3)C(O)R^4$.

18. The compound of claim 16, wherein $R^{20}$ represents OH, and $R^{22}$ and $R^{23}$ each represent H, and $R^{21}$ represents $C_2$ alkyl.

19. The compound of claim 16, wherein $R^{20}$, $R^{22}$, and $R^{23}$ each represent H and $R^{21}$ represents $N(R^3)C(O)R^4$.

20. The compound of claim 16, wherein $R^{20}$, $R^{22}$, and $R^{23}$ each represent H and $R^{21}$ represents $(CH_2)CO_2R^3$.

21. The compound of claim 16, wherein $R^{20}$, $R^{22}$, and $R^{23}$ each represent H and $R^{21}$ represents $(CH_2)C(O)N(R^3)(R^4)$.

22. The compound of claim 16, having a formula that is selected from the group consisting of:

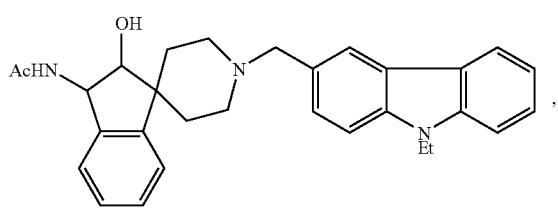

2

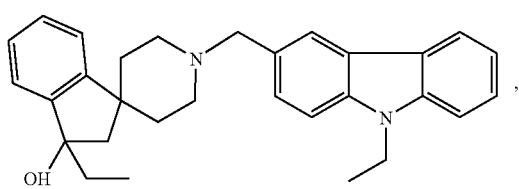

4

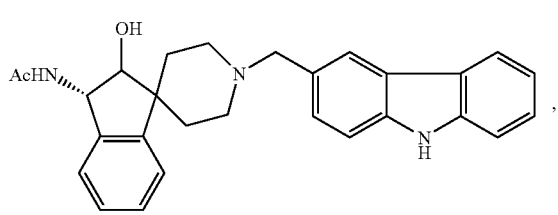

5

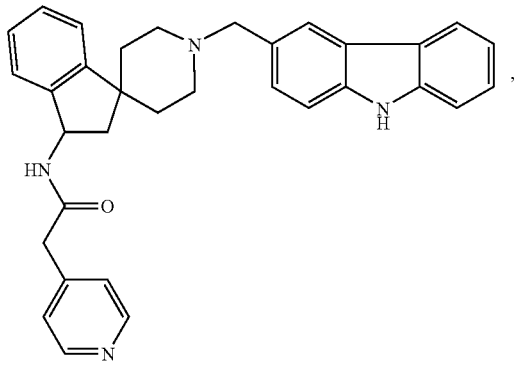

8

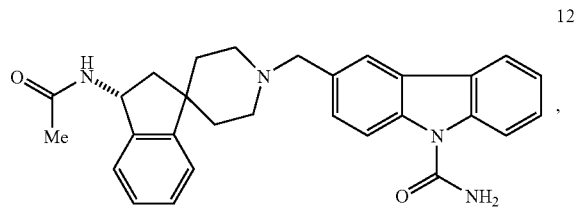

12

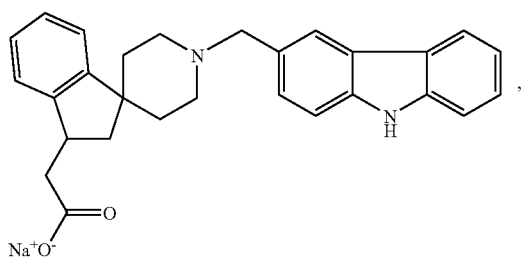

18

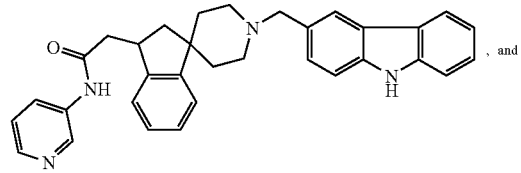

19

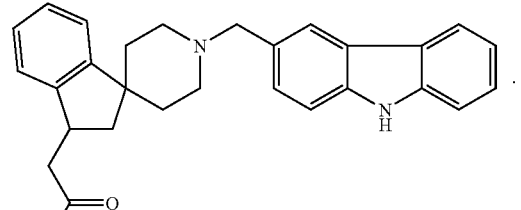

, and

20

.

23. The compound of claims 14, wherein L is methylene.

24. A pharmaceutical composition comprising a pharmaceutically acceptable carrier or excipient and a compound of claim 1.

25. A method of treating a condition or disorder selected from the group consisting of obesity, type II diabetes, hypertension, hyperuricemia, stroke, dyslipidemia, coronary artery disease, hypercholesterolemia and atherosclerosis, comprising administering to a subject in need thereof a therapeutically effective amount of a compound of claim 1.

* * * * *